US011618903B2

(12) United States Patent
Borsani Cambón et al.

(10) Patent No.: US 11,618,903 B2
(45) Date of Patent: Apr. 4, 2023

(54) METHODS FOR IMPROVING PLANT ABIOTIC STRESS TOLERANCE AND YIELD

(71) Applicants: INSTITUTO NACIONAL DE INVESTIGACIÓN AGROPECUARIA, Montevideo (UY); UNIVERSIDAD DE LA REPUBLICA, Montevideo (UY); CONSEJO NACIONAL DE INVESTIGACIONES CIENTIFICAS Y TECNICAS, Ciudad AutOnoma de Buenos Aires (AR); ESTACION EXPERIMENTAL AGROINDUSTRIAL OBISPO COLOMBRES, San Miguel de Tucuman (AR)

(72) Inventors: Julio Omar Borsani Cambón, Montevideo (UY); Esteban Casaretto De Gregorio, Montevideo (UY); Juan Pablo Gallino Malcuori, Montevideo (UY); Andrea Luciana Fleitas Belamendia, Montevideo (UY); Maria Victoria Bonnecarrère Martinez, Montevideo (UY); Atilio Pedro Castagnaro, Ciudad AutOnoma de Buenos Aires (AR); Esteban Mariano Pardo, San Miguel de Tucuman (AR); Sabina Vidal Macchi, Montevideo (UY)

(73) Assignees: INSTITUTO NACIONAL DE INVESTIGACION AGROPECUARIA, Montevideo (UY); UNIVERSIDAD DE LA REPUBLICA, Montevideo (UY); CONSEJO NACIONAL DE INVESTIGACIONES CIENTIFICAS Y TECNICAS, Buenos Aires (AR); ESTACION EXPERIMENTAL AGROINDUSTRIAL OBISPO COLOMBRES, Tucuman (AR)

( * ) Notice: Subject to any disclaimer, the term of this patent is extended or adjusted under 35 U.S.C. 154(b) by 0 days.

(21) Appl. No.: 16/956,526

(22) PCT Filed: Dec. 20, 2018

(86) PCT No.: PCT/EP2018/086228
§ 371 (c)(1),
(2) Date: Jun. 19, 2020

(87) PCT Pub. No.: WO2019/122146
PCT Pub. Date: Jun. 27, 2019

(65) Prior Publication Data
US 2022/0098609 A1 Mar. 31, 2022

Related U.S. Application Data

(60) Provisional application No. 62/608,983, filed on Dec. 21, 2017.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8201* (2013.01)

(58) Field of Classification Search
CPC ............ C12N 15/8273; C12N 15/8282; C12N 15/8283; C12N 15/8285; C12N 15/8286
See application file for complete search history.

(56) References Cited

PUBLICATIONS

Walker, G. P. "Sieve element occlusion: Interactions with phloem sap-feeding insects. A review." Journal of Plant Physiology (2021): 153582 (Year: 2021).*
Srivastava, Vineet Kumar, et al. "Ectopic expression of phloem motor protein pea forisome PsSEO-F1 enhances salinity stress tolerance in tobacco." Plant cell reports 35.5 (2016): 1021-1041. (Year: 2016).*
Rüping, Boris, et al. "Molecular and phylogenetic characterization of the sieve element occlusion gene family in *Fabaceae* and non-*Fabaceae*plants." BMC plant biology 10.1 (2010): 1-14. (Year: 2010).*

* cited by examiner

*Primary Examiner* — Weihua Fan
(74) *Attorney, Agent, or Firm* — Weatherly IP Solutions, LLC; James M. Weatherly

(57) ABSTRACT

The invention relates to methods for improving abiotic stress tolerance (and/or yield) in plants, including enhanced drought tolerance. It discloses nucleic acid constructs comprising the isolated polynucleotides, transgenic plants expressing the same, and methods of using the same for increasing abiotic stress tolerance (and/or yield).

10 Claims, 17 Drawing Sheets

Specification includes a Sequence Listing.

A. Tobacco wild type and *eIF(iso)4G*-overexpressing lines grown under osmotic stress B. Expression level of *eIF(iso)4G* in tobacco transgenic overexpressing lines A. Tobacco wild type and *SEO*-overexpressing lines grown under osmotic stress B. Expression level of *SEO* in tobacco transgenic overexpressing lines

NBT

SCHIFF

SEQUENCE LISTING

```
<160> NUMBER OF SEQ ID NOS: 18

<210> SEQ ID NO 1
<211> LENGTH: 2370
<212> TYPE: DNA
<213> ORGANISM: Glycine max

<400> SEQUENCE: 1
atgcagcaga gtgatcaaac ggtgttgagc ttgaggcccg gtggtggaag aggcagcagg     60
ctcctcgctc ctcgatccga ctcctcctct tcgtcctctg cttccctgc ttttggctcc     120 ttttccgctg atcttcctct cctgcgtccc cacgctggag ctccctctcc cttctctatc     180
aaagctggag atgctcggtt tgagggccgt gagcgtgtgc gatacacaag ggaacagctt     240
ttacagctta aagagggtgt tgagatcctc gatgatgttt taaagatcaa acaagatatt     300
gaagctgaac tttttggtga agatcaaagt tgggcccgcc cagaaaacaa ccccacacag     360
caatttcaaa atcgatatac tgagccagat aatcgtgact ggcgtggaag atctggccaa     420
ctttctggta atgcagatga gaggtcttgg gataatctca aggagaatag ggagtttggc     480
aatactagta atcgtcaaga ccaactgaac tctcagtttg caaggacaca aatctcttct     540
aaccaagggg gaggacctac tccgacacta gtcaaggctg aggtgccatg gtcagctaga     600
aggggaactc tctctgacaa ggatcgcgtc ctaaagacag ttaaaggaat actaaataag     660
ttgactccgg agaaatttga tctcctgaag ggtcagttga tcgattctgg cattacatca     720
gccgacatat tgaaggagt tatttcgctg atatttgata aggcagtgct ggaaccaaca     780
ttttgcccca tgtatgctca gctgtgttct gatcttaatg aaaagctgcc tccattccca     840
tctgacgagc ctggtgggaa agaaatcact tttaagcgag tactcttgaa tatctgccag     900
gaggcttttg aaggtgcaga taaactgagg gaagaactga gacagatgac tgcccctgac     960
caggagatgg agcgacggga caaggaaaga cttgtcaaga ttcgaaccct tggaaatatc    1020
cgtttaattg gtgagctgtt gaagcaaaaa atggttcccg aaaagattgt tcatcacatt    1080
gttcaggagc ttttaggacc tccagacatc aaggtctgtc cagctgagga aaatgttgaa    1140
gccatatgtc agtttttcaa cactattggt aagcagcttg atgaaagccc aaaatcacgg    1200
```

```
cgcataaatg atatgtactt tatccggttg aaagaattga gcaccaatcc ccaacttgca      1260
ccacggctgc ggtttatggt tcgtgatgtt ctagatttgc gttctaataa ctggattcca      1320
agacgtgaag aggtgaaagc caaaaccatc actgaaattc attcagaggc agaaaaaaat      1380
cttggattgc gtccaggtgc cactgcaagt atgagaaata accgtgtagt ttcaggcgct      1440
ctaggaaata ccagtccagg aggattccca attgctcgac ctggtacagg tggtttgatg      1500
ccagggatgc cagggaccag gaggatgcct gggatgcctg gaattgataa tgacaactgg      1560
gagatgccta agacaagatc aatgccgaga ggagacatgt caggcatgca aactggagga      1620
catagccagt cccctttct ttccaagaca tccactgtta actctaggtt actacctcaa       1680
ggtagtggtg gtattataag tgggagaagc agtgccctgg tgcatggagc tggtgctcct      1740
tctgctgctc ggccaccaaa ccttggtttt agtgctgaac ccacacctca aatcccttca      1800
cctgttaaag cggtttctgc catacccgct gagaagccac aacctccagc tgcaaaattg      1860
aattttgatg aacttcagcg taaaactgtt tctcttctgg aagaatattt caatgtccgg      1920
cttttggacg aggcattaca gtgtgtggag gaactaaaag ctccagctta ttaccctgag      1980
tttgtcaagg aagctatttc ccttgctcta gataaaagtc cgccatgcgc tgaacctgtc      2040
gccaatcttt ttgaatatct gttcattaag aagattcttt cagccagaga catagggact      2100
gggtgcatgt tatttgcttc tctgctggat gatatcggca tagatttacc taaagcacca      2160
aataattttg gtgagataat agggaaacta gttttggctg ggggtttgga ttttaaggtg      2220
gtgacagaaa tccttaagaa ggtggaggat gaccggttcc agaaagcaat atttcttct       2280 gcgttgcagg taattacctc tgcatctggg caagctgtgt tggatgcaca agcatctgat      2340
attgaggcct gccagagtct gttcaactga                                       2370

<210> SEQ ID NO 2
<211> LENGTH: 2013
<212> TYPE: DNA
<213> ORGANISM: Glycine max

<400> SEQUENCE: 2
atgagcatta tcatgtccac caagtcatcg ctgaagtctc tcctccaaaa gggtgagaat       60
gagcataatc cattaaccat gtctgatgaa cagattttgg aacaaattta ctcaacccac      120
gtccacagtg acaccaagtt tgatgtggat tctcttttca cccttgttga gaacactctt      180
agacgttcaa cccacattgt tgacaatctt gtgcagggat cccatgcaag cttggagcac      240
attgatgaca agatccccca attcaattca ccactttgta ccttgaagca aatttctttt      300
gagatgtcat gcaagcctcc aagtgaggaa attggtcacc gaactacact ggccatactt      360
aacaagctct caaactatga gtgggatgct aaggctgtgc tgacactagc agcttttgca      420
ctcgaatata gcgagttctg gctgctagca cagtaccaac caacagatcc tcttgcaaaa      480
tctgtggcta ttttgaagcg agtgccagtg ctcgcaaagc ccgcagcact tcaaaagcat      540
cgacaagcca tccttgaggt taacaatttg gtgaaagcaa cgttgcaagt tattgaggtt      600
atctttgagc tggagaagct taccacttat gacaccaaag atgtacctgc tttggggctt      660
gcaattgaac aaatccctgt tgatgtttac tgggccatca tcactatcgt cgctgtggtt      720
actcagattg attgtctcac cactgattca gagcacaagc aagaactgtc tcactatggt      780
caaaagatca acatcatact cagcaaactc aggaagcaga taactctctg cagacaacag      840
atagatgagg cacaatatta tcgcaagctg aggaaatttt tccaaccccc cactgaaata      900
atggaggtgt ttaaggttct gattttcaat aaggatgctc ctcagccact gttcgatggt      960
```

```
gctactaaga ctaaggtcga tatcacggtg ctaaaaaaga agaacgtgta cttgtttatt      1020
tcttccctgg acatcacgga ggaagagatt tcagtactcc gaccagttta tgattctatt      1080
aaaactaacg atcagtataa gattgtgtgg attcccattg tagaagaatg gaccgagcaa      1140
ttgcacaaga aatttgaggt tttgaaaagc aagatgcctt ggtatgtggt gcagcattct      1200
ggaaccatag cagggtacaa gtacattaag gaggaatggc acttcaaaaa gaagcctatg      1260
gttgtggtgt tgagccctca agggaaggtg caacactcaa acgcattcca tttgatccag      1320
gctcatggaa ccagggcttt tccctttaca actttgaatg aagaaaaaat aaacagtgag      1380
aacgattggg ttggctccgt attaggcagc attcacccca gcataagcac ctcgcagatc      1440
aaagagcaaa agtacatttt cttttatggg ggcaacgaca agactggat ccaacagttc       1500 accaagtacg ttactgccct tgcaaatgat gctgctataa aggaggcaaa gatttccata      1560
gagttgtttt gtgtggataa ggaagacaaa agccttgtga ggcgcttttg gagtggcatt      1620
gagagtttat ttgtgactaa ggttcacaaa caagctgatg cagtgactca agaagtgcaa      1680
aagatgcttt cttacaagaa tgaaactgga tggtctctcc tcagtaaagg gccatcagtg      1740
gtggtgagtg gtcatggaac aacaatcttg aagacagtgg cagagtttga gaatggaaaa      1800
gaggttgtga tcaaaaaggg ctttgcggta accttcaaag aataccatca gaagattgtg      1860
gggaccactc accgttgctc acaccttgag attcctaacg ttgcagggaa gttacctgag      1920
accatcaaat gctcagattg tcctagggta atggagattt tcatcagcta taaatgctgc      1980
cacaatgaga atactgccaa tgccattcac tag                                    2013

<210> SEQ ID NO 3
<211> LENGTH: 2370
<212> TYPE: DNA
<213> ORGANISM: Glycine max

<400> SEQUENCE: 3
atgcagcaga gtgatcaaac ggtgttgagc ttgaggcccg gtggtggaag aggcagcagg        60
ctcctcgctc ctcgatccga ctcctcctct tcgtcctctg cttcccctgc ttttggctcc       120
ttttccgctg atcttcctct cctgcgtccc cacgctggag ctccctctcc cttctctatc       180
aaagctggag atgctcggtt tgagggccgt gagcgtgtgc gatacacaag ggaacagctt       240
ttacagctta agagggtgt tgagatcctc gatgatgttt taaagatcaa acaagatatt        300
gaagctgaac tttttggtga agatcaaagt tgggcccgcc cagaaaacaa ccccacacag       360
caatttcaaa atcgatatac tgagccagat aatcgtgact ggcgtggaag atctggccaa       420 cttctggta atgcagatga gaggtcttgg gataatctca aggagaatag ggagtttggc        480
aatactagta atcgtcaaga ccaactgaac tctcagtttg caaggacaca aatctcttct       540
aaccaagggg gaggacctac tccgacacta gtcaaggctg aggtgccatg gtcagctaga      600
aggggaactc tctctgacaa ggatcgcgtc ttaaagacag ttaaaggaat actaaataag       660
ttgactccgg agaaatttga tctcctgaag ggtcagttga tcgattctgg cattacatca       720
gccgacatat tgaagggagt tatttcgctg atatttgata aggcagtgct ggaaccaaca       780
ttttgcccca tgtatgctca gctgtgttct gatcttaatg aaaagctgcc tccattccca       840
tctgacgagc tggtgggaa agaaatcact tttaagcgag tactcttgaa tatctgccag       900
gaggcttttg aaggtgcaga taaactgagg aagaactga gacagatgac tgcccctgac       960
caggagatgg agcgacggga caaggaaaga cttgtcaaga ttcgaaccct tggaaatatc      1020
```

-continued

```
cgtttaattg gtgagctgtt gaagcaaaaa atggttcccg aaaagattgt tcatcacatt    1080
gttcaggagc ttttaggacc tccagacatc aaggtctgtc cagctgagga aatgttgaa     1140 gccatatgtc agttttcaa cactattggt aagcagcttg atgaaagccc aaaatcacgg     1200
cgcataaatg atatgtactt tatccggttg aaagaattga gcaccaatcc ccaacttgca    1260
ccacggctgc ggtttatggt tcgtgatgtt ctagatttgc gttctaataa ctggattcca    1320
agacgtgaag aggtgaaagc caaaaccatc actgaaattc attcagaggc agaaaaaaat    1380
cttggattgc gtccaggtgc cactgcaagt atgagaaata accgtgtagt ttcaggcgct    1440
ctaggaaata ccagtccagg aggattccca attgctcgac ctggtacagg tggtttgatg    1500
ccagggatgc cagggaccag gaggatgcct gggatgcctg gaattgataa tgacaactgg    1560
gagatgccta agacaagatc aatgccgaga ggagacatgt caggcatgca aactggagga    1620
catagccagt ctccctttct ttccaagaca tccactgtta actctaggtt actacctcaa    1680
ggtagtggtg gtattataag tgggagaagc agtgccctgg tgcatggagc tggtgctcct    1740
tctgctgctc ggccaccaaa ccttggtttt agtgctgaac ccacacctca aatcccttca    1800
cctgttaaag ctgtttctgc catcccgct gagaagccac aacctccagc tgcaaaattg     1860
aattttgatg aacttcagcg taaaactgtt tctcttctgg aagaatattt caatgtccgg    1920
cttttggacg aggcattaca gtgtgtggag gaactaaaag ctccagctta ttaccctgag    1980
tttgtcaagg aagctatttc ccttgctcta gataaaagtc cgccatgcgc tgaacctgtt    2040
gccaatcttt ttgaatatct gttcattaag aagattcttt cagccagaga catagggact    2100
gggtgcatgt tatttgcttc tctgctggat gatatcggca tagatttacc taaagcacca    2160
aataattttg gtgagataat agggaaacta gttttggctg ggggtttgga ttttaaggtg    2220
gtgacagaaa tccttaagaa ggtggaggat gaccggttcc agaaagcaat attttcttct    2280
gcgttgcagg taattacctc tgcatctggg caagctgtgt tggatgcaca agcatctgat    2340
attgaggcct gccagagtct gttcaactga                                     2370
```

<210> SEQ ID NO 4
<211> LENGTH: 2370
<212> TYPE: DNA
<213> ORGANISM: Glycine max

<400> SEQUENCE: 4

```
atgcagcaga gtgatcaaac ggtgttgagc ttgaggcccg gtggtggaag aggcagcagg     60
ctcctcgctc ctcgattcga ctcctcctct tcgtcctctg cttcccctgc ttttggctcc    120
ttttccgctg atcttcctct cctgcgtccc cacgctggag ctccctctcc cttctctatc    180
aaagctggag atgctcggtt tgagggccgt gagcgtgtgc gatacacaag gaacagctt     240 ttacagctta agagggtgt tgagatcctc gatgatgttt taaagatcaa acaagatatt     300
gaagctgaac ttttggtga agatcaaagt tgggcccgcc cagaaaacaa ccccacacag     360
caatttcaaa atcgatatac tgagccagat aatcgtgact ggcgtggaag atctggccaa    420
ctttctggta atgcagatga gaggtcttgg gataatctca aggagaatag ggagtttggc    480
aatactagta atcgtcaaga ccaactgaac tctcagtttg caaggacaca aatctcttct    540
aaccaagggg aggacctac tccgacacta gtcaaggctg aggtgccatg gtcagctaga    600
aggggaactc tctctgacaa ggatcgcgtc ttaaagacag ttaaaggaat actaataaag    660
ttgactccgg agaaatttga tctcctgaag ggtcagttga tcgattctgg cattacatca    720
gccgacatat tgaagggagt tatttcgctg atatttgata aggcagtgct ggaaccaaca    780
```

-continued

```
ttttgcccca tgtatgctca gctgtgttct gatcttaatg aaaagctgcc tccattccca    840
tctgacgagc ctggtgggaa agaaatcact tttaagcgag tactcttgaa tatctgccag    900
gaggcttttg aaggtgcaga taaactgagg gaagaactga gacagatgac tgcccctgac    960
caggagatgg agcgacggga caaggaaaga cttgtcaaga ttcgaaccct tggaaatatc   1020
cgtttaattg gtgagctgtt gaagcaaaaa atggttcccg aaaagattgt tcatcacatt   1080
gttcaggagc ttttaggacc tccagacatc aaggtctgtc cagctgagga aaatgttgaa   1140
gccatatgtc agttttttcaa cactattggt aagcagcttg atgaaagccc aaaatcacgg   1200
cgcataaatg atatgtactt tatccggttg aaagaattga gcaccaatcc ccaacttgca   1260
ccacggctgc ggtttatggt tcgtgatgtt ctagatttgc gttctaataa ctggattcca   1320
agacgtgaag aggtgaaagc caaaaccatc actgaaattc attcagaggc agaaaaaaat   1380
cttggattgc gtccaggtgc cactgcaagt atgagaaata ccgtgtagt tcaggcgct   1440 ctaggaaata ccagtccagg aggattccca attgctcgac ctggtacagg tggtttgatg   1500
ccagggatgc cagggaccag gaggatgcct gggatgcctg gaattgataa tgacaactgg   1560
gagatgccta agacaagatc aatgccgaga ggagacatgt caggcatgca aactggagga   1620
catagccagt ctcccttcct ttccaagaca tccactgtta actctaggtt actacctcaa   1680
ggtagtggtg gtattataag tgggagaagc agtgccctgg tgcatggagc tggtgctcct   1740
tctgctgctc ggccaccaaa ccttggtttt agtgctgaac ccacacctca aatcccttca   1800
cctgttaaag ctgtttctgc catcccgct gagaagccac aacctccagc tgcaaaattg   1860
aattttgatg aacttcagcg taaaactgtt tctcttctgg aagaatattt caatgtccgg   1920
cttttggacg aggcattaca gtgtgtggag gaactaaaag ctccagctta ttaccctgag   1980
tttgtcaagg aagctatttc ccttgctcta gataaaagtc cgccatgcgc tgaacctgtt   2040
gccaatcttt ttgaatatct gttcattaag aagattcttt cagccagaga catagggact   2100
gggtgcatgt tatttgcttc tctgctggat gatatcggca tagatttacc taaagcacca   2160
aataattttg gtgagataat agggaaacta gttttggctg ggggtttgga ttttaaggtg   2220
gtgacagaaa tccttaagaa ggtggaggat gaccggttcc agaaagcaat attttcttct   2280
gcgttgcagg taattacctc tgcatctggg caagctgtgc tggatgcaca agcatctgat   2340
attgaggcct gccagagtct gttcaactga                                    2370
```

<210> SEQ ID NO 5
<211> LENGTH: 789
<212> TYPE: PRT
<213> ORGANISM: Glycine max

<400> SEQUENCE: 5

Met Gln Gln Ser Asp Gln Thr Val Leu Ser Leu Arg Pro Gly Gly Gly
1               5                   10                  15

Arg Gly Ser Arg Leu Leu Ala Pro Arg Ser Asp Ser Ser Ser Ser Ser
            20                  25                  30

Ser Ala Ser Pro Ala Phe Gly Ser Phe Ser Ala Asp Leu Pro Leu Leu
        35                  40                  45

Arg Pro His Ala Gly Ala Pro Ser Pro Phe Ser Ile Lys Ala Gly Asp
    50                  55                  60

Ala Arg Phe Glu Gly Arg Glu Arg Val Arg Tyr Thr Arg Glu Gln Leu
65                  70                  75                  80

```
Leu Gln Leu Lys Glu Gly Val Glu Ile Leu Asp Asp Val Leu Lys Ile
                85                  90                  95

Lys Gln Asp Ile Glu Ala Glu Leu Phe Gly Glu Asp Gln Ser Trp Ala
                100                 105                 110

Arg Pro Glu Asn Asn Pro Thr Gln Gln Phe Gln Asn Arg Tyr Thr Glu
                115                 120                 125

Pro Asp Asn Arg Asp Trp Arg Gly Arg Ser Gly Gln Leu Ser Gly Asn
            130                 135                 140

Ala Asp Glu Arg Ser Trp Asp Asn Leu Lys Glu Asn Arg Glu Phe Gly
145                 150                 155                 160

Asn Thr Ser Asn Arg Gln Asp Gln Leu Asn Ser Gln Phe Ala Arg Thr
                165                 170                 175

Gln Ile Ser Ser Asn Gln Gly Gly Pro Thr Pro Thr Leu Val Lys
                180                 185                 190

Ala Glu Val Pro Trp Ser Ala Arg Arg Gly Thr Leu Ser Asp Lys Asp
                195                 200                 205

Arg Val Leu Lys Thr Val Lys Gly Ile Leu Asn Lys Leu Thr Pro Glu
            210                 215                 220

Lys Phe Asp Leu Leu Lys Gly Gln Leu Ile Asp Ser Gly Ile Thr Ser
225                 230                 235                 240

Ala Asp Ile Leu Lys Gly Val Ile Ser Leu Ile Phe Asp Lys Ala Val
                245                 250                 255

Leu Glu Pro Thr Phe Cys Pro Met Tyr Ala Gln Leu Cys Ser Asp Leu
                260                 265                 270

Asn Glu Lys Leu Pro Pro Phe Pro Ser Asp Glu Pro Gly Gly Lys Glu
                275                 280                 285

Ile Thr Phe Lys Arg Val Leu Leu Asn Ile Cys Gln Glu Ala Phe Glu
                290                 295                 300

Gly Ala Asp Lys Leu Arg Glu Glu Leu Arg Gln Met Thr Ala Pro Asp
305                 310                 315                 320

Gln Glu Met Glu Arg Arg Asp Lys Glu Arg Leu Val Lys Ile Arg Thr
                325                 330                 335

Leu Gly Asn Ile Arg Leu Ile Gly Glu Leu Leu Lys Gln Lys Met Val
                340                 345                 350

Pro Glu Lys Ile Val His His Ile Val Gln Glu Leu Leu Gly Pro Pro
                355                 360                 365

Asp Ile Lys Val Cys Pro Ala Glu Glu Asn Val Glu Ala Ile Cys Gln
            370                 375                 380

Phe Phe Asn Thr Ile Gly Lys Gln Leu Asp Glu Ser Pro Lys Ser Arg
385                 390                 395                 400

Arg Ile Asn Asp Met Tyr Phe Ile Arg Leu Lys Glu Leu Ser Thr Asn
                405                 410                 415

Pro Gln Leu Ala Pro Arg Leu Arg Phe Met Val Arg Asp Val Leu Asp
                420                 425                 430

Leu Arg Ser Asn Asn Trp Ile Pro Arg Arg Glu Glu Val Lys Ala Lys
            435                 440                 445

Thr Ile Thr Glu Ile His Ser Glu Ala Glu Lys Asn Leu Gly Leu Arg
                450                 455                 460

Pro Gly Ala Thr Ala Ser Met Arg Asn Asn Arg Val Val Ser Gly Ala
465                 470                 475                 480

Leu Gly Asn Thr Ser Pro Gly Gly Phe Pro Ile Ala Arg Pro Gly Thr
                485                 490                 495
```

```
Gly Gly Leu Met Pro Gly Met Pro Gly Thr Arg Arg Met Pro Gly Met
            500                 505                 510

Pro Gly Ile Asp Asn Asp Asn Trp Glu Met Pro Lys Thr Arg Ser Met
            515                 520                 525

Pro Arg Gly Asp Met Ser Gly Met Gln Thr Gly Gly His Ser Gln Ser
        530                 535                 540

Pro Phe Leu Ser Lys Thr Ser Thr Val Asn Ser Arg Leu Leu Pro Gln
545                 550                 555                 560

Gly Ser Gly Gly Ile Ile Ser Gly Arg Ser Ser Ala Leu Val His Gly
                565                 570                 575

Ala Gly Ala Pro Ser Ala Ala Arg Pro Pro Asn Leu Gly Phe Ser Ala
            580                 585                 590

Glu Pro Thr Pro Gln Ile Pro Ser Pro Val Lys Ala Val Ser Ala Ile
            595                 600                 605

Pro Ala Glu Lys Pro Gln Pro Pro Ala Ala Lys Leu Asn Phe Asp Glu
        610                 615                 620

Leu Gln Arg Lys Thr Val Ser Leu Leu Glu Glu Tyr Phe Asn Val Arg
625                 630                 635                 640

Leu Leu Asp Glu Ala Leu Gln Cys Val Glu Glu Leu Lys Ala Pro Ala
                645                 650                 655

Tyr Tyr Pro Glu Phe Val Lys Glu Ala Ile Ser Leu Ala Leu Asp Lys
            660                 665                 670

Ser Pro Pro Cys Ala Glu Pro Val Ala Asn Leu Phe Glu Tyr Leu Phe
        675                 680                 685

Ile Lys Lys Ile Leu Ser Ala Arg Asp Ile Gly Thr Gly Cys Met Leu
690                 695                 700

Phe Ala Ser Leu Leu Asp Asp Ile Gly Ile Asp Leu Pro Lys Ala Pro
705                 710                 715                 720

Asn Asn Phe Gly Glu Ile Ile Gly Lys Leu Val Leu Ala Gly Gly Leu
                725                 730                 735

Asp Phe Lys Val Val Thr Glu Ile Leu Lys Lys Val Glu Asp Asp Arg
            740                 745                 750

Phe Gln Lys Ala Ile Phe Ser Ser Ala Leu Gln Val Ile Thr Ser Ala
        755                 760                 765

Ser Gly Gln Ala Val Leu Asp Ala Gln Ala Ser Asp Ile Glu Ala Cys
770                 775                 780

Gln Ser Leu Phe Asn
785

<210> SEQ ID NO 6
<211> LENGTH: 789
<212> TYPE: PRT
<213> ORGANISM: Glycine max

<400> SEQUENCE: 6

Met Gln Gln Ser Asp Gln Thr Val Leu Ser Leu Arg Pro Gly Gly Gly
1               5                   10                  15

Arg Gly Ser Arg Leu Leu Ala Pro Arg Phe Asp Ser Ser Ser Ser Ser
            20                  25                  30

Ser Ala Ser Pro Ala Phe Gly Ser Phe Ser Ala Asp Leu Pro Leu Leu
        35                  40                  45

Arg Pro His Ala Gly Ala Pro Ser Pro Phe Ser Ile Lys Ala Gly Asp
    50                  55                  60

Ala Arg Phe Glu Gly Arg Glu Arg Val Arg Tyr Thr Arg Glu Gln Leu
65                  70                  75                  80
```

```
Leu Gln Leu Lys Glu Gly Val Glu Ile Leu Asp Asp Val Leu Lys Ile
                85                  90                  95

Lys Gln Asp Ile Glu Ala Glu Leu Phe Gly Glu Asp Gln Ser Trp Ala
            100                 105                 110

Arg Pro Glu Asn Asn Pro Thr Gln Gln Phe Gln Asn Arg Tyr Thr Glu
        115                 120                 125

Pro Asp Asn Arg Asp Trp Arg Gly Arg Ser Gly Gln Leu Ser Gly Asn
    130                 135                 140

Ala Asp Glu Arg Ser Trp Asp Asn Leu Lys Glu Asn Arg Glu Phe Gly
145                 150                 155                 160

Asn Thr Ser Asn Arg Gln Asp Gln Leu Asn Ser Gln Phe Ala Arg Thr
                165                 170                 175

Gln Ile Ser Ser Asn Gln Gly Gly Pro Thr Pro Thr Leu Val Lys
            180                 185                 190

Ala Glu Val Pro Trp Ser Ala Arg Arg Gly Thr Leu Ser Asp Lys Asp
        195                 200                 205

Arg Val Leu Lys Thr Val Lys Gly Ile Leu Asn Lys Leu Thr Pro Glu
    210                 215                 220

Lys Phe Asp Leu Leu Lys Gly Gln Leu Ile Asp Ser Gly Ile Thr Ser
225                 230                 235                 240

Ala Asp Ile Leu Lys Gly Val Ile Ser Leu Ile Phe Asp Lys Ala Val
                245                 250                 255

Leu Glu Pro Thr Phe Cys Pro Met Tyr Ala Gln Leu Cys Ser Asp Leu
            260                 265                 270

Asn Glu Lys Leu Pro Pro Phe Pro Ser Asp Glu Pro Gly Gly Lys Glu
        275                 280                 285

Ile Thr Phe Lys Arg Val Leu Leu Asn Ile Cys Gln Glu Ala Phe Glu
    290                 295                 300

Gly Ala Asp Lys Leu Arg Glu Glu Leu Arg Gln Met Thr Ala Pro Asp
305                 310                 315                 320

Gln Glu Met Glu Arg Arg Asp Lys Glu Arg Leu Val Lys Ile Arg Thr
                325                 330                 335

Leu Gly Asn Ile Arg Leu Ile Gly Glu Leu Leu Lys Gln Lys Met Val
            340                 345                 350

Pro Glu Lys Ile Val His His Ile Val Gln Glu Leu Leu Gly Pro Pro
        355                 360                 365

Asp Ile Lys Val Cys Pro Ala Glu Glu Asn Val Glu Ala Ile Cys Gln
    370                 375                 380

Phe Phe Asn Thr Ile Gly Lys Gln Leu Asp Glu Ser Pro Lys Ser Arg
385                 390                 395                 400

Arg Ile Asn Asp Met Tyr Phe Ile Arg Leu Lys Glu Leu Ser Thr Asn
                405                 410                 415

Pro Gln Leu Ala Pro Arg Leu Arg Phe Met Val Arg Asp Val Leu Asp
            420                 425                 430

Leu Arg Ser Asn Asn Trp Ile Pro Arg Arg Glu Glu Val Lys Ala Lys
        435                 440                 445

Thr Ile Thr Glu Ile His Ser Glu Ala Glu Lys Asn Leu Gly Leu Arg
    450                 455                 460

Pro Gly Ala Thr Ala Ser Met Arg Asn Asn Arg Val Val Ser Gly Ala
465                 470                 475                 480

Leu Gly Asn Thr Ser Pro Gly Gly Phe Pro Ile Ala Arg Pro Gly Thr
                485                 490                 495
```

```
Gly Gly Leu Met Pro Gly Met Pro Gly Thr Arg Met Pro Gly Met
            500                 505                 510
Pro Gly Ile Asp Asn Asp Asn Trp Glu Met Pro Lys Thr Arg Ser Met
            515                 520                 525
Pro Arg Gly Asp Met Ser Gly Met Gln Thr Gly Gly His Ser Gln Ser
        530                 535                 540
Pro Phe Leu Ser Lys Thr Ser Thr Val Asn Ser Arg Leu Leu Pro Gln
545                 550                 555                 560
Gly Ser Gly Gly Ile Ile Ser Gly Arg Ser Ser Ala Leu Val His Gly
                565                 570                 575
Ala Gly Ala Pro Ser Ala Ala Arg Pro Pro Asn Leu Gly Phe Ser Ala
            580                 585                 590
Glu Pro Thr Pro Gln Ile Pro Ser Pro Val Lys Ala Val Ser Ala Ile
            595                 600                 605
Pro Ala Glu Lys Pro Gln Pro Pro Ala Ala Lys Leu Asn Phe Asp Glu
        610                 615                 620
Leu Gln Arg Lys Thr Val Ser Leu Leu Glu Glu Tyr Phe Asn Val Arg
625                 630                 635                 640
Leu Leu Asp Glu Ala Leu Gln Cys Val Glu Glu Leu Lys Ala Pro Ala
                645                 650                 655
Tyr Tyr Pro Glu Phe Val Lys Glu Ala Ile Ser Leu Ala Leu Asp Lys
            660                 665                 670
Ser Pro Pro Cys Ala Glu Pro Val Ala Asn Leu Phe Glu Tyr Leu Phe
            675                 680                 685
Ile Lys Lys Ile Leu Ser Ala Arg Asp Ile Gly Thr Gly Cys Met Leu
        690                 695                 700
Phe Ala Ser Leu Leu Asp Asp Ile Gly Ile Asp Leu Pro Lys Ala Pro
705                 710                 715                 720
Asn Asn Phe Gly Glu Ile Ile Gly Lys Leu Val Leu Ala Gly Gly Leu
                725                 730                 735
Asp Phe Lys Val Val Thr Glu Ile Leu Lys Lys Val Glu Asp Asp Arg
            740                 745                 750
Phe Gln Lys Ala Ile Phe Ser Ser Ala Leu Gln Val Ile Thr Ser Ala
            755                 760                 765
Ser Gly Gln Ala Val Leu Asp Ala Gln Ala Ser Asp Ile Glu Ala Cys
        770                 775                 780
Gln Ser Leu Phe Asn
785

<210> SEQ ID NO 7
<211> LENGTH: 670
<212> TYPE: PRT
<213> ORGANISM: Glycine max

<400> SEQUENCE: 7

Met Ser Ile Ile Met Ser Thr Lys Ser Ser Leu Lys Ser Leu Leu Gln
1               5                   10                  15
Lys Gly Glu Asn Glu His Asn Pro Leu Thr Met Ser Asp Glu Gln Ile
            20                  25                  30
Leu Glu Gln Ile Tyr Ser Thr His Val His Ser Asp Thr Lys Phe Asp
        35                  40                  45
Val Asp Ser Leu Phe Thr Leu Val Glu Asn Thr Leu Arg Arg Ser Thr
    50                  55                  60
His Ile Val Asp Asn Leu Val Gln Gly Ser His Ala Ser Leu Glu His
65                  70                  75                  80
```

```
Ile Asp Asp Lys Ile Pro Gln Phe Asn Ser Pro Leu Cys Thr Leu Lys
                85                  90                  95

Gln Ile Ser Phe Glu Met Ser Cys Lys Pro Pro Ser Glu Glu Ile Gly
                100                 105                 110

His Arg Thr Thr Leu Ala Ile Leu Asn Lys Leu Ser Asn Tyr Glu Trp
                115                 120                 125

Asp Ala Lys Ala Val Leu Thr Leu Ala Ala Phe Ala Leu Glu Tyr Ser
    130                 135                 140

Glu Phe Trp Leu Leu Ala Gln Tyr Gln Pro Thr Asp Pro Leu Ala Lys
145                 150                 155                 160

Ser Val Ala Ile Leu Lys Arg Val Pro Val Leu Ala Lys Pro Ala Ala
                165                 170                 175

Leu Gln Lys His Arg Gln Ala Ile Leu Glu Val Asn Asn Leu Val Lys
                180                 185                 190

Ala Thr Leu Gln Val Ile Glu Val Ile Phe Glu Leu Glu Lys Leu Thr
                195                 200                 205

Thr Tyr Asp Thr Lys Asp Val Pro Ala Leu Gly Leu Ala Ile Glu Gln
210                 215                 220

Ile Pro Val Asp Val Tyr Trp Ala Ile Ile Thr Ile Val Ala Val Val
225                 230                 235                 240

Thr Gln Ile Asp Cys Leu Thr Thr Asp Ser Glu His Lys Gln Glu Leu
                245                 250                 255

Ser His Tyr Gly Gln Lys Ile Asn Ile Ile Leu Ser Lys Leu Arg Lys
                260                 265                 270

Gln Ile Thr Leu Cys Arg Gln Gln Ile Asp Glu Ala Gln Tyr Tyr Arg
                275                 280                 285

Lys Leu Arg Lys Phe Phe Gln Thr Pro Thr Gly Ile Met Glu Val Phe
    290                 295                 300

Lys Val Leu Ile Phe Asn Lys Asp Ala Pro Gln Pro Leu Phe Asp Gly
305                 310                 315                 320

Ala Thr Lys Thr Lys Val Asp Ile Thr Val Leu Lys Lys Lys Asn Val
                325                 330                 335

Tyr Leu Phe Ile Ser Ser Leu Asp Ile Thr Glu Glu Ile Ser Val
                340                 345                 350

Leu Arg Pro Val Tyr Asp Ser Ile Lys Thr Asn Asp Gln Tyr Lys Ile
    355                 360                 365

Val Trp Ile Pro Ile Val Glu Glu Trp Thr Gln Leu His Lys Lys
    370                 375                 380

Phe Glu Val Leu Lys Ser Lys Met Pro Trp Tyr Val Gln His Ser
385                 390                 395                 400

Gly Thr Ile Ala Gly Tyr Lys Tyr Ile Lys Glu Glu Trp His Phe Lys
                405                 410                 415

Lys Lys Pro Met Val Val Val Leu Ser Pro Gln Gly Lys Val Gln His
                420                 425                 430

Ser Asn Ala Phe His Leu Ile Gln Ala His Gly Thr Arg Ala Phe Pro
    435                 440                 445

Phe Thr Thr Leu Asn Glu Glu Lys Ile Asn Ser Glu Asn Asp Trp Val
    450                 455                 460

Gly Ser Val Leu Gly Ser Ile His Pro Ser Ile Ser Thr Ser Gln Ile
465                 470                 475                 480

Lys Glu Gln Lys Tyr Ile Phe Pro Tyr Gly Gly Asn Asp Lys Asp Trp
                485                 490                 495
```

```
Ile Gln Gln Phe Thr Lys Tyr Val Thr Ala Leu Ala Asn Asp Ala Ala
                500                 505                 510
Ile Lys Glu Ala Lys Ile Ser Ile Glu Leu Phe Cys Val Asp Lys Glu
            515                 520                 525
Asp Lys Ser Leu Val Arg Arg Phe Trp Ser Gly Ile Glu Ser Leu Phe
        530                 535                 540
Val Thr Lys Val His Lys Gln Ala Asp Ala Val Thr Gln Glu Val Gln
545                 550                 555                 560
Lys Met Leu Ser Tyr Lys Asn Glu Thr Gly Trp Ser Leu Leu Ser Lys
                565                 570                 575
Gly Pro Ser Val Val Ser Gly His Gly Thr Thr Ile Leu Lys Thr
            580                 585                 590
Val Ala Glu Phe Glu Lys Trp Lys Glu Val Val Ile Lys Lys Gly Phe
        595                 600                 605
Ala Val Thr Phe Lys Glu Tyr His Gln Lys Ile Val Gly Thr Thr His
    610                 615                 620
Arg Cys Ser His Leu Glu Ile Pro Asn Val Ala Gly Lys Leu Pro Glu
625                 630                 635                 640
Thr Ile Lys Cys Ser Asp Cys Pro Arg Val Met Glu Ile Phe Ile Ser
                645                 650                 655
Tyr Lys Cys Cys His Asn Glu Asn Thr Ala Asn Ala Ile His
                660                 665                 670

<210> SEQ ID NO 8
<211> LENGTH: 8412
<212> TYPE: DNA
<213> ORGANISM: Glycine max

<400> SEQUENCE: 8
aaaaacaagg acatttggaa gagttttact gagcctcgtg ctggacacca taatgttata      60
ttgatagagt gaaataaat gaaagaaaa cgaattgaaa taaagttttt gaattaaatt       120
agagtgaaaa agtgtaaatt ttatcttatt ttactgttta ttttatttct tttcattct      180 ttttccactc aaaggaacag acacttagag attgtccaac gaaattttat ggctagttca     240
ttcaagtgtg ttaagacttt ctttttaaat gctaaaagaa tttagactta agctatttgg    300
tggttatcca aatggtaaga gataatatat ctttgtgttt gtggcctcta gtttggtact   360
tatttttcaa ggcatacaat aagggttaac ttggtatatc acatgttaag ttaaaaggtc    420
caatgttgtt tggttgaggt ttcaattaag ttagtctcat aattttcccg acaaattgat    480
tcaatacaag cataatttga aactcaaact caaacttgac cataaagcta aatcaaaaac    540
cataaagtgt actcttatgc atgattaaat taccataaat agaagaaaat aaatattaat    600
attaaaaaat tcattcaaat ttcattaaca gcaggttagt cacaaccca cccattttct    660 atttatatta agtatacttt tctcactta aaaataaca atgtttactt atgtggtggt     720
tcctatagtt atacaatctt tacattttag cctttacacc taaaacctac ttgttttagt    780
cattatacat atatttttaa tttgttttgg tctacacatt tcctttttaa ttcagtttaa   840
tcaatacaat acaattccag acgatgaaaa gattaaaaca aatttaaaag tgttagaaga    900
taagaaaatt gatattactt ttctctaatt atctaaggat gaaattattg attgtgggga    960
gttgctattg gcccctaaaa atatgagaaa aacattctt accctccctc ttcccctcgc    1020
cttcttctca ccccacccaa cccatcacca ctgcaccaac gacgccatca ccgtcacctc    1080
ctctgtccat atttgaacta gcgaccccaa tgttgttgta gcaacattcc aacaatggca    1140
```

```
tgtgccactc tcgaccacca cgccgttgca acattgtgca accccttgat cctacatatt    1200
tgttcatatt gttgcgtgtt ttcatcgtcg ctatgatcaa acaccctaga tatgcatcaa    1260
cttagaccca tcaacccaga tcttcaccac caccatcaaa tttatcctat tcaaaggaag    1320
aaaaagaggg aaacaaaagc atagtcccat tttgggtaaa aaacaatagt agaatcacaa    1380
ttttgttgtg ttattttcct tgtatccctt ttagaaagca atgaaaagca tgatttcatt    1440
gtacaatgtg cagcgtaatt gtgtttccat tatttttttt gcaccccttc ataaaacaac    1500
gaaaacacaa tttcattgta aaaaaaattg tgttttcgtt atttttttt gtacccttc     1560 gtaaaataac aaaaatatga tttttttttc ttgcatccca tttagaaagc aacaaaaaac    1620
acaaaattgt tgtacaattt gtaacacaat catgtttcca ttattttttt cttgcaccct    1680
ctgaaaaaaa caacgaaaac ccaatttcat cgtataaaga aatcatgttt tcatgaaaaa    1740
agtaaaaaaa atattgtgta accccttaat tggggccaat agcaaagggg ttgaggccaa    1800
taactaactc ttttttttt ggggtacaa tggtcgcatt aagatttgaa tttatgaaaa     1860
tacaaaatat tataaaaaat ctaaacctgt aatggtacat tgagttactt ttttatttgt    1920
tttgaaatta ttataaaaat acaaaatata cctgttaagc aaaaagagca atcttcttct    1980
cgttatatct ctacagtggg ccgtggcttg gccgcccagc ccacacgcat ttaagcctgg    2040
atgcctgcgt gtatatccat ctatattttc gacaaaaaac actatatgct atatgatata    2100
tggtatatac tatatactat tcagtataca aagacttttt cttcaaaaaa aaaaattcag    2160
tatacaaaga ggcagagaca ggcaaaaata tattttgta tttatatgat tcggtgatta    2220
gatttcatta gaacgaaatt atgtcctcaa taatcccaat tccaagtact gtcgaagata    2280
ataaggtaat aacaaccgac catgggcaaa tgtcaatttc ctgtttctgt tggggtgtcc    2340
gaagaaataa ttaaaatata atattgggcg agatttgaaa tacgtataga tacggtaggc    2400
tacgacataa cacaactcgt ctaagaaggg ttttttgtca cccctccgtt gtttctcact    2460
cactcacgca cgcagtactc tcttttcttc tcactccgca gaagagagag aaatatccaa    2520
tacctagcgt tagcgtactc tctcccaatc ccaatccttt tttctctcta tctatctatt    2580 catcccttc tcttcttctt ctattccctc ttctccttcc gcttctcctc tttatcgctg     2640
ttgtggttca gcgtcgcctg aatccgttac catttgtttg ttgtttgtat cgaatcggac    2700
ggcgaagatt gcatcgcgag gtattatgca gcagagtgat caaacggtgt tgagcttgag    2760
gcccggtggt ggaagaggca gcaggctcct cgctcctcga tccgactcct cctcttcgtc    2820
ctctgcttcc cctgcttttg gctccttttc cgctgatctt cctctcctgc gtccccacgc    2880
tggagctccc tctcccttct ctatcaaagt atcaatccct tttccctgga tctgcctttt    2940
tacctcttta attcgccctt tttttatgt ttgctgtttg ctttatgtcg attgatgctt     3000
ggatggattc tgtttcatga atacgtgttt ttttttcttt cgttattttg atttgtgata    3060
gcttgttatt atgtgtgttt cttaaatatt tttcttttgt atattcttaa cttgatgaat    3120
atcaccgagg ctcaatgtga cgtttttttt tttccttttt aaagtttaaa atttgaggtg    3180
aggtgtattg tgctgaagtt tggattcgga ataatccgt ttttggtctt cattgacact     3240
cggggatttt tttgtgtgtg tgtttgtttg tccaatacgc agatttgaat gttgtctgga    3300
tttgctggtg gtgtattttg gaatttaatt acttaactaa ttttttggc accattttaa     3360 acgtaaagag aaaccttcag aagaatcgac taaccgaaac taaacaaat aaagatgtaa     3420 tgtatttctc gttgttactg tctttttttt ttttgccttc caaaaaaaaa aactgtcttt    3480
ttttttttca ctgtctataa gtattcaagt taagggcata agacaaaggg caaactgaat    3540
```

```
tcgaatgtcc taattcttgg ctgggcacta agtgtgtgca cctgctgtaa atatggacaa    3600
aaagcaatat gttggcttta ggtggaattg actgaatttc aagttaccca taaaggtccc    3660
acatacattg aacttcattt cacaattctg gtgaatgtgt caacttcttt gtggcacagg    3720
atctgatatc gttttcttag tacactggtc tctgcatttt tcttaatggg gcattcatcc    3780
acatttcaca gtgactagta ttgtttggca ctgtgtttcc acctcctgga tacggtgctt    3840
gagtggttgt gataagtctt atgctttttt gttctgaagg caatgctgca aaggccacaa    3900
atctgttcag ttgttctgtt ttttggttgt gttgtaaatc cgttgacata acaatataaa    3960
tgagtttgtt ggatccactg gttgcctata gagaagagta catgtataat gttgtatcaa    4020
cactgtagtt catgaaggac atgtctgaaa acaattatt tataactatt ttaactgtga    4080
tgttcgtgtg tagaacttag tttcattgaa ttctacctt ctttttagcac tacttatgat    4140 cttatgcatc tacctatgac ccatcttgta cttttctgaa tttatctgct tgaatggtga    4200
tggtttaact gtatatgtca aggaatttgt atctaaaaac ttatggcttt ataggctgga    4260
gatgctcggt ttgagggccg tgagcgtgtg cgatacacaa gggaacagct tttacagctt    4320
aaagaggtaa ttttttttgt tgttgttgtt taaatgttat tgctaattaa ttatacttat    4380
tccgaaggat attttttaa ttccatcttc tgctttacat gtgattcttt tcctattaat    4440
ttggaaattg tgactaatca acattgcctg tgtgtgtaga ttgccttgtg tttgtattgt    4500
tttaatttac tcacattact aaatagaag gtgccaaatt ttctattgaa ctctctcgac    4560 aacctactt attctctatg cctcttgata aatgtttgac atatttttt aaatatcttt    4620 tgtctcttct ctctaggcaa cttcttttga aaaaccatgt gttccagttt ttgcaactaa    4680
tacttccttt gacatctaag ctgatattta tgcttcatca tttgtctgac tgttgaacct    4740
ttttactctt agggtgttga gatcctcgat gatgttttaa agatcaaaca agatattgaa    4800
gctgaacttt ttggtgaaga tcaaagttgg gcccgcccag aaaacaacgt gagtgcgttc    4860
tgtcttgtat ttatgtcgtt gttaactaag accctattcc tcctcatcct gttggtaaag    4920
tgatcgatga agtttattag agtttatttt ttttggcggt gaacatacta ttatcttaca    4980
ggaattcatc agtgatcagt taatggaaat agtctaatgt ttgtacaaga tgctgctttt    5040
tttattattt tgattagttc aattaaattg tatcaatttt tatgaattta tttgtgatca    5100
ttatcaaaat aataagttca actattcaaa ttttgtctaa tgatgtgtat actatattct    5160
gcagcccaca cagcaatttc aaaatcgata tactgagcca gataatcgtg actggcgtgg    5220
aagatctggc caactttctg gtaatgcaga tgagaggtct tgggataatc tcaaggagaa    5280
tagggagttt ggcaatacta gtaatcgtca agaccaactg aactctcagt ttgcaaggac    5340
acaaatctct tctaaccaag gggtactaat aattggcaga aatgcatgat atccattttg    5400
tagttaatgt tttatatctt taaatttgat ccagtgtcag tgtaaaactc tttacattat    5460
cattaaagtg attaaacaag aaagtgttac accattataa taacaaagga tttccttgaa    5520
gtaaaagttt tatgagcttt taataggtgg aactgaatgg ttctctcata gtgtacaatg    5580
gataagtgtt ttatcttatt ttttattttt atttcttcta tctctattaa ttcagggagg    5640
acctactccg acactagtca aggctgaggt gccatggtca gctagaaggg gaactctctc    5700
tgacaaggat cgcgtcctaa agacagttaa agggtaatat atatttattt tcgagtactt    5760
gttagttgtt aatagtttaa tggggatatc ctccttgactt taatctcttg tagattcctg    5820
gatggtcatg cattcctagg tcttaacaat cattacggta ttcttaatgg ctaaatgaga    5880
```

-continued

```
aatacaagca acatatttca acacaccctt tattatttgg tgaatttcat acaggtccca   5940
tttgatttag gcaggtctta tgaatttcac ccaataataa agagtgcatc aaaaaagtat   6000
gttgacaagt aaatgtaaca agttgtaatg aagaacattt tgtgggatat gctatattat   6060
ttgtggactt ggctcctcta aattgataaa atatataagg tgagaaagta aggtgtgtct   6120
actgttgatt tgaattagat ttgaattaaa gcacttcaaa aacttacccc tcttaaacca   6180
agagtagata catccttaaa atttctcact ttacatagga gttaaatctg tgaaaaataa   6240
ccataattca atatttgtga gttgtgacaa gattgatgta tctattcttt ttcctgtata   6300
aactgagatt gaagtatttt ttgaacattt tttgtatttc cttcactcat gtaactctgt   6360
taagaatctt caaaattaca tggctcctga tactaataca ccaagtatgg ttaaccattt   6420
caatgcagaa tactaaataa gttgactccg gagaaatttg atctcctgaa gggtcagttg   6480
atcgattctg gcattacatc agccgacata ttgaaggttc attttattgt gttaaaaata   6540
tttttctgtt catatctttg ttcttaattg acttggtttg aaatgcaggg agttatttcg   6600
ctgatatttg ataaggcagt gctggaacca acattttgcc ccatgtatgc tcagctgtgt   6660
tctgatctta tgaaaagct gcctccattc ccatctgacg agcctggtgg gaaagaaatc   6720
acttttaagc gagtactctt gaatatctgc caggaggctt tgaaggtgc agataaactg   6780
agggaagaac tgagacagat gactgccccct gaccaggaga tggagcgacg ggacaaggaa   6840
agacttgtca agattcgaac ccttggaaat atccgtttaa ttggtgagct gttgaagcaa   6900
aaaatggttc ccgaaaagat tgttcatcac attgttcagg ttcaatcagg acttgagact   6960
tgactttgat ataatttcct attggtttgg gagtatgcac ttatctgcat ggttgactga   7020
tacttggaac aggagctttt aggacctcca gacatcaagg tctgtccagc tgaggaaaat   7080
gttgaagcca tatgtcagtt tttcaacact attggtaagc agcttgatga aagcccaaaa   7140
tcacggcgca taaatgatat gtactttatc cggttgaaag aattgagcac caatccccaa   7200
cttgcaccac ggctgcggtt tatggttcgt gatgttctag atttgcgttc taataactgg   7260
attccaagac gtgaagaggc aaatttacac attttgtaaa taagctatgc ctcaaatttt   7320
ggaaggtact tcaatttttt tttttaatg aagtactaat cttactcat gtaggtgaaa   7380
gccaaaacca tcactgaaat tcattcagag gcagaaaaaa atcttggatt gcgtccaggt   7440
gccactgcaa gtatgagaaa taaccgtgta gtttcaggcg ctctaggaaa taccagtcca   7500
ggaggattcc caattgctcg acctggtaca ggtggtttga tgccagggat gccagggacc   7560
aggaggatgc ctgggatgcc tgaattgat aatgacaact gggagatgcc taagacaaga   7620
tcaatgccga gaggagacat gtcaggcatg caaactggag gacatagcca gtcccccttt   7680
cttttccaaga catccactgt taactctagg ttactacctc aaggtagtgg tggtattata   7740
agtgggagaa gcagtgccct ggtgcatgga gctggtgctc cttctgctgc tcggccacca   7800
aaccttggtt ttagtgctga acccacacct caaatccctt cacctgttaa agcggtttct   7860
gccatacccg ctgagaagcc acaacctcca gctgcaaaat tgaattttga tgaacttcag   7920
cgtaaaactg tttctcttct ggaagaatat ttcaatgtcc ggcttttgga cgaggcatta   7980
cagtgtgtgg aggaactaaa agctccagct tattaccctg agtttgtcaa ggaagctatt   8040
tcccttgctc tagataaaag tccgccatgc gctgaacctg tcgccaatct tttgaatat   8100
ctgttcatta agaagattct ttcagccaga gacatagga ctgggtgcat gttatttgct   8160
tctctgctgg atgatatcgg catagattta cctaaagcac caaataattt tggtgagata   8220
ataggggaaac tagttttggc tgggggtttg gatttaagg tggtgacaga aatccttaag   8280
```

-continued

| | |
|---|---|
| aaggtggagg atgaccggtt ccagaaagca atatttctt ctgcgttgca ggtaattacc | 8340 |
| tctgcatctg gcaagctgt gttggatgca caagcatctg atattgaggc ctgccagagt | 8400 |
| ctgttcaact ga | 8412 |

<210> SEQ ID NO 9
<211> LENGTH: 8432
<212> TYPE: DNA
<213> ORGANISM: Glycine max

<400> SEQUENCE: 9

| | |
|---|---|
| taagctcaac tctaaacaaa aaacaaggac atttggaaga gttttactga gcctcgtgct | 60 |
| ggacaccata atgttatatt gatagagtga aaataaatga aagaaaacg aattgaaata | 120 |
| aaagttttga attaaattag agtgaaaaag tgtaaatttt atcttatttt actgtttatt | 180 |
| ttatttcttt ttcattcttt ttccactcaa aggaacagac acttagagat tgtccaacga | 240 |
| aattttatgg ctagttcatt caagtgtgtt aagactttct ttttaaatgc taaaagaatt | 300 |
| tagacttaag ctatttggtg gttatccaaa tggtaagaga taatatatct ttgtgtttgt | 360 |
| ggcctctagt ttggtactta tttttcaagg catacaataa gggttaactt ggtatatcac | 420 |
| atgttaagtt aaaaggtcca atgttgtttg gttgaggttt caattaagtt agtctcataa | 480 |
| ttttcccgac aaattgattc aatacaagca taatttgaaa ctcaaactca aacttgacca | 540 |
| taaagctaaa tcaaaaacca taagtgtac tcttatgcat gattaaatta ccataaatag | 600 |
| aagaaaataa atattaatat taaaaaattc attcaaattt cattaacagc aggttagtca | 660 |
| caaccccacc cattttctat ttatattaag tatacttttc tcactttaaa aataacaat | 720 |
| gtttacttat gtggtggttc ctatagttat acaatctta cattttagcc tttacaccta | 780 |
| aaacctactt gttttagtca ttatacatat attttaatt tgttttggtc tacacatttc | 840 |
| cttttaatt cagtttaatc aatacaatac aattccagac gatgaaaga ttaaaacaaa | 900 |
| tttaaaagtg ttagaagata agaaaattga tattactttt ctctaattat ctaaggatga | 960 |
| aattattgat tgtgggagt tgctattggc ccctaaaaat atgagaaaaa acattcttac | 1020 |
| cctccctctt ccctcgcct tcttctcacc ccacccaacc catcaccact gcaccaacga | 1080 |
| cgccatcacc gtcacctcct ctgtccatat ttgaactagc gaccccaatg ttgttgtagc | 1140 |
| aacattccaa caatggcatg tgccactctc gaccaccacg ccgttgcaac attgtgcaac | 1200 |
| cccctttgat cctacatatt tgttcatatt gttgcgtgtt tttcatcgtc gctatgatca | 1260 |
| aacaccctaa atatgcatca acttagaccc atcaacccag atcttcacca ccaccatcaa | 1320 |
| atttatccta ttcaaaggaa gaaaagagg gaaacaaaag catagtccca ttttgggtaa | 1380 |
| aaaacaatag tagaatcaca attttgttgt gttatttc ttgtatccct tttagaaagc | 1440 |
| aatgaaaagc atgatttcat tgtacaatgt gcagcgtaat tgtgtttcca ttatttttt | 1500 |
| tgcaccccctt cataaaacaa cgaaaacaca atttcattgt aaaaaaaatt gtgttttcgt | 1560 |
| tatttttttt tgtaccccctt cgtaaaataa caaaaatatg attttttttt cttgcatccc | 1620 |
| atttagaaag caacaaaaaa cacaaaattg ttgtacaatt tgtaacacaa tcatgtttcc | 1680 |
| attattttt tcttgcaccc tctgaaaaaa acaacgaaaa cccaatttca tcgtataatg | 1740 |
| aaatcatgtt tcatgaaaa aagtaaaaaa aatattgtta acccccttaat agggggccaat | 1800 |
| agcaaaggag ttgaggccaa taactaactc ttttttttt gggggtacaa tggtcgcatt | 1860 |
| aagatttgaa tttatgaaaa tacaaaatat tataaaaaat ctaaacctgt aatggtacat | 1920 |

```
tgagttactt ttttatttgt tttgaaatta ttataaaaat acaaaatata cctgttaagc    1980
aaaaagagca atcttcttct cgttatatct ctacagtggg ccgtggcttg gccgcccagc    2040
ccacacgcat ttaagcctgg atgcctgcgt gtatatccat ctatattttc gacaaaaaac    2100
actatatgct atatgatata tggtatatac tatatactat tcagtataca aagactttt     2160 cttcaaaaaa aaaaattcag tatacaaaga ggcagagaca ggcaaaaata tattttgta     2220 tttatatgat tcggtgatta gatttcatta gaacgaaatt atgtcctcaa taatcccaat    2280
tccaagtact gtcgaagata taaggtaat aacaaccgac catgggcaaa tgtcaatttc     2340
ctgtttctgt tggggtgtcc gaagaaataa ttaaaatata atattgggcg agatttgaaa    2400
tacgtataga tacggtaggc tacgacataa cacaactcgt ctaagaaggg ttttttgtca    2460
cccctccgtt gtttctcact cactcacgca cgcagtactc tcttttcttc tcactccgca    2520
gaagagagag aaatatccaa tacctagcgt tagcgtactc tctcccaatc ccaatccttt    2580
tttctctcta tctatctatt catcccttc tcttcttctt ctattccctc ttctccttcc     2640
gcttctcctc tttatcgctg ttgtggttca gcgtcgcctg aatccgttac catttgtttg    2700
ttgtttgtat cgaatcggac ggcgaagatt gcatcgcgag gtattatgca gcagagtgat    2760
caaacggtgt tgagcttgag gcccggtggt ggaagaggca gcaggctcct cgctcctcga    2820
tccgactcct cctcttcgtc ctctgcttcc cctgcttttg gctccttttc cgctgatctt    2880
cctctcctgc gtcccacgc tggagctccc tctcccttct ctatcaaagt atcaatccct    2940
tttccctgga tctgcctttt tacctcttta attcgccctt ttttttatgt ttgctgtttg    3000
ctttatgtcg attgatgctt ggatggattc tgtttcatga atacgtgttt tttttctctt    3060 cgttatttg atttgtgata gcttgttatt atgtgtgttt cttaaatatt tttcttttgt     3120
atattcttaa cttgatgaat atcaccgagg ctcaatgtga cgttttttt tttccttttt     3180 aaagtttaaa atttgaggtg aggtgtattg tgctgaagtt tggattcgga aataatccgt    3240
ttttggtctt cattgacact cggggatttt tttgtgtgtg tgtttgtttg tccaatacgc    3300
agatttgaat gttgtctgga tttgctggtg gtgtatttg gaatttaatt acttaactaa    3360 ttttttttggc accatttta acgtaaagag aaaccttcag aagaatcgac taaccgaaac    3420
taaaacaaat aaagatgtaa tgtatttctc gttgttactg tcttttttt ttttgccttc    3480 caaaaaaaaa aactgtcttt ttttttttca ctgtctataa gtattcaagt taagggcata    3540
agacaaaggg caaactgaat tcgaatgtcc taattcttgg ctgggcacta agtgtgtgca    3600
cctgctgtaa atatggacaa aaagcaatat gttggcttta ggtggaattg actgaatttc    3660
aagttaccca taaaggtccc acatacattg aacttcattt cacaattctg gtgaatgtgt    3720
caacttcttt gtggcacagg atctgatatc gttttcttag tacactgtc tctgcatttt     3780 tcttaatggg gcattcatcc acatttcaca gtgactagta ttgtttggca ctgtgtttcc    3840
acctcctgga tacggtgctt gagtggttgt gataagtctt atgctttttt gttctgaagg    3900
caatgctgca aaggccacaa atctgttcag ttgttctgtt ttttggttgt gttgtaaatc    3960
cgttgacata acaatataaa tgagtttgtt ggatccactg gttgcctata gagaagagta    4020
catgtataat gttgtatcaa cactgtagtt catgaaggac atgtctgaaa acaattatt     4080 tataactatt ttaactgtga tgttcgtgtg tagaacttag tttcattgaa ttctacctt     4140 cttttagcac tacttatgat cttatgcatc tacctgatgac ccatcttgta cttttctgaa    4200
tttatctgct tgaatggtga tggtttaact gtatatgtca aggaatttgt atctaaaaac    4260
ttatggcttt ataggctgga gatgctcggt ttgagggccg tgagcgtgtg cgatacacaa    4320
```

```
gggaacagct tttacagctt aaagaggtaa tttttttttgt tgttgttgtt taaatgttat   4380
tgctaattaa ttatacttat tccgaaggat atttttttaa ttccatcttc tgctttacat   4440
gtgattcttt tcctattaat ttggaaattg tgactaatca acattgcctg tgtgtgtaga   4500
ttgccttgtg tttgtattgt tttaatttac tcacattact taaatagaag gtgccaaatt   4560
ttctattgaa ctctctcgac aacctacttt attctctatg cctcttgata aatgtttgac   4620
atattttttt aaatatcttt tgtctcttct ctctaggcaa cttcttttga aaaccatgt    4680 gttccagttt ttgcaactaa tacttccttt gacatctaag ctgatattta tgcttcatca   4740
tttgtctgac tgttgaacct ttttactctt agggtgttga gatcctcgat gatgttttaa   4800
agatcaaaca agatattgaa gctgaacttt ttggtgaaga tcaaagttgg gcccgcccag   4860
aaaacaacgt gagtgcgttc tgtcttgtat ttatgtcgtt gttaactaag acctattcc    4920 tcctcatcct gttggtaaag tgatcgatga agtttattag agtttatttt ttttggcggt   4980
gaacatacta ttatcttaca ggaattcatc agtgatcagt taatggaaat agtctaatgt   5040
ttgtacaaga tgctgctttt tttattattt tgattagttc aattaaattg tatcaatttt   5100
tatgaattta tttgtgatca ttatcaaaat aataagttca actattcaaa ttttgtctaa   5160
tgatgtgtat actatattct gcagcccaca cagcaatttc aaaatcgata tactgagcca   5220
gataatcgtg actggcgtgg aagatctggc caactttctg gtaatgcaga tgagaggtct   5280
tgggataatc tcaaggagaa tagggagttt ggcaatacta gtaatcgtca agaccaactg   5340
aactctcagt ttgcaaggac acaaatctct tctaaccaag gggtactaat aattggcaga   5400
aatgcatgat atccattttg tagttaatgt tttatatctt taaatttgat ccagtgtcag   5460
tgtaaaactc tttacattat cattaaagtg attaaacaag aaagtgttac accattataa   5520
taacaaagga tttccttgaa gtaaagttt tatgagcttt taataggtgg aactgaatgg   5580
ttctctcata gtgtacaatg gataagtgtt ttatcttatt tttttattttt atttcttcta   5640 tctctattaa ttcagggagg acctactccg acactagtca aggctgaggt gccatggtca   5700
gctagaaggg gaactctctc tgacaaggat cgcgtcttaa agacagttaa agggtaaatat  5760 atatttattt tcgagtactt gttagttgtt aatagtttaa tggggatatc ctcttgactt   5820
taatctcttg tagattcctg gatggtcatg cattcctagg tcttaacaat cattacggta   5880
ttcttaatgg ctaaatgaga aatacaagca acatatttca acacacccctt tattatttgg   5940 tgaatttcat acaggtccca tttgatttag gcaggtctta tgaatttcac ccaataataa   6000
agagtgcatc aaaaaagtat gttgacaagt aaatgtaaca agttgtaatg aagaacattt   6060
tgtgggatat gctatattat ttgtggactt ggctcctcta aattgataaa atatataagg   6120
tgagaaagta aggtgtgtct actgttgatt tgaattagat ttgaattaaa gcacttcaaa   6180
aacttaaccc tcttaaacca agagtagata catccttaaa atttctcact ttacatagga   6240
gttaaatctg tgaaaaataa ccataattca atatttgtga gttgtgacaa gattgatgta   6300
tctattcttt ttcctgtata aactgagatt gaagtatttt ttgaacattt tttgtatttc   6360
cttcactcat gtaactctgt taagaatctt caaaattaca tggctcctga tactaataca   6420
ccaagtatgg ttaaccattt caatgcagaa tactaaataa gttgactccg gagaaatttg   6480
atctcctgaa gggtcagttg atcgattctg gcattacatc agccgacata ttgaaggttc   6540
attttattgt gttaaaaata ttttttctgtt catatctttg ttcttaattg acttggtttg   6600
aaatgcaggg agttatttcg ctgatatttg ataaggcagt gctggaacca acattttgcc   6660
```

```
ccatgtatgc tcagctgtgt tctgatctta atgaaaagct gcctccattc ccatctgacg    6720
agcctggtgg gaaagaaatc acttttaagc gagtactctt gaatatctgc caggaggctt    6780
ttgaaggtgc agataaactg agggaagaac tgagacagat gactgcccct gaccaggaga    6840
tggagcgacg ggacaaggaa agacttgtca agattcgaac ccttggaaat atccgtttaa    6900
ttggtgagct gttgaagcaa aaaatggttc ccgaaaagat tgttcatcac attgttcagg    6960
ttcaatcagg acttgagact tgactttgat ataatttcct attggtttgg gagtatgcac    7020
ttatctgcat ggttgactga tacttggaac aggagctttt aggacctcca gacatcaagg    7080
tctgtccagc tgaggaaaat gttgaagcca tatgtcagtt tttcaacact attggtaagc    7140
agcttgatga aagcccaaaa tcacggcgca taaatgatat gtactttatc cggttgaaag    7200
aattgagcac caatccccaa cttgcaccac ggctgcggtt tatggttcgt gatgttctag    7260
atttgcgttc taataactgg attccaagac gtgaagaggt aaatttacac attttgtaaa    7320
taagctatgc ctcaaatttt ggaaggtact tcaattttt ttttttaatg aagtactaat    7380
ctttactcat gtaggtgaaa gccaaaacca tcactgaaat tcattcagag gcagaaaaaa    7440
atcttggatt gcgtccaggt gccactgcaa gtatgagaaa taaccgtgta gtttcaggcg    7500
ctctaggaaa taccagtcca ggaggattcc caattgctcg acctggtaca ggtggtttga    7560
tgccagggat gccagggacc aggaggatgc ctgggatgcc tggaattgat aatgacaact    7620
gggagatgcc taagacaaga tcaatgccga gaggagacat gtcaggcatg caaactggag    7680
gacatagcca gtctcccttt ctttccaaga catccactgt taactctagg ttactacctc    7740
aaggtagtgg tggtattata agtgggagaa gcagtgccct ggtgcatgga gctggtgctc    7800
cttctgctgc tcggccacca aaccttggtt ttagtgctga acccacacct caaatcccttt   7860 cacctgttaa agctgtttct gccatacccg ctgagaagcc acaacctcca gctgcaaaat    7920
tgaattttga tgaacttcag cgtaaaactg tttctcttct ggaagaatat ttcaatgtcc    7980
ggcttttgga cgaggcatta cagtgtgtgg aggaactaaa agctccagct tattaccctg    8040
agtttgtcaa ggaagctatt tcccttgctc tagataaaag tccgccatgc gctgaacctg    8100
ttgccaatct tttgaatat ctgttcatta agaagattct ttcagccaga gacataggga    8160
ctgggtgcat gttatttgct tctctgctgg atgatatcgg catagattta cctaaagcac    8220
caaataattt tggtgagata tagggaaac tagttttggc tgggggttttg attttaaggg   8280 tggtgacaga atccttaag aaggtggagg atgaccggtt ccagaaagca atattttctt    8340
ctgcgttgca ggtaattacc tctgcatctg ggcaagctgt gttggatgca caagcatctg    8400
atattgaggc ctgccagagt ctgttcaact ga                                  8432

<210> SEQ ID NO 10
<211> LENGTH: 9000
<212> TYPE: DNA
<213> ORGANISM: Glycine max

<400> SEQUENCE: 10
aaaaacaagg acatttggaa gagttttact gagcctcgtg ctggacacca taatgttata     60
ttgatagagt gaaataaat gaaagaaaa cgaattgaaa taaagttttt gaattaaatt     120
agagtgaaaa agtgtaaatt ttatcttatt ttactgttta ttttattttct ttttcattct    180 ttttccactc aaaggaacag acacttagag attgtccaac gaaatttat ggctagttca    240 ttcaagtgtg ttaagacttt cttttaaat gctaaaagaa tttagactta agctatttgg    300
tggttatcca aatggtaaga gataatatat ctttgtgttt gtggcctcta gtttggtact    360
```

```
tattttttcaa ggcatacaat aagggttaac ttggtatatc acatgttaag ttaaaaggtc    420
caatgttgtt tggttgaggt ttcaattaag ttagtctcat aattttcccg acaaattgat    480
tcaatacaag cataatttga aactcaaact caaacttgac cataaagcta atcaaaaac     540 cataaagtgt actcttatgc atgattaaat taccataaat agaagaaaat aaatattaat    600
attaaaaaat tcattcaaat ttcattaaca gcaggttagt cacaacccca cccatttcct    660
atttatatta agtatacttt tctcactta aaaataaca atgtttactt atgtggtggt      720
tcctatagtt atacaatctt tacatttag cctttacacc taaaacctac ttgttttagt     780
cattatacat atatttttaa tttgttttgg tctacacatt tcctttttaa ttcagtttaa    840
tcaatacaat acaattccag acgatgaaaa gattaaaaca aatttaaaag tgttagaaga    900
taagaaaatt gatattactt ttctctaatt atctaaggat gaaattattg attgtgggga    960
gttgctattg gcccctaaaa atatgagaaa aaacattctt accctccctc ttcccctcgc   1020
cttcttctca ccccacccaa cccatcacca ctgcaccaac gacgccatca ccgtcacctc   1080
ctctgtccat atttgaacta gcgaccccaa tgttgttgta gcaacattcc aacaatggca   1140
tgtgccactc tcgaccacca cgccgttgca acattgtgca accccttgat cctacatatt   1200
tgttcatatt gttgcgtgtt ttcatcgtcg ctatgatcaa acaccctaga tatgcatcaa   1260
cttagaccca tcaacccaga tcttcaccac caccatcaaa tttatcctat tcaaaggaag   1320
aaaaagaggg aaacaaaagc atagtcccat tttgggtaaa aacaatagt agaatcacaa    1380 ttttgttgtg ttattttttct tgtatcccctt ttagaaagca atgaaaagca tgatttcatt   1440
gtacaatgtg cagcgtaatt gtgtttccat tatttttttt gcacccctttc ataaaacaac   1500 gaaaacacaa tttcattgta aaaaaaattg tgttttcgtt attttttttt gtaccccttc    1560
gtaaaataac aaaaatatga ttttttttc ttgcatccca tttagaaagc aacaaaaaac    1620
acaaaattgt tgtacaattt gtaacacaat catgtttcca ttattttttt cttgcaccct   1680
ctgaaaaaaa caacgaaaac acaatttcat cgtataatga aatcatgttt tcatgaaaaa   1740
agtaaaaaaa atattgttaa ccccttaata gggaccaata gcaaaggagt tgaggccaat   1800
aactaactct tttttttttg ggggtacaat ggtcgcatta agatttgaat ttatgaaaat   1860 acaaatatt ataaaaaatc taaacctgta atggtacatt gagttacttt tttatttgtt    1920
ttgaaattat tataaaaata caaatatac ctgttaagca aaaagagcaa tcttcttctc     1980
gttatatctc tacagtgggc cgtggcttgg ccgcccagcc cacacgcatt taagcctgga   2040
tgcctgcgtg tatatccatc tatattttcg acaaaaaaca ctatatgcta tatgatatat   2100
ggtatatact atatactatt cagtatacaa agacttttttc ttcaaaaaaa aaaattcagt   2160
atacaaagag gcagagacag gcaaaaatat atttttgtat ttatatgatt cggtgattag   2220
atttcattag aacgaaatta tgtcctcaat aatcccaatt ccaagtactg tcgaagataa   2280
taaggtaata caaccgacc atgggcaaat gtcaatttcc tgtttctgtt ggggtgtccg    2340
aagaaataat taaaatataa tattgggcga gatttgaaat acgtatagat acggtaggct   2400
acgacataac acaactcgtc taagaagggt tttttgtcac ccctccgttg tttctcactc   2460
actcacgcac gcagtactct cttttcttct cactccgcag aagagagaga aatatccaat   2520
acctagcgtt agcgtactct ctcccaatcc caatccttt ttctctctat ctatctattc     2580
atccctttct cttcttcttc tattccctct tctccttccg cttctcctct ttatcgctgt   2640
tgtggttcag cgtcgcctga atccgttacc atttgtttgt tgtttgtatc gaatcggacg   2700
```

```
gcgaagattg catcgcgagg tattatgcag cagagtgatc aaacggtgtt gagcttgagg    2760
cccggtggtg gaagaggcag caggctcctc gctcctcgat tcgactcctc ctcttcgtcc    2820
tctgcttccc ctgcttttgg ctccttttcc gctgatcttc ctctcctgcg tccccacgct    2880
ggagctccct ctcccttctc tatcaaagta tcaatccctt ttccctggat ctgcctttt     2940 acctctttaa ttcgcccttt tttttatgtt tgctgtttgc tttatgtcga ttgatgcttg    3000
gatggattct gtttcatgaa tacgtgtttt ttttcttttc gttatttga  tttgtgatag    3060 cttgttatta tgtgtgtttc ttaaatattt ttcttttgta tattcttaac ttgatgaata    3120
tcaccgaggc tcaatgtgac gttttttttt ttccttttta aagtttaaaa tttgaggtga    3180
ggtgtattgt gctgaagttt ggattcggaa ataatccgtt tttggtcttc attgacactc    3240
ggggattttt ttgtgtgtgt gtttgtttgt ccaatacgca gatttgaatg ttgtctggat    3300
ttgctggtgg tgtattttgg aatttaatta cttaactaat tttttggca ccattttaaa     3360 cgtaaagaga aaccttcaga agaatcgact aaccgaaact aaaacaaata aagatgtaat    3420
gtatttctcg ttgttactgt cttttttttt tttgccttcc aaaaaaaaaa actgtctttt    3480
tttttttcac tgtctataag tattcaagtt aagggcataa acaaagggc  aaactgaatt    3540 cgaatgtcct aattcttggc tgggcactaa gtgtgtgcac ctgctgtaaa tatggacaaa    3600
aagcaatatg ttggctttag gtggaattga ctgaatttca agttacccat aaaggtccca    3660
catacattga acttcatttc acaattctgg tgaatgtgtc aacttctttg tggcacagga    3720
tctgatatcg ttttcttagt acactggtct ctgcattttt cttaatgggg cattcatcca    3780
catttcacag tgactagtat tgtttggcac tgtgtttcca cctcctggat acggtgcttg    3840
agtggttgtg ataagtctta tgctttttg  ttctgaaggc aatgctgcaa aggccacaaa    3900
tctgttcagt tgttctgttt tttggttgtg ttgtaaatcc gttgacataa caatataaat    3960
gagtttgttg gatccactgg ttgcctatag agaagagtac atgtataatg ttgtatcaac    4020
actgtagttc atgaaggaca tgtctgaaaa acaattattt ataactattt taactgtgat    4080
gttcgtgtgt agaacttagt ttcattgaat tctacctttc ttttagcact acttatgatc    4140
ttatgcatct acctatgacc catcttgtac ttttctgaat ttatctgctt gaatggtgat    4200
ggtttaactg tatatgtcaa ggaatttgta tctaaaaact tatggcttta taggctggag    4260
atgctcggtt tgagggccgt gagcgtgtgc gatacacaag ggaacagctt ttacagctta    4320
aagaggtaat ttttttttgtt gttgttgttt aaatgttatt gctaattaat tatacttatt   4380
ccgaaggata tttttttaat tccatcttct gctttacatg tgattctttt cctattaatt    4440
tggaaattgt gactaatcaa cattgcctgt gtgtgtagat tgccttgtgt ttgtattgtt    4500
ttaatttact cacattactt aaatagaagg tgccaaattt tctattgaac tctctcgaca    4560 acctactta  ttctctatgc ctcttgataa atgtttgaca tatttttta  aatatctttt    4620 gtctcttctc tctaggcaac ttcttttgaa aaaccatgtg ttccagtttt tgcaactaat    4680
acttcctttg acatctaagc tgatatttat gcttcatcat ttgtctgact gttgaacctt    4740
tttactctta gggtgttgag atcctcgatg atgttttaaa gatcaaacaa gatattgaag    4800
ctgaactttt tggtgaagat caagttggg  cccgcccaga aaacaacgtg agtgcgttct    4860
gtcttgtatt tatgtcgttg ttaactaaga cccgtattcct cctcatcctg ttggtaaagt   4920
gatcgatgaa gtttattaga gtttattttt tttggcggtg aacatactat tatcttacag    4980
gaattcatca gtgatcagtt aatggaaata gtctaatgtt tgtacaagat gctgcttttt    5040
ttattatttt gattagttca attaaaattgt atcaattttt atgaatttat ttgtgatcat   5100
```

```
tatcaaaata ataagttcaa ctattcaaat tttgtctaat gatgtgtata ctatattctg   5160
cagcccacac agcaatttca aaatcgatat actgagccag ataatcgtga ctggcgtgga   5220
agatctggcc aactttctgg taatgcagat gagaggtctt gggataatct caaggagaat   5280
agggagtttg gcaatactag taatcgtcaa gaccaactga actctcagtt tgcaaggaca   5340
caaatctctt ctaaccaagg ggtactaata attggcagaa atgcatgata tccattttgt   5400
agttaatgtt ttatatcttt aaatttgatc cagtgtcagt gtaaaactct ttacattatc   5460
attaaagtga ttaaacaaga aagtgttaca ccattataat aacaaggat tccttgaag   5520 taaaagtttt atgagctttt aataggtgga actgaatggg tctctcatag tgtacaatgg   5580
ataagtgttt tatcttattt tttatttta tttcttctat ctctattaat tcagggagga   5640
cctactccga cactagtcaa ggctgaggtg ccatggtcag ctagaagggg aactctctct   5700
gacaaggatc gcgtcttaaa gacagttaaa gggtaatata tatttatttt cgagtacttg   5760
ttagttgtta atagtttaat ggggatatcc tcttgacttt aatctcttgt agattcctgg   5820
atggtcatgc attcctaggt cttaacaatc attacggtat tcttaatggc taaatgagaa   5880
atacaagcaa catatttcaa cacacccttt attatttggt gaatttcata caggtcccat   5940
ttgatttagg caggtcttat gaatttcacc caataataaa gagtgcatca aaaaagtatg   6000
ttgacaagta aatgtaacaa gttgtaatga agaacatttt gtgggatatg ctatattatt   6060
tgtggacttg gctcctctaa attgataaaa tatataaggt gagaaagtaa ggtgtgtcta   6120
ctgttgattt gaattagatt tgaattaaag cacttcaaaa acttaaccct cttaaaccaa   6180
gagtagatac atccttaaaa tttctcactt tacataggag ttaaatctgt gaaaaataac   6240
cataattcaa tatttgtgag ttgtgacaag attgatgtat ctattctttt tcctgtataa   6300
actgagattg aagtattttt tgaacatttt ttgtatttcc ttcactcatg taactctgtt   6360
aagaatcttc aaaattacat ggctcctgat actaatacac caagtatggt taaccatttc   6420
aatgcagaat actaaataag ttgactccgg agaaatttga tctcctgaag ggtcagttga   6480
tcgattctgg cattacatca gccgacatat tgaaggttca ttttattgtg ttaaaaatat   6540
ttttctgttc atatctttgt tcttaattga cttggtttga aatgcaggga gttatttcgc   6600
tgatatttga taaggcagtg ctggaaccaa cattttgccc catgtatgct cagctgtgtt   6660
ctgatcttaa tgaaaagctg cctccattcc catctgacga gcctggtggg aaagaaatca   6720
cttttaagcg agtactcttg aatatctgcc aggaggcttt tgaaggtgca gataaactga   6780
gggaagaact gagacagatg actgcccctg accaggagat ggagcgacgg gacaaggaaa   6840
gacttgtcaa gattcgaacc cttggaaata tccgtttaat tggtgagctg ttgaagcaaa   6900
aaatggttcc cgaaaagatt gttcatcaca ttgttcaggt tcaatcagga cttgagactt   6960
gactttgata taatttccta ttggtttggg agtatgcact tatctgcatg gttgactgat   7020
acttggaaca ggagctttta ggacctccag acatcaaggt ctgtccagct gaggaaaatg   7080
ttgaagccat atgtcagttt ttcaacacta ttggtaagca gcttgatgaa agcccaaaat   7140
cacggcgcat aaatgatatg tactttatcc ggttgaaaga attgagcacc aatccccaac   7200
ttgcaccacg gctgcggttt atggttcgtg atgttctaga tttgcgttct aataactgga   7260
ttccaagacg tgaagaggta aatttacaca ttttgtaaat aagctatgcc tcaaattttg   7320
gaaggtactt caatttttttt tttttaatga agtactaatc tttactcatg taggtgaaag   7380
ccaaaaccat cactgaaatt cattcagagg cagaaaaaaa tcttggattg cgtccaggtg   7440
```

-continued

```
ccactgcaag tatgagaaat aaccgtgtag tttcaggcgc tctaggaaat accagtccag    7500
gaggattccc aattgctcga cctggtacag gtggtttgat gccagggatg ccagggacca    7560
ggaggatgcc tgggatgcct ggaattgata atgacaactg ggagatgcct aagacaagat    7620
caatgccgag aggagacatg tcaggcatgc aaactggagg acatagccag tctccctttc    7680
tttccaagac atccactgtt aactctaggt tactacctca aggtagtggt ggtattataa    7740
gtgggagaag cagtgccctg gtgcatgagc tggtgctcc ttctgctgct cggccaccaa    7800
accttggttt tagtgctgaa cccacacctc aaatcccttc acctgttaaa gctgtttctg    7860
ccatacccgc tgagaagcca caacctccag ctgcaaaatt gaattttgat gaacttcagc    7920
gtaaaactgt ttctcttctg gaagaatatt tcaatgtccg gcttttggac gaggcattac    7980
agtgtgtgga ggaactaaaa gctccagctt attaccctga gtttgtcaag gaagctattt    8040
cccttgctct agataaaagt ccgccatgcg ctgaacctgt tgccaatctt tttgaatatc    8100
tgttcattaa gaagattctt tcagccagag acatagggac tgggtgcatg ttatttgctt    8160
ctctgctgga tgatatcggc atagatttac ctaaagcacc aaataatttt ggtgagataa    8220
tagggaaact agttttggct gggggtttgg attttaaggt ggtgacagaa atccttaaga    8280
aggtggagga tgaccggttc cagaaagcaa tatttttcttc tgcgttgcag gtaattacct    8340
ctgcatctgg gcaagctgtg ctggatgcac aagcatctga tattgaggcc tgccagagtc    8400
tgttcaactg aatcagatga gagtttgcat gagaataccg atctctgtaa ctgaaagaac    8460
atctctgcct tgtttcacaa ctttcaaatt ccctatcctt tacgctcgca ctttttagag    8520 catttttgtat tacagtatgt tataaaagtg ggagcttcca gtatcaggta ttttctcgag    8580
ttgtataatt ttcttttgtc ttgttttgat gtcgtagagg ttgttgattg agggaaaatt    8640
caaaccataa agctaaggat tttgttttttc agttggctaa tcatgtgcca agagaatggc    8700
ctatccaccc gggggtccaa atgctttttgt acttcattag tttcattttt ttccctttat    8760
tttctcgaca gagtaattgt taacctggtc agttcataaa tatcatcgtc gttacttta    8820 catgtgtttt ttttaaaggt ttaaatttct gctttgtgtg ggtgcatgtc atcaattatt    8880
tcattcctct ggataggagg aacgtctcaa gtcccaacaa tatcagaggg gattattaaa    8940
tttaattttg aagtgtcaaa tcccatttta tcatagatat tatttggtcg tgtttgtaaa    9000
```

<210> SEQ ID NO 11
<211> LENGTH: 6670
<212> TYPE: DNA
<213> ORGANISM: Glycine max

<400> SEQUENCE: 11

```
ttgactttac ctacatgaac cagaaccttc aatggtccac aaaacgtgtc gaatattggt      60
taagatattg ctggaaagaa gacaaggaaa ttaagaagaa aaaaattatt taaaaaaaaa     120
tgaagaaaca aaattataat tttcttaaag acaataaaat gagtacttaa atttcttgcc     180
attaattagt tccattttac tgacttaaaa atgtagaatt ttgggtgtaa gattattttt     240
ggagcacgtc aaatattatt aagaagaaga acatactaa agaacacggg ggactaggcc     300 ataaccctg aggaaattaa aagaacctac acgaaggaat ggtactccta ttctaaacaa     360
agtctgccct gataaatcca ggattgttgc taggtgcacc tagcattatt actggtgtac     420
tcaacatttt ttgaaaatga taaaattatc cctgtcaatt taggtgtgtt tgattataaa     480
aggaaaggaa agaaaaaag aaagagagaa aggaaagaa gtgaattaat gaggtgatta     540 tttttttagtg tttgcgttca aattttagtg ttttgttcat gtgtttgtgt tttaatttc     600
```

```
tttttttgaa atatttattt tttgtgatta aatgtttgat ataatgtctc aatcaagaag      660
tacatcttct tcaagtgttt gtaacaatga ataattgtc  aaatattaaa ggaaaaatta     720
ttattgtctt aagaaagaat caattattaa tttgttattg agtatttaat aaagatgtta      780
aggtaatttt atctgttcac atatatttaa ttgatgttag ttaatgacgt taatagaaga      840
aggataaaag taatataaaa aatgaaagaa tatcaagtac aatttaaaaa aacacacagg      900
atatgagtat aataaaaata ttagaacaat tcatatatt  tcaattaaca agagtaaaaa     960
taatataaaa aagaagtatc aaatacaata tgagaaaaac ataagaatgt gagtgtaatt     1020
tactctaaaa aagatatata attatatgag aaaagagtaa gtatacaaat ggttttattt     1080
taagaaatga aaaataatat agaaatgaaa aataatattt cgtataaata ttttatttag     1140
taattgatat atatatatat atatatatat atataaaagc agaataatat ttttaaaaag     1200
taactgtatt tttaatataa tagtacaatt tagtataagt aatatgaaat tgagtgttga     1260
taataactaa gatatattta tatttatatt tattacataa tatctcaaat tcaaaattta     1320
tttttgtga  aaacttacta ataattagga ttttcccatc tagcccacta attatacagg     1380
ctaaattatc catgcatgga gtccattttt taatgataaa agcttacgga cgctaccacg     1440
tggtgatctt gcctacgttg gggagtcata cccattagta ctattatttc gatgggtgtc     1500
ttttttgtgg caaataaagt agccactaat tactgtaatg ctgggctttt ggagttgttc     1560
tcataaagaa aagaagagaa atggagtttg gtacgaaaat gattttcgtc actctcatac     1620
gagcgatatg ttttcagtta aactgcattt gatattattc taagttttta aatcaatatt     1680
tgtcttcaaa aaagttagc  gctccacgtg cttactcgtg tgcttcgcgc aaaataacac     1740
tgctcagata cgaagaaca  ttattgtttg tttcgttaag aaacaaaaca gcacgagctg     1800
taaacgtggg tgagtatttt tttataaata attaagccca tgcatatttg tctgtagtga     1860
aaactgaaaa ctaaagtctg tcgtcaggtt tgaacaatat gaactgaaaa gaaataacgg     1920
aaagtggaaa ccacacataa caaaaagact ctcacacttg agaagaaaaa gagtggaata     1980
atatctatca attaaggttc tccctatttt gcccctcaaa caataaaaaa taataattat     2040
caaccacttt ttcacgttat aaatagcata gaactcggga gatcttgcca cagcagtaac     2100
caccaacaag gcatcaataa tccttttcctt tcccttccaa accttcgaga atgagcatta    2160
tcatgtccac caagtcatcg ctgaagtctc tcctccaaaa gggtgagaat gagcataatc     2220
cattaaccat gtctgatgaa cagattttgg aacaaattta ctcaacccac gtccacagtg     2280
acaccaagtt tgatgtggat tctcttttca cccttgttga gaacactctt agacgttcaa     2340
cccacattgt tgacaatctt gtgcaggtag cctttttcac tttcttctta atttccctcc     2400
acgttttgc  ttcctatata tttacgcacc cttcaaaaat attcatgcac ttattaattt     2460
ttacagggat cccatgcaag cttggagcac attgatgaca agatccccca attcaattca     2520
ccactttgta ccttgaagca aatttctttt gaggtcattc acagatctaa ttcaaagaga     2580
ttttttttt  ttaaaaaaaa gagatataca cttacattgt atatataaaa caaaaactgc     2640
atgtgatagt gaataaaatt cataataaca tgataactaa tagctcgtgc acgtaacata     2700
gtgagttgtt gtggtgacag atgtcatgca agcctccaag tgaggaaatt ggtcaccgaa     2760
ctacactggc catacttaac aagctctcaa actatgagtg ggatgctaag gctgtgctga     2820
cactagcagc ttttgcactc gaatatacg  agttctggct gctagcacag taccaaccaa     2880
cagatcctct tgcaaaatct gtggctattt tgaagcgagt gccagtgctc gcaaagcccg     2940
```

```
cagcacttca aaagcatcga caagccatcc ttgaggttaa caatttggtg aaagcaacgt    3000
tgcaagttat tgaggttatc tttgagctgg agaagcttac cacttatgac accaaagatg    3060
tacctgcttt ggggcttgca attgaacaaa tccctgttga tgtttactgg gccatcatca    3120
ctatcgtcgc tgtggttact cagattgatt gtctcaccac tgattcgtac gttgcaaact    3180
attaagactt gttttatttt tatacatgaa acaatgtcct tattatttta ttaattaatt    3240
gtaattttta aaatgtatga tttgtggatt atatatttaa gagagcacaa gcaagaactg    3300
tctcactatg gtcaaaagat caacatcata ctcagcaaac tcaggaagca gataactctc    3360
tgcagacaac agataggtta gcaattaaaa ttattgcctt tgcctttagt tattctctca    3420
tcgtgttttt ccttaaagga aatgtgcctt tgattcaaag ctatgattga tggaataaaa    3480
ggcacggagc agtaaatgag atgctaataa gaaaatttat ctatattctt tcagatgagg    3540
cacaatatta tcgcaagctg aggaaatttt tccaaacccc cactgaaata atggaggtgt    3600
ttaaggttct gattttcaat aaggatgctc ctcagccact gttcgatggt gctactaaga    3660
ctaaggtttg tgatttcttg ttaggttata tttggataaa aattaagaac atgttttga    3720 gcattttaat gcatattttt aaagtttagg aaataaaata aacaaaaatt attattttga    3780
aaaataaaat tactttgaa ctcctcagtc taaacattca cttgaaatca ttgaaaatca    3840
atttctcctc atccaaaagt caaaagaaaa tgattgttaa agctaacttt atatatatat    3900
atatataaaa tacgacgcta aaaaggggga ggggtggtgt tgaaactcca agacctcgaa    3960
ctaaaatgca taaatcgga caaaatgaat ataatttatg tcaagaacct gggtttcatc    4020
tctataatac atttttaaga aaggtaaata actttaaata tgaataattc ataagtctag    4080
agttaaaagt cataattaat gattaaaaaa tgcataaaat gggacaaaat aaagataatt    4140
tatgccacac cttcggatag gttaaaataa agtgtggaac aaagagttaa cgatcctagt    4200
cttgtagaaa acgatgcgtg gttttttgtc aaaagggaaa ttaattttgg tactgtgtca    4260
aacaaaaggc aacaaaactt taggtgcttt tgattataaa aggaaaggaa aaaagaaag    4320 agaaaaaaag gaaggaaaa aaaaagaaag agagaaaagg aagaaaaaa gaaaaagaa    4380 aattaagtgt gtatataaaa taatataaat atatttaatt aaaaaaatac acaaaataaa    4440
tatattttag tcaggcttaa aatcactttt ctctttcctt cttccctccc gtttcatact    4500
cacttttttt taatggaaga aaggttaatt aattgacaaa tatttcccta tttttatgaa    4560
aactattttt ccttcttctt attatccgtc ctactgatta aaatatgtgt ttaaattatt    4620
aaattcatat tgcagtacat acataacata catttttaat taaaaaaaaa tatgaaaatt    4680
aatattttta atgccaaaat aagagtccat ttatttaaac ttaaaaaagg caattaaaaa    4740
aagtgtaaca cttttttaac aaacaaatat gatttgcttc ttaaaaaaac tgcttattaa    4800 atatttttt tagagaaaca catcagaaaa accaaaaact atttatttca ttaatttttt    4860
ttaaaaaaaa agcttaatca gacaagtttg gctaaagtta tttgtttgat attcgcctcg    4920
cgctaaaatc aacccaaaac gtcaatgtta aagcgtagtt attggatgtc gacgagcatt    4980
tgataaagaa taattcattt gaattaatga atattctaga attatatata attaagataa    5040
tgatcttaaa gaatccaggt aagattgaag gaagattaat attattctca atacacattt    5100
tcacaataat ttctacaatt gcgaaagaca agagaagagt gagataaaaa caagtattgt    5160
aatggaaaaa acagaagaaa aaaagtgtt gtgatgagaa tttgaaataa attatcctaa    5220
tcctatatat gtctgtgaaa tgatatgctt tcaagtacca atcatttcac gcatctgaaa    5280
ttttttaatc ttgattgatt tgttgtctgg taggtcgata tcacggtgct aaaaaagaag    5340
```

```
aacgtgtact tgtttatttc ttccctggac atcacggagg aagagatttc agtactccga    5400
ccagtttatg attctattaa aactaacgat cagtataaga ttgtgtggat tcccattgta    5460
gaagaatgga ccgagcaatt gcacaagaaa tttgaggttt tgaaaagcaa gatgccttgg    5520
tatgtggtgc agcattctgg aaccatagca gggtacaagt acattaagga ggaatggcac    5580
ttcaaaaaga agcctatggt tgtggtgttg agccctcaag ggaaggtgca acactcaaac    5640
gcattccatt tgatccaggc tcatggaacc agggcttttc cctttacaac tttgaatgaa    5700
gaaaaaataa acagtgagaa cgattgggtt ggctccgtat taggcagcat tcaccccagc    5760
ataagcacct cggtaagtat atatatttca cacaaaaatt aattaagttt ttagcgcaca    5820
ttacatagaa tttaatggtc atgcacatta taatcataat attttaaata attattataa    5880
caggcagcaa acttaaccta tgtagtagat tatggtaaaa taatggtgca aaactttta    5940 tactatataa ttttttctct ctattatatg tgtactattt caaccataat ggtgtaaaac    6000
tttgtctgta aggttctcca ttgaattaga aaactacata ggattggata acatatata    6060 ataataaggt gttgtgatac tttgtatgaa gcagatcaaa gagcaaaagt acatttctt    6120 ttatgggggc aacgacaaag actggatcca acagttcacc aagtacgtta ctgcccttgc    6180
aaatgatgct gctataaagg aggcaaagat ttccatagag ttgttttgtg tggataagga    6240
agacaaaagc cttgtgaggc gcttttggag tggcattgag agtttatttg tgactaaggt    6300
tcacaaacaa gctgatgcag tgactcaaga agtgcaaaag atgctttctt acaagaatga    6360
aactggatgg tctctcctca gtaaagggcc atcagtggtg gtgagtggtc atggaacaac    6420
aatcttgaag acagtggcag agtttgagaa atggaaagag gttgtgatca aaagggctt    6480 tgcggtaacc ttcaaagaat accatcagaa gattgtgggg accactcacc gttgctcaca    6540
ccttgagatt cctaacgttg cagggaagtt acctgagacc atcaaatgct cagattgtcc    6600
tagggtaatg gagattttca tcagctataa atgctgccac aatgagaata ctgccaatgc    6660
cattcactag                                                           6670

<210> SEQ ID NO 12
<211> LENGTH: 6666
<212> TYPE: DNA
<213> ORGANISM: Glycine max

<400> SEQUENCE: 12
tgactttacc tacatgaacc agaaccttca atggtccaca aaacgtgtcg aatattggtt      60
aagatattgc tggaaagaag acaaggaaat taaagaagaa aaaattattt aaaaaaaaat     120
gaagaaacaa aattataatt ttcttaaaga caataaaatg agtacttaaa tttcttgcca     180
ttaattagtt ccattttact gacttaaaaa tgtagaattt tgggtgtaag attattttg     240 gagcacgtca atattatta agaagaagaa acatactaaa gaacacgggg gactaggcca     300 taaccccctga ggaaattaaa agaacctaca cgaaggaatg gtactcctat tctaaacaaa     360
gtctgccctg ataaatccag gattgttgct aggtgcacct agcattatta ctggtgtact     420 caacatttt tgaaaatgat aaaattatcc ctgtcaattt aggtgtgttt gattataaaa     480
ggaaaggaaa agaaaaaaga aagagagaaa aggaagagaa tgaattaatg aggtgattat     540 ttttagtgt ttgcgttcaa attttagtgt tttgttcatg tgtttgtgtt ttaatttctt     600
tttttgaaat atttattttt tgtgattaaa tgtttgatat aatgtctcaa tcaagaagta     660
catcttcttc aagtgtttgt aacaatgaaa taatggtcaa atattaaagg aaaaattatt     720
```

```
attgtctttta gaaagaatca attattaatt tgttattgag tatttaataa agatgttaag    780
gtaattttat ctgttcacat atatttaatt gatgttagtt aatgacgtta atagaagaag    840
gataaaagta atataaaaaa tgaaagaata tcaagtacaa tttaaaaaaa cacacaggat    900
atgagtataa taaaaatatt agaacaattt catatatttc aattaacaag agtaaaaata    960
atataaaaaa gaagtatcaa atacaatatg agaaaaacat aagaatgtga gtgtaattta   1020
ctctaaaaaa gatatataat tatatgagaa aagagtaagt atacaaatgg ttttatttta   1080
agaaatgaaa aataatatag aaatgaaaaa taatatttcg tataaatatt ttatttagta   1140
attgatatat atatatatat atatatatat aaaagcagaa taatatttt aaaaagtaac    1200 tgtattttta atataatagt acaatttagt ataagtaata tgaaattgag tgttgataat   1260
aactaagata tatttatatt tatatttatt acataatatc tcaaattcaa aatttatttt   1320
ttgtgaaaac ttactaataa ttaggatttt cccatctagc ccactaatta tacaggctaa   1380
attatccatg catggagtcc atttttaat gataaaagct tacggacgct accacgtggt    1440
gatcttgcct acgttgggga gtcatacca ttagtactat tatttcgatg ggtgtctttt    1500
ttgtggcaaa taaagtagcc actaattact gtaatgctgg gcttttggag ttgttctcat   1560
aaagaaaaga agagaaatgg agtttggtac gaaaatgatt ttcgtcactc tcatacgagc   1620
gatatgtttt cagttaaact gcatttgata ttattctaag tttttaaatc aatatttgtc   1680
ttcaaaaaaa gttagcgctc cacgtgctta ctcgtgtgct tcgcgcaaaa taacactgct   1740
cagatacgaa agaacattat tgtttgtttc gttaagaaac aaaacagcac gagctgtaaa   1800
cgtgggtgag tatttttta taataatta agcccatgca tatttgtctg tagtgaaaac    1860
tgaaaactaa agtctgtcgt caggtttgaa caatatgaac tgaaagaaa taacggaaag    1920 tggaaaccac acataacaaa aagactctca cacttgagaa gaaaaagagt ggaataatat   1980
ctatcaatta aggttctccc tattttgccc ctcaaacaat aaaaaataat aattatcaac   2040
cactttttca cgttataaat agcatagaac tcgggagatc ttgccacagc agtaaccacc   2100
aacaaggcat caataatcct ttcctttccc ttccaaacct tcgagaatga gcattatcat   2160
gtccaccaag tcatcgctga agtctctcct ccaaaagggt gagaatgagc ataatccatt   2220
aaccatgtct gatgaacaga ttttggaaca aatttactca acccacgtcc acagtgacac   2280
caagtttgat gtggattctc ttttcaccct tgttgagaac actcttagac gttcaaccca   2340
cattgttgac aatcttgtgc aggtagcctt tttcactttc ttcttaattt ccctccacgt   2400
ttttgcttcc tatatattta cgcacccttc aaaaatattc atgcacttat taattttac    2460 agggatccca tgcaagcttg gagcacattg atgacaagat cccccaattc aattcaccac   2520
tttgtacctt gaagcaaatt tcttttgagg tcattcacag atctaattca aagagatttt   2580 tttttttaa aaaaagaga tatacactta cattgtatat ataaaacaaa aactgcatgt     2640
gatagtgaat aaaattcata ataacatgat aactaatagc tcgtgcacgt aacatagtga   2700
gttgttgtgg tgacagatgt catgcaagcc tccaagtgag gaaattggtc accgaactac   2760
actggccata cttaacaagc tctcaaacta tgagtgggat gctaaggctg tgctgacact   2820
agcagctttt gcactcgaat atagcgagtt ctggctgcta gcacagtacc aaccaacaga   2880
tcctcttgca aaatctgtgg ctattttgaa gcgagtgcca gtgctcgcaa agcccgcagc   2940
acttcaaaag catcgacaag ccatccttga ggttaacaat ttggtgaaag caacgttgca   3000
agttattgag gttatctttg agctggagaa gcttaccact tatgacacca agatgtacc    3060 tgctttgggg cttgcaattg aacaaatccc tgttgatgtt tactgggcca tcatcactat   3120
```

```
cgtcgctgtg gttactcaga ttgattgtct caccactgat tcgtacgttg caaactatta    3180
agacttgttt tattttttata catgaaacaa tgtccttatt attttattaa ttaattgtaa   3240
tttttaaaat gtatgatttg tggattatat atttaagaga gcacaagcaa gaactgtctc    3300
actatggtca aaagatcaac atcatactca gcaaactcag gaagcagata actctctgca    3360
gacaacagat aggttagcaa ttaaaattat tgcctttgcc tttagttatt ctctcatcgt    3420 gttttttcctt aaaggaaatg tgcctttgat tcaaagctat gattgatgga ataaaaggca   3480
cggagcagta aatgagatgc taataagaaa atttatctat attctttcag atgaggcaca    3540
atattatcgc aagctgagga aattttttcca accccccact gaaataatgg aggtgtttaa   3600
ggttctgatt ttcaataagg atgctcctca gccactgttc gatggtgcta ctaagactaa   3660
ggtttgtgat ttcttgttag gttatatttg gataaaaatt aagaacatgt ttttgagcat    3720
tttaatgcat attttttaaag tttaggaaat aaaataaaca aaaattatta ttttgaaaaa   3780
taaaattact tttgaactcc tcagtctaaa cattcacttg aaatcattga aaatcaattt    3840
ctcctcatcc aaaagtcaaa agaaaatgat tgttaaagct aactttatat atatatatat    3900
ataaaatacg acgctaaaaa aggggagggg tggtgttgaa actccaagac ctcgaactaa    3960
aatgcataaa atcggacaaa atgaatataa tttatgtcaa gaacctgggt ttcatctcta    4020
taatacattt ttaagaaagg taaataactt taaatatgaa taattcataa gtctagagtt    4080
aaaagtcata attaatgatt aaaaaatgca taaaatggga caaaataaag ataatttatg    4140
ccacaccttc ggataggtta aaataaagtg tggaacaaag agttaacgat cctagtcttg    4200
tagaaaacga tgcgtggttt tttgtcaaaa gggaaattaa ttttggtact gtgtcaaaca    4260
aaaggcaaca aaactttagg tgcttttgat tataaaagga aaggaaaaaa agaaagagaa    4320
aaaaaggaaa ggaaaaaaaa agaaagagag aaaaggaaag aaaaagaaa aagaaaatt     4380 aagtgtgtat ataaaataat ataaatatat ttaattaaaa aaatacacaa aataaatata   4440
ttttagtcag gcttaaaatc acttttctct ttccttcttc cctcccgttt catactcact    4500 ttttttttaat ggaagaaagg ttaattaatt gacaaatatt tccctatttt tatgaaaact   4560 attttttcctt cttcttatta tccgtcctac tgattaaaat atgtgtttaa attattaaat   4620
tcatattgca gtacatacat aacatacatt tttaattaaa aaaaaatatg aaaattaata   4680
tttttaatgc caaaataaga gtccatttat ttaaacttaa aaaaggcaat taaaaaaagt    4740
gtaacacttt tttaacaaac aaatatgatt tgcttcttaa aaaactgct tattaaatat    4800 tttttttaga gaaacacatc agaaaaacca aaactatttt atttcattaa tttttttttaa   4860 aaaaaaagct taatcagaca agtttggcta agttatttg tttgatattc gcctcgcgct    4920
aaaatcaacc caaacgtca atgttaaagc gtagttattg gatgtcgacg agcatttgat    4980
aaagaataat tcatttgaat taatgaatat tctagaatta tatataatta agataatgat    5040
cttaaagaat ccaggtaaga ttgaaggaag attaatatta ttctcaatac acattttcac    5100
aataatttct acaattgcga aagacaagag aagagtgaga taaaaacaag tattgtaatg    5160
gaaaaaacag aagaaaaaaa agtgttgtga tgagaatttg aaataaatta tcctaatcct    5220
atatatgtct gtgaaatgat atgctttcaa gtaccaatca tttcacgcat ctgaaatttt    5280
ttaatcttga ttgatttgtt gtctggtagg tcgatatcac ggtgctaaaa aagaagaacg    5340
tgtacttgtt tatttcttcc ctggacatca cggaggaaga gatttcagta ctccgaccag    5400
tttatgattc tattaaaact aacgatcagt ataagattgt gtggattccc attgtagaag    5460
```

-continued

| | |
|---|---|
| aatggaccga gcaattgcac aagaaatttg aggttttgaa aagcaagatg ccttggtatg | 5520 |
| tggtgcagca ttctggaacc atagcagggt acaagtacat taaggaggaa tggcacttca | 5580 |
| aaaagaagcc tatggttgtg gtgttgagcc ctcaagggaa ggtgcaacac tcaaacgcat | 5640 |
| tccatttgat ccaggctcat ggaaccaggg cttttcccct tacaactttg aatgaagaaa | 5700 |
| aaataaacag tgagaacgat tgggttggct ccgtattagg cagcattcac cccagcataa | 5760 |
| gcacctcggt aagtatatat atttcacaca aaaattaatt aagttttag cgcacattac | 5820 |
| atagaattta atggtcatgc acattataat cataatattt taaataatta ttataacagg | 5880 |
| cagcaaactt aacctatgta gtagattatg gtaaaataat ggtgcaaaac tttttatact | 5940 |
| atataatttt ttctctctat tatatgtgta ctatttcaac cataatggtg taaaactttg | 6000 |
| tctgtaaggt tctccattga attagaaaac tacataggat tggataaaca tatataataa | 6060 |
| taaggtgttg tgatactttg tatgaagcag atcaaagagc aaaagtacat tttcttttat | 6120 |
| gggggcaacg acaaagactg gatccaacag ttcaccaagt acgttactgc ccttgcaaat | 6180 |
| gatgctgcta taaggaggc aaagatttcc atagagttgt tttgtgtgga taaggaagac | 6240 |
| aaaagccttg tgaggcgctt ttggagtggc attgagagtt tatttgtgac taaggttcac | 6300 |
| aaacaagctg atgcagtgac tcaagaagtg caaaagatgc tttcttacaa gaatgaaact | 6360 |
| ggatggtctc tcctcagtaa agggccatca gtggtggtga gtggtcatgg aacaacaatc | 6420 |
| ttgaagacag tggcagagtt tgagaaatgg aaagaggttg tgatcaaaaa gggctttgcg | 6480 |
| gtaaccttca agaatacca tcagaagatt gtggggacca ctcaccgttg ctcacacctt | 6540 |
| gagattccta acgttgcagg gaagttacct gagaccatca aatgctcaga ttgtcctagg | 6600 |
| gtaatggaga ttttcatcag ctataaatgc tgccacaatg agaatactgc caatgccatt | 6660 |
| cactag | 6666 |

<210> SEQ ID NO 13
<211> LENGTH: 6987
<212> TYPE: DNA
<213> ORGANISM: Glycine max

<400> SEQUENCE: 13

| | |
|---|---|
| ttgactttac ctacatgaac cagaaccttc aatggtccac aaaacgtgtc gaatattggt | 60 |
| taagatattg ctggaaagaa gacaaggaaa ttaaagaaga aaaattatt taaaaaaaaa | 120 |
| tgaagaaaca aaattataat tttcttaaag acaataaaat gagtacttaa atttcttgcc | 180 |
| attaattagt tccatttac tgacttaaaa atgtagaatt ttgggtgtaa gattattttt | 240 |
| ggagcacgtc aaatattatt aagaagaaga aacatactaa agaacacggg ggactaggcc | 300 |
| ataaccccctg aggaaattaa aagaacctac acgaaggaat ggtactccta ttctaaacaa | 360 |
| agtctgccct gataaatcca ggattgttgc taggtgcacc tagcattatt actggtgtac | 420 |
| tcaacatttt ttgaaaatga taaaattatc cctgtcaatt taggtgtgtt tgattataaa | 480 |
| aggaaaggaa aagaaaaaag aaagagagaa aggaaagaa gtgaattaat gaggtgatta | 540 |
| tttttagtg tttgcgttca aattttagtg tttgttcatg tgtttgtgtt ttaatttctt | 600 |
| tttttgaaat attttatttt tttgtgataa atgtttgata ataatgtctc aatcaagaag | 660 |
| tacatcttct tcaagtgttt gtaacaatga ataatggtc aaatattaaa ggaaaaatta | 720 |
| ttattgtctt tagaaagaat caattattaa tttgttattg agtatttaat aaagatgtta | 780 |
| aggtaatttt atctgttcac atatatttaa ttgatgttag ttaatgacgt taatagaaga | 840 |
| aggataaaag taatataaaa aatgaaagaa tatcaagtac aatttaaaaa aacacacagg | 900 |

```
atatgagtat aataaaaata ttagaacaat ttcatatatt tcaattaaca agagtaaaaa      960
taatataaaa aagaagtatc aaatacaata tgagaaaaac ataagaatgt gagtgtaatt     1020
tactctaaaa aagatatata attatatgag aaaagagtaa gtatacaaat ggttttattt     1080
taagaaatga aaataatat agaaatgaaa aataatattt cgtataaata ttttatttag      1140
taattgatat atatatatat atatatatat ataaaagcag aataatattt ttaaaaagta     1200
actgtatttt taatataata gtacaattta gtataagtaa tatgaaattg agtgttgata     1260
ataactaaga tatatttata tttatattta ttacataata tctcaaattc aaaatttatt    1320
ttttgtgaaa acttactaat aattaggatt ttcccatcta gcccactaat tatacaggct    1380
aaattatcca tgcatggagt ccattttta atgataaaag cttacggacg ctaccacgtg     1440
gtgatcttgc ctacgttggg gagtcatacc cattagtact attatttcga tgggtgtctt   1500
ttttgtggca aataaagtag ccactaatta ctgtaatgct gggcttttgg agttgttctc   1560
ataaagaaaa gaagagaaat ggagtttggt acgaaaatga ttttcgtcac tctcatacga   1620
gcgatatgtt ttcagttaaa ctgcatttga tattattcta gttttttaaa tcaatatttg   1680
tcttcaaaaa aagttagcgc tccacgtgct tactcgtgtg cttcgcgcaa aataacactg   1740
ctcagatacg aaagaacatt attgtttgtt tcgttaagaa acaaaacagc acgagctgta   1800
aacgtgggtg agtatttttt tataaataat taagcccatg catatttgtc tgtagtgaaa   1860
actgaaaact aaagtctgtc gtcaggtttg aacaatatga actgaaaaga aataacggaa   1920
agtggaaacc acacataaca aaaagactct cacacttgag aagaaaaaga gtggaataat  1980
atctatcaat taaggttctc cctatttgc ccctcaaaca ataaaaaata ataattatca    2040 accactttt cacgttataa atagcataga actcgggaga tcttgccaca gcagtaacca   2100
ccaacaaggc atcaataatc cttttccttc ccttccaaac cttcgagaat gagcattatc   2160
atgtccacca agtcatcgct gaagtctctc ctccaaaagg gtgagaatga gcataatcca   2220
ttaaccatgt ctgatgaaca gattttggaa caaatttact caacccacgt ccacagtgac  2280
accaagtttg atgtggattc tcttttcacc cttgttgaga acactcttag acgttcaacc   2340
cacattgttg acaatcttgt gcaggtagcc ttttcactt tcttcttaat ttccctccac   2400 gttttttgctt cctatatatt tacgcaccct tcaaaaatat tcatgcactt attaattttt    2460
acagggatcc catgcaagct tggagcacat tgatgacaag atcccccaat tcaattcacc   2520
actttgtacc ttgaagcaaa tttcttttga ggtcattcac agatctaatt caaagagatt    2580 ttttttttt aaaaaaaga gatatacact tacattgtat atataagaca aaaactgcat     2640
gtgatagtga ataaaattca taataacatg ataactaata gctcgtgcac gtaacatagt    2700
gagttgttgt ggtgacagat gtcatgcaag cctccaagtg aggaaattgg tcaccgaact    2760
acactggcca tacttaacaa gctctcaaac tatgagtggg atgctaaggc tgtgctgaca    2820
ctagcagctt ttgcactcga atatagcgag ttctggctgc tagcacagta ccaaccaaca    2880
gatcctcttg caaaatctgt ggctattttg aagcgagtgc cagtgctcgc aaagcccgca    2940
gcacttcaaa agcatcgaca agccatcctt gaggttaaca atttggtgaa agcaacgttg    3000
caagttattg aggttatctt tgagctggag aagcttacca cttatgacac caaagatgta   3060
cctgctttgg ggcttgcaat tgaacaaatc cctgttgatg tttactgggc catcatcact  3120
atcgtcgctg tggttactca gattgattgt ctcaccactg attcgtacgt tgcaaactat   3180
taagacttgt tttatttta tacatgaaac aatgtcctta ttatttatt aattaattgt     3240
```

```
aatttttaaa atgtatgatt tgtggattat atatttaaga gagcacaagc aagaactgtc    3300
tcactatggt caaaagatca acatcatact cagcaaactc aggaagcaga taactctctg    3360
cagacaacag ataggttagc aattaaaatt attgcctttg cctttagtta ttctctcatc    3420 gtgttttttcc ttaaaggaaa tgtgcctttg attcaaagct atgattgatg gaataaaagg   3480
cacggagcag taaatgagat gctaataaga aaatttatct atattctttc agatgaggca    3540
caatattatc gcaagctgag gaaattttttc caaaccccca ctgaaataat ggaggtgttt   3600
aaggttctga ttttcaataa ggatgctcct cagccactgt tcgatggtgc tactaagact    3660
aaggtttgtg atttcttgtt aggttatatt tggataaaaa ttaagaacat gttttttgagc   3720 attttaatgc atatttttaa agtttaggaa ataaaataaa caaaaattat tattttgaaa    3780
aataaaatta cttttgaact cctcagtcta acattcact tgaaatcatt gaaaatcaat     3840
ttctcctcat ccaaaagtca aagaaaatg attgttaaag ctaactttat atatatatat     3900
atataaaata cgacgctaaa aaggggagg ggtggtgttg aaactccaag acctcgaact     3960
aaaatgcata aaatcggaca aatgaatat aatttatgtc aagaacctgg gtttcatctc     4020
tataatacat ttttaagaaa ggtaaataac tttaaatatg aataattcat aagtctagag    4080
ttaaaagtca taattaatga ttaaaaaatg cataaaatgg gacaaaataa agataattta    4140
tgccacacct tcggataggt taaaataaag tgtggaacaa agagttaacg atcctagtct    4200
tgtagaaaac gatgcgtggt tttttgtcaa aagggaaatt aattttggta ctgtgtcaaa    4260
caaaaggcaa caaaacttta ggtgcttttg attataaaag gaaggaaaa aaagaaagag    4320 aaaaaaagga aaggaaaaaa aaagaaagag agaaaaggaa agaaaaaaga aaaaagaaaa    4380
ttaagtgtgt atataaaata atataaatat atttaattaa aaaaatacac aaaataaata    4440
tattttagtc aggcttaaaa tcacttttct ctttccttct tccctcccgt ttcatactca    4500
ctttttttta atggaagaaa ggttaattaa ttgacaaata tttccctatt tttatgaaaa    4560 ctattttttcc ttcttcttat tatccgtcct actgattaaa atatgtgttt aaattattaa    4620
attcatattg cagtacatac ataacataca ttttttaatta aaaaaaaata tgaaaattaa    4680 tattttttaat gccaaaataa gagtccattt atttaaactt aaaaaaggca attaaaaaaa    4740
gtgtaacact ttttttaacaa acaaatatga tttgcttctt aaaaaaactg cttattaaat    4800
atttttttta gagaaacaca tcagaaaaac caaaaactat ttatttcatt aattttttttt    4860 aaaaaaaaag cttaatcaga caagtttggc taaagttatt tgtttgatat tcgcctcgcg    4920
ctaaaatcaa cccaaaacgt caatgttaaa gcgtagttat tggatgtcga cgagcatttg    4980
ataaagaata attcatttga attaatgaat attctagaat tatatataat taagataatg    5040
atcttaaaga atccaggtaa gattgaagga agattaatat tattctcaat acacattttc    5100
acaataattt ctacaattgc gaaagacaag agaagagtga gataaaaaca agtattgtaa    5160
tggaaaaaac agaagaaaaa aaagtgttgt gatgagaatt tgaaataaat tatcctaatc    5220
ctatatatgt ctgtgaaatg atatgctttc aagtaccaat catttcacgc atctgaaatt    5280
ttttaatctt gattgatttg ttgtctggta ggtcgatatc acggtgctaa aaagaagaa     5340 cgtgtacttg tttatttctt ccctggacat cacggaggaa gagatttcag tactccgacc    5400
agtttatgat tctattaaaa ctaacgatca gtataagatt gtgtggattc ccattgtaga    5460
agaatggacc gagcaattgc acaagaaatt tgaggtttg aaaagcaaga tgccttggta     5520
tgtggtgcag cattctggaa ccatagcagg gtacaagtac attaaggagg aatggcactt    5580
caaaaagaag cctatggttg tggtgttgag ccctcaaggg aaggtgcaac actcaaacgc    5640
```

-continued

```
attccatttg atccaggctc atggaaccag ggcttttccc tttacaactt tgaatgaaga      5700
aaaaataaac agtgagaacg attgggttgg ctccgtatta ggcagcattc accccagcat      5760
aagcacctcg gtaagtatat atatttcaca caaaaattaa ttaagttttt agcgcacatt      5820
acatagaatt taatggtcat gcacattata atcataatat tttaaataat tattataaca      5880
ggcagcaaac ttaacctatg tagtagatta tggtaaaata atggtgcaaa acttttata      5940 ctatataatt ttttctctct attatatgtg tactatttca accataatgg tgtaaaactt      6000
tgtctgtaag gttctccatt gaattagaaa actacatagg attggataaa catatataat      6060
aataaggtgt tgtgatactt tgtatgaagc agatcaaaga gcaaagtac attttctttt       6120 atgggggcaa cgacaaagac tggatccaac agttcaccaa gtacgttact gcccttgcaa      6180
atgatgctgc tataaaggag gcaaagattt ccatagagtt gttttgtgtg gataaggaag      6240
acaaaagcct tgtgaggcgc ttttggagtg gcattgagag tttatttgtg actaaggttc      6300
acaaacaagc tgatgcagtg actcaagaag tgcaaaagat gctttcttac aagaatgaaa      6360
ctggatggtc tctcctcagt aaagggccat cagtggtggt gagtggtcat ggaacaacaa      6420
tcttgaagac agtggcagag tttgagaaat ggaaagaggt tgtgatcaaa aagggctttg      6480
cggtaacctt caaagaatac catcagaaga ttgtggggac cactcaccgt tgctcacacc      6540
ttgagattcc taacgttgca gggaagttac ctgagaccat caaatgctca gattgtccta      6600
gggtaatgga gattttcatc agctataaat gctgccacaa tgagaatact gccaatgcca      6660
ttcactagaa tggaatgtgg gttctggttt gttatatatg ttatcgtgaa cgacagagag      6720
agtgtgagaa taagaggctt acctcagtta cctgctatgc gtgtctttca ggactacgta      6780
ctagcttcta tagtaaaata aagatcactc tctgtatcaa tgaaaaaaaa aaagttactt      6840
aattaaggtc tatatatgtt ctctatgtaa tatggagctg tattgaatct tagcattcaa      6900
ttaattaagc ttctttatat atagattgtg ttgcaatact tgagtagtac aacacaactt      6960
taatatgaaa attaaaagtt gcgctgc                                          6987
```

<210> SEQ ID NO 14
<211> LENGTH: 18
<212> TYPE: DNA
<213> ORGANISM: Glycine max

<400> SEQUENCE: 14

```
atatatatat atatatat                                                    18
```

<210> SEQ ID NO 15
<211> LENGTH: 26
<212> TYPE: DNA
<213> ORGANISM: Glycine max

<400> SEQUENCE: 15

```
atatatatat atatatatat atatat                                           26
```

<210> SEQ ID NO 16
<211> LENGTH: 2144
<212> TYPE: DNA
<213> ORGANISM: Artificial sequence
<220> FEATURE:
<223> OTHER INFORMATION: G10-90 promoter + XVE fusion protein + rat
glucocorticoid receptor + pea rbcS Terminator

<400> SEQUENCE: 16

```
atagtttaaa ctgaaggcgg gaaacgacaa tctgatccaa gctcaagcta agcttgcatg        60
cctgcaggat atcgtggatc caagcttgcc acgtgccgcc acgtgccgcc acgtgccgcc       120
acgtgcctct agaggatcca tctccactga cgtaagggat gacgcacaat cccactatcc       180
ttcgcaagac ccttcctcta tataaggaag ttcatttcat ttggagagga cacgctggga       240
tccccaattc cgggcggaat gaaagcgtta acggccaggc aacaagaggt gtttgatctc       300
atccgtgatc acatcagcca gacaggtatg ccgccgacgc gtgcggaaat cgcgcagcgt       360
ttggggttcc gttccccaaa cgcggctgaa gaacatctga aggcgctggc acgcaaaggc       420
gttattgaaa ttgtttccgg cgcatcacgc gggattcgtc tgttgcagga agaggaagaa       480
gggttgccgc tggtaggtcg tgtggctgcc ggtgaaccgt cgagcgcccc ccgaccgat       540
gtcagcctgg gggacgagct ccacttagac ggcgaggacg tggcgatggc gcatgccgac       600
gcgctagacg atttcgatct ggacatgttg ggggacgggg attccccggg tccgggattt       660
accccccacg actccgcccc ctacggcgct ctggatatgg ccgacttcga gtttgagcag       720
atgtttaccg atgcccttgg aattgacgag tacggtgggg atccgtctgc tggagacatg       780
agagctgcca acctttggcc aagcccgctc atgatcaaac gctctaagaa gaacagcctg       840
gccttgtccc tgacggccga ccagatggtc agtgccttgt tggatgctga gcccccata       900
ctctattccg agtatgatcc taccagaccc ttcagtgaag cttcgatgat gggcttactg       960
accaacctgg cagacaggga gctggttcac atgatcaact gggcgaagag ggtgccaggc      1020
tttgtggatt tgaccctcca tgatcaggtc caccttctag aatgtgcctg gctagagatc      1080
ctgatgattg gtctcgtctg gcgctccatg gagcacccag tgaagctact gtttgctcct      1140
aacttgctct tggacaggaa ccagggaaaa tgtgtagagg gcatggtgga gatcttcgac      1200
atgctgctgg gctacatcat ctcggttccgc atgatgaatc tgcagggaga ggagtttgtg      1260
tgcctcaaat ctattatttt gcttaattct ggagtgtaca catttctgtc cagcaccctg      1320
aagtctctgg aagagaagga ccatatccac cgagtcctgg acaagatcac agacactttg      1380
atccacctga tggccaaggc aggcctgacc ctgcagcagc agcaccagcg gctggcccag      1440
ctcctcctca tcctctccca catcaggcac atgagtaaca aaggcatgga gcatctgtac      1500
agcatgaagt gcaagaacgt ggtgcccctc tatgacctgc tgctggagat gctggacgcc      1560
caccgcctac atgcgcccac tagccgtgga ggggcatccg tggaggagac ggaccaaagc      1620
cacttggcca ctgcgggctc tacttcatcg cattccttgc aaaagtatta catcacgggg      1680
gaggcagagg gtttccctgc cacagtctga gagctccctg gcgaattccc agagatgtta      1740
gctgaaatca tcactaatca gataccaaaa tattcaaatg gaaatatcaa aaagcttctg      1800
tttcatcaaa aatgactcga cctaactgag taagctagct tgttcgagta ttatggcatt      1860
gggaaaactg ttttcttgt accatttgtt gtgcttgtaa tttactgtgt ttttattcg      1920
gttttcgcta tcgaactgtg aaatggaaat ggatggagaa gagttaatga atgatatggt      1980
ccttttgttc attctcaaat taatattatt tgttttttct cttatttgtt gtgtgttgaa      2040
tttgaaatta taagagatat gcaaacattt tgttttgagt aaaaatgtgt caaatcgtgg      2100
cctctaatga ccgaagttaa tatgaggagt aaaacatccc aaac                        2144
```

<210> SEQ ID NO 17
<211> LENGTH: 639
<212> TYPE: DNA

```
<213> ORGANISM: Arabidopsis thaliana

<400> SEQUENCE: 17
tacccgacga gtcagtaata aacggcgtca aagtggttgc agccggcaca cacgagtcgt      60
gtttatcaac tcaaagcaca aatactttc ctcaacctaa aaataaggca attagccaaa     120
aacaactttg cgtgtaaaca acgctcaata cacgtgtcat tttattatta gctattgctt     180
caccgcctta gctttctcgt gacctagtcg tcctcgtctt ttcttcttct tcttctataa     240 aacaatacc aaagagctct tcttcttcac aattcagatt tcaatttctc aaaatcttaa     300
aaactttctc tcaattctct ctaccgtgat caaggtaaat ttctgtgttc cttattctct     360
caaaatcttc gattttgttt tcgttcgatc ccaatttcgt atatgttctt tggtttagat     420
tctgttaatc ttagatcgaa gacgattttc tgggtttgat cgttagatat catcttaatt     480
ctcgattagg gtttcataga tatcatccga tttgttcaaa taatttgagt tttgtcgaat     540
aattactctt cgatttgtga tttctatcta gatctggtgt tagtttctag tttgtgcgat     600
cgaatttgta gattaatctg agttttctg attaacact                             639

<210> SEQ ID NO 18
<211> LENGTH: 301
<212> TYPE: DNA
<213> ORGANISM: Artificial sequence
<220> FEATURE:
<223> OTHER INFORMATION: LEX A OPERATOR + -46 TO +12 OF 35S PROMOTER

<400> SEQUENCE: 18
agcttgggct gcaggtcgag gctaaaaaac taatcgcatt atcatcccct cgacgtactg      60
tacatataac cactggtttt atatacagca gtactgtaca tataaccact ggttttatat     120
acagcagtcg acgtactgta catataacca ctggttttat atacagcagt actgtacata     180
taaccactgg ttttatatac agcagtcgag gtaagattag atatggatat gtatatggat     240
atgtatatgg tggtaatgcc atgtaatatg ctcgactcta ggatcttcgc aagacccttc     300
c                                                                     301
```

METHODS FOR IMPROVING PLANT ABIOTIC STRESS TOLERANCE AND YIELD

CROSS-REFERENCES TO RELATED APPLICATIONS

This application is a national phase entry under 35 U.S.C. § 371 of International Application No. PCT/EP2018/086228, filed on Dec. 20, 2018, which claims priority to U.S. Appl. No. 62/608,983, filed Dec. 21, 2017. The contents of each of these applications are incorporated herein by reference in the entirety, including the specification, drawings, and the claims.

TECHNICAL FIELD OF THE INVENTION

The present invention relates to a method for improving abiotic stress tolerance.

BACKGROUND OF THE INVENTION

Abiotic stress is currently one of the main constraints to crop yield worldwide. Abiotic stress comprises drought stress, waterlogging stress, osmotic stress, salt stress, heat stress and cold temperature stress. Plants are usually simultaneously exposed to different types of abiotic stress. For instance, drought stress is frequently associated with other abiotic stresses such as high temperature stress and salt stress. Climate models predict an increase in extreme temperatures and drought events in several world regions, thereby increasing the probability of crop exposure to abiotic stress. For sustainable agricultural development, irrigation practices must be established on the basis of efficient use of the available water resource. In addition, artificial irrigation increases energy use and production costs. Therefore, it is desirable to produce crop plants that have increased tolerance to abiotic stress.

Plants have evolved diverse adaptations to cope with drought stress. These involve the development of strategies that allow escape, avoidance, or tolerance to stress conditions. Drought escape refers to those strategies that allow completion of the plant's life cycle before the onset of drought, while drought avoidance strategies help the plant keeping high water status during stress. Drought tolerance mechanisms allow continued metabolism even at low water potentials (Nguyen, H. T., Babu, R. C. and Blum, A. (1997) *Breeding for drought resistance in rice: Physiology and molecular genetics considerations*. Crop Sci. 37:1426-1434). Among the physiological responses that have been shown to be associated with drought tolerance or resistance in soybean, many of them involve strategies for drought avoidance, such as traits related to root morphology and plasticity, stomatal and epidermal conductance and water use efficiency (WUE), or involve strategies for drought tolerance such as osmotic adjustment.

Legumes (Fabaceae) are a family of plants which include forage (alfalfa, clover, birdfoot trefoil) and grain legumes (beans, soybean, lentils and peanuts). Crops belonging to this family, because of their independence from inorganic sources of nitrogen, are fundamental for the sustainability of agro-ecosystems. Plant-bacteria symbiosis developed in this family is critical in the nitrogen natural cycle, furthermore these crops can minimize the detrimental environmental impact of agriculture and thus contribute to farming sustainability. Traditionally, soybean breeding has improved primarily for yield characteristics and not for crop performance under water limiting conditions. Then, improving drought resistance in soybean has been slow, and few reports exist on the identification of drought tolerant soybean germplasm and the genes associated to the trait (King, C. A., Purcell, L. C., Brye K. R. (2009). *Differential wilting among soybean genotypes in response to water deficit*. Crop Sci 49:290-298; Manavalan, L., Guttikonda, K., Tran, L., Nguyen, H. (2009). *Physiological and molecular approaches to improve drought resistance in soybean*. Plant and Cell Physiology 50, 1260-1276). Moreover, cultivated soybean is a plant species with narrow genetic diversity, which explains the little knowledge existing on soybean drought responses compared with the information available from other important crops cultivated in the same regions, such as wheat or corn. The first source of drought tolerance in soybean was identified in lines described as "slow wilting genotypes" (Hufstetler, E. V., Boerma, H. R., Carter, T. E., Earl, H. J. (2007). *Genotypic variation for three physiological traits affecting drought tolerance in soybean*. Crop Science, 47, 25-35). It has been proposed that genotypic differences for wilting may be associated with rooting traits (Pantalone, V., Burton, J., Carter, T. (1996). *Soybean Fibrous Root Heritability and Genotypic Correlations with Agronomic and Seed Quality Traits*. Crop Science, 36: 1120-1125; Hudak, C. M., Patterson, 1996. *Root distribution and soil moisture depletion pattern of a drought-resistant soybean plant introduction*. Agron. J. 88:478-485.), or conservation of soil water (Carter, T. E. and Rufty, T. W. (1993). *Soybean plant introduction exhibiting drought and aluminum tolerance*. In: Adaptation of food crops to temperature and water stress: Proceedings of an International Symposium, Aug. 13-18, 1992. Ed., C. G. Kuo, pp. 335-346. Taipei, Taiwan: Asian Vegetables Research and Development Center), indicating that more than one mechanism may be responsible for this trait (King et al 2009).

Soybean breeding programs focused in drought tolerance are quite recent, until 1980 no genotypes with agronomic tolerance to drought have been identified. Low genetic variability found in the cultivated specie *Glycine max* and the wild specie *Glycine soybean* is a well-recognized bottleneck in plant breeding. On the other hand, a correct evaluation of resistance grade of a specific genotype to abiotic stress is critical when conventional or molecular plant breeding of any crop. Standardized protocols allow the dissection of a particular phenotype in the biochemical and physiological components. Several methods for phenotyping have been developed in models species as *Arabidopsis thaliana, Medicago truncatula, Brachypodium dystachon*, etc. however, each crop has to be analyzed through a specific phenotyping plan in order to reduce the plant responses not associated with drought stress tolerance mechanisms.

Phenotyping involves measurement of visible attributes that reflect the biological functioning of gene variants (alleles) as affected by the environment. In general, phenotyping for crop improvement via breeding requires that hundreds or thousands of genetic lines are assessed. To date, most phenotyping of secondary traits (i.e., those traits in addition to yield, which is often the primary trait) has involved field assessments of easily scored morphological attributes such as plant height, leaf number, flowering date, and leaf senescence. An important prerequisite for the successful phenotyping of secondary traits is to identify key functional attributes that contribute to drought tolerance.

Criterion for phenotyping should include traits which have a clear-cut and rational explanation for its physiological or molecular function in drought tolerance. Some key traits that satisfy this latter criterion include: (i) favorable stomatal behavior; (ii) rooting depth; (iii) osmotic adjustment and other processes that sustain cell integrity and function; iv) carbohydrates storage and remobilization; and (v) sustained development (as opposed to abortion) of harvested organs. For example, results obtained from soybean phenotyping have showed that a higher sensibility in stomata conductance of leaves from plant subjected to dry soil is a parameter to be selected as drought tolerance marker with impact in water use efficiency (Liu et al./Environmental and Experimental Botany 54 (2005) 33-40).

One of the variables most studied controlling the stomata aperture is the atmospheric relative humidity (RH), stomata is closed under low RH avoiding water loss under dry soil conditions. There are a great number of genes behind the stomata regulation and several signaling pathways in stomata movement have been identified. These components have shown that is possible to modify the stomata response to relative humidity changes and thus the WUE (Liu et al. *Environmental and Experimental Botany* 54 (2005) 33-40). Environmental signals such as light reduction or water availability lead to the reduction of gas interchange promoting the closing of stomata and inhibiting the aperture, both processes are depending of turgor induced by coordinated activation or inhibition of ionic channels present in the guard cell. Together with this mechanism, signaling pathways involving chemical messengers, kinases, phosphatases and phospholipases also have been identified.

Among the molecules with important roles in stomata movement, the hormone abscisic acid (ABA) is definitively the most studied. ABA perception in guard cell triggers a wide complex net of signaling and response pathways.

In spite of the several groups of genes that have been identified as dependent of ABA signaling, few or none of them have proven to be useful as markers for stomata response under drought conditions. Moreover, several transcription factors that regulate stomata aperture have been widely investigated, although the mechanism of how they control stomata movement is not well understood. Identification of new genetic components that control the stomata movement is a valid strategy to improve the response of crops and specially the soybean to drought conditions.

The information generated by the different phenotyping methods are the bases of genotyping methods which lead to identification of genes with potential contribution to drought tolerance in crops. Molecular markers have assisted mapping of genes and quantitative trait locus (QTLs) with agronomic importance in several crops. Developing of molecular tools derived from genomic and post-genomic analysis, including transcriptomic, proteomic and metabolomics, are valuable methods to identify candidate genes associated with drought tolerance.

The complex nature of the mechanisms leading to tolerance to drought and other associated abiotic stresses has made breeding for tolerance largely unsuccessful. Therefore, the identification and functional characterization of new genes and proteins that are involved in the different processes that lead to stress adaptation in tolerant plants has been long needed for designing new strategies for crop improvement.

SUMMARY OF THE INVENTION

In a first aspect, the invention relates to a transgenic plant with an increased abiotic stress tolerance wherein said plant expresses a nucleic acid sequence shown in SEQ ID NO: 1, SEQ ID NO: 2 or a functionally equivalent variant thereof as well as a transgenic plant. Alternatively, the invention relates to a transgenic plant with an increased abiotic stress tolerance wherein said plant expresses a nucleic acid sequence shown in SEQ ID NO:8, SEQ ID NO:11, wherein if said transgenic plant is a soybean plant, then at least one copy of said nucleic acid sequence is found in a location in the genome different from the location where it naturally occurs or is under the control of a promoter which is not the naturally occurring promoter.

In a second aspect, the invention relates to a part of a plant of the invention or a product derived from said plant or from a part thereof.

In a third aspect, the invention relates to a vector comprising (i) a sequence selected from the group consisting of SEQ ID NO: 1, SEQ ID NO: 2, SEQ ID NO:8, SEQ ID NO:11 and a functionally equivalent variant thereof; and (ii) a heterologous promoter sequence.

In a fourth aspect, the invention relates to a host cell comprising the vector of the invention.

In a fifth aspect, the invention relates to a method for producing a transgenic plant having increased abiotic stress tolerance, said method comprising introducing into said plant a sequence selected from the group consisting of SEQ ID NO: 1, SEQ ID NO: 2, SEQ ID NO:8, SEQ ID NO:11 or a functionally equivalent variant thereof wherein if said transgenic plant is a soybean plant, then at least one copy of said nucleic acid sequence is found in a location in the genome different from the location where it naturally occurs or is under the control of a promoter which is not the naturally occurring promoter.

In a sixth aspect, the invention relates to a method for increasing yield and/or growth of a plant under abiotic stress conditions said method comprising increasing the expression of a sequence selected from the group consisting of SEQ ID NO: 1, SEQ ID NO: 2, SEQ ID NO:8, SEQ ID NO:11 or a functionally equivalent variant thereof into a plant wherein if said plant is a soybean plant, then at least one copy of said nucleic acid sequence is found in a location in the genome different from the location where it naturally occurs or is under the control of a promoter which is not the naturally occurring promoter.

In a seventh aspect, the invention relates to a method for increasing abiotic stress tolerance of a plant, which comprises increasing the expression of a sequence selected from the group consisting of SEQ ID NO: 1, SEQ ID NO: 2, SEQ ID NO:8, SEQ ID NO:11 or a functionally equivalent variant thereof into a plant wherein if said plant is a soybean plant, then at least one copy of said nucleic acid sequence is found in a location in the genome different from the location where it naturally occurs or is under the control of a promoter which is not the naturally occurring promoter.

In an eight aspect, the invention relates to the use of a sequence selected from the group consisting of SEQ ID NO: 1, SEQ ID NO: 2, SEQ ID NO:8, SEQ ID NO:11 and a functionally equivalent variant thereof or a vector of the invention for improving plant abiotic stress tolerance wherein if said plant is a soybean plant, then at least one copy of said nucleic acid sequence is found in a location in the genome different from the location where it naturally occurs or is under the control of a promoter which is not the naturally occurring promoter.

In a ninth aspect, the invention relates to a method of identifying a plant having increased abiotic stress tolerance, the method comprising:
  a. detecting a marker genetically linked to a gDNA sequence coding for SEQ ID NO: 5, SEQ ID NO: 7 or a functionally equivalent variant thereof, and b. selecting a plant having said marker,
wherein if said transgenic plant is a soybean plant, then at least one copy of said nucleic acid sequence is found in a location in the genome different from the location where it naturally occurs or is under the control of a promoter which is not the naturally occurring promoter.

In a tenth aspect, the invention relates to a method of producing a plant having increased abiotic stress tolerance or yield relative to a corresponding control plant, the method comprising crossing a plant and selecting a progeny plant having increased abiotic stress tolerance or yield or a progeny plant showing SEQ ID NO: 1, SEQ ID NO: 2 SEQ ID NO:8, SEQ ID NO:11 or a functionally equivalent variant thereof.

DETAILED DESCRIPTION OF THE INVENTION

Figure 1:
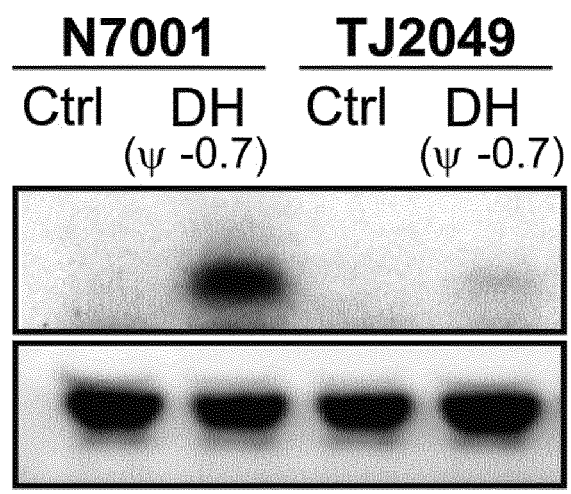
FIG. 1. (A) RNA gel blot analysis of soybean varieties N7001 and TJ2049, subjected to drought conditions that result in a soil water potential of −0.7 MPa. Total RNA was extracted from control (Ctrl) or stressed plants and 10 μg were separated in agarose denaturing gels and transferred to nylon membranes. The expression of a eukaryotic initiation factor iso 4G gene was detected by hybridization of the membrane with a DNA probe corresponding to the coding region of the translation initiation factor, labeled with 32P-dCTP. RNA samples were incubated with ethydium bromide to ensure equal loading in the gel, and shown as rRNA in the figure. (B). RNA gel blot analysis of soybean varieties N7001 and TJ2049, subjected to drought conditions that result in a soil water potential of −0.7 MPa. Total RNA was extracted from control (Ctrl) and stressed plants and 10 μg were separated in agarose denaturing gels and transferred to nylon membranes. The expression of a Sieve Element Occlusion gene was detected by hybridization of the membrane with a DNA probe corresponding to the coding region of the of the GmSEO gene, labeled with 32P-dCTP. RNA samples were incubated with ethydium bromide to ensure equal loading in the gel, and shown as rRNA in the figure.
Figure 1:
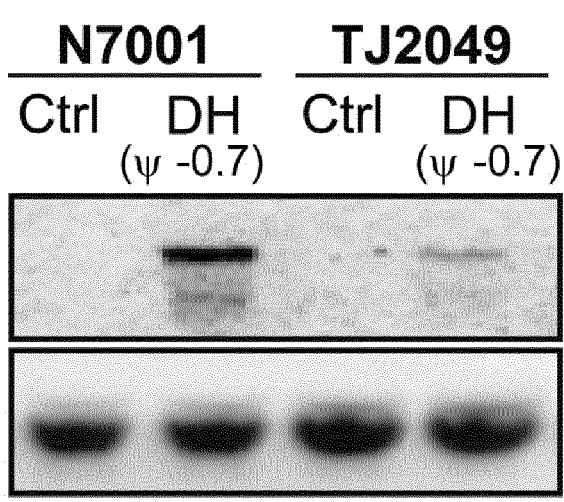

The present inventors have identified and isolated polynucleotide sequences encoding polypeptides from *Glycine max* (soybean) which are suitable for enhancing abiotic stress tolerance and/or yield in plants. It is disclosed for the first time that the soybean genes GmeIFiso4G-1 (Glyma17g08030) and GmSEO (Glyma20g34670) are differentially expressed upon drought stress in soybean varieties that exhibit differences in drought tolerance levels. Furthermore, the present invention describes that the soybean GmeIFiso4G-1 and/or GmSEOs genes are useful for increasing plant tolerance to various abiotic stresses. Embodiments of the present disclosure include methods for producing plants or photosynthetic organisms tolerant to abiotic stress, including tolerances to but not limited to osmotic, salinity, drought or cold stress.

Transgenic Plants

In a first aspect, the invention relates to a transgenic plant with increased abiotic stress tolerance. The transgenic plant is characterized in that it:
(i) it expresses a nucleic acid sequence shown in SEQ ID NO: 1, SEQ ID NO: 2 or a functionally equivalent variant thereof, wherein if said transgenic plant is a soybean plant, then at least one copy of said nucleic acid sequence is found in a location in the genome different from the location where it naturally occurs or is under the control of a promoter which is not the naturally occurring promoter, or
(ii) It expresses. a nucleic acid sequence shown in SEQ ID NO: 8, SEQ ID NO:11 or a functionally equivalent variant thereof, wherein if said transgenic plant is a soybean plant, then at least one copy of said nucleic acid sequence is found in a location in the genome different from the location where it naturally occurs or is under the control of a promoter which is not the naturally occurring promoter.

As used herein the term "transgenic plant" includes plant, plant cell, callus, plant tissue, or plant part or photosynthetic organisms, which have been genetically modified to contain exogenous DNA introduced by non-essentially biological processes, preferably by Agrobacteria transformation. The recombinant construct or a part thereof may be stably integrated into a chromosome, so that it is passed on to successive generations by clonal propagation, vegetative propagation or sexual propagation. The exogenous DNA can be either cDNA or genomic DNA.

As used herein, "plants" means all dicotyledonous or monocotyledonous plants. The term includes the mature plants, seeds, shoots and seedlings, and parts, propagation material, plant organs, tissue, protoplasts, callus and other cultures, for example cell cultures derived from the above, and all other types of associations of plant cells which give functional or structural units. "Mature plants" means plants at any developmental stage beyond the seedling stage. Seedling means a young, immature plant in an early developmental stage.

Plant also comprises annual and perennial dicotyledonous or monocotyledonous plants and includes by way of example, but not by limitation, those of the genera *Glycine, Vitis, Asparagus, Populus, Pennisetum, Lolium, Oryza, Zea, Avena, Hordeum, Secale, Triticum, Sorghum, Saccharum* and *Lycopersicum*.

Plants that can be made to have increased abiotic stress tolerance by practice of the present invention include, but are not limited to, *Acacia*, alfalfa, aneth, apple, apricot, artichoke, arugula, *Asparagus, avocado, banana*, barley, beans, beet, blackberry, blueberry, *broccoli*, brussels sprouts, cabbage, *canola*, cantaloupe, carrot, *cassava*, cauliflower, celery, cherry, cilantro, *Citrus*, clementines, coffee, corn, cotton, cucumber, Douglas fir, eggplant, endive, escarole, *Eucalyptus*, fennel, figs, forest trees, gourd, grape, grapefruit, honey dew, *jicama*, kiwifruit, lettuce, leeks, lemon, lime, Loblolly pine, *mango, melon*, mushroom, nut, oat, okra, onion, orange, an ornamental plant, *Papaya*, parsley, pea, peach, peanut, pear, pepper, persimmon, pine, pineapple, plantain, plum, pomegranate, poplar, potato, pumpkin, quince, *Radiata* pine, radicchio, radish, raspberry, rice, rye, *Sorghum*, Southern pine, soybean, spinach, squash, strawberry, sugarbeet, sugarcane, sunflower, sweet potato, sweetgum, tangerine, tea, tobacco, *tomato*, turf, a vine, watermelon, wheat, yams, and *zucchini*.

In a particular embodiment, the plant is a crop plant. "Crop plant" as used herein refers to plants which are cultivated to produce one or more commercial products. Non-limiting examples of such crops or crop plants include soybean, *canola*, rape, cotton (cottonseeds), sunflower, and grains such as corn, wheat, rice, rye, and the like.

In a particular embodiment, the plant is selected from the group consisting of *Arabidopsis*, soybean, maize, sunflower, *Sorghum, canola*, wheat, alfalfa, cotton, rice, barley, millet, sugar cane, tobacco and switchgrass.

"Stress conditions", as used herein, refers e.g. to stress imposed by the application of chemical compounds (e.g., herbicides, fungicides, insecticides, plant growth regulators, adjuvants, fertilizers), exposure to abiotic stress (e.g., drought, waterlogging, submergence, high light conditions, high UV radiation, increased hydrogen peroxide levels, extreme (high or low) temperatures, ozone and other atmospheric pollutants, soil salinity or heavy metals, hypoxia, anoxia, osmotic stress, oxidative stress, low nutrient levels such as nitrogen or phosphorus etc.) or biotic stress (e.g., pathogen or pest infection including infection by fungi, viruses, bacteria, insects, nematodes, *Mycoplasma* and *Mycoplasma* like organisms, etc.). Stress may also be imposed by hormones such as ABA or compounds influencing hormone activity. "Abiotic stress" means a condition where the plant does not grow under optimal conditions due to drought stress, waterlogging stress, osmotic stress, salt stress, heat stress and cold temperature stress. In a particular embodiment the abiotic stress is selected from the group consisting of osmotic, salinity, drought and cold stress.

The term "increased abiotic stress tolerance" means a higher ability to mitigate the negative effects caused by abiotic stress, by illustrative non limitative example by osmotic, salinity, drought and cold stress compared to non-transgenic plant of the same specie than the transgenic plant. Higher ability refers to an ability more than 50%, more than 60%, more than 70%, more that 80%, more than 90% or more than the ability to mitigate the negative effects of a non-transgenic plant.

"Osmotic stress", as used herein, refers to physiologic dysfunction caused by a sudden change in the solute concentration around a cell, which causes a rapid change in the movement of water across its cell membrane. Osmotic stress reduces growth and productivity of crop plants. The osmotic tolerance of a plant can be measured for example by growing the plant in the presence of mannitol, for example 50 mM and measuring parameters such as plant water relations, growth, nodule development, and symbiotic N2-fixation (SNF), kwon by a person skilled in the art.

"Salinity stress", as used herein refers to a condition where excessive salts in soil solution cause inhibition of plant growth and plant death. Salinity tolerance can be determined by determining the ability to grow in the presence of NaCl for example at 150 mM.

As used herein the term "drought stress" is used interchangeably with water stress. The term "drought stress" as used herein can be induced in plants under conditions where reduced water content in the soil, due to a shortage of rainfall or irrigation, leads to impaired or reduced water absorption by the plant or photosynthetic organism. Water stress may trigger in plants a deterioration of physiological functions of cells, thereby leading to various disorders. While the conditions which induce drought stress may vary depending on the kind of the soil where plants are cultivated, examples of the conditions include but are not limited to: a reduction in the water content in the soil of 15% by weight or less, more severely 10% by weight or less, and still more severely 7.5% by weight or less; or the pF value of the soil of 2.3 or more, more severely 2.7 or more, and still more severely 3.0 or more.

Water stress be recognized or identified by comparing a change in plant phenotypes described in more detail below between plants which have been exposed to water stress conditions and plants which have not been exposed to the same water stress conditions. Water stress in a plant or photosynthetic organism may be indicated by a change in one or more of the following plant phenotypes, which can serve as indicators of the water stress in plants: (1) germination percentage, (2) seedling establishment rate, (3) number of healthy leaves, (4) plant length, (5) plant weight, (6) leaf area, (7) leaf colour, (8) number or weight of seeds or fruits, (9) quality of harvests, (10) flower setting rate or fruit setting rate, (11) chlorophyll fluorescence yield, (12) water content, (13) leaf surface temperature, and (14) transpiration capacity.

Water stress may be quantified as the "intensity of stress" where intensity of stress is represented as following: "Intensity of stress"=100×"any one of plant phenotypes in plants which have not been exposed to water stress"/"the plant phenotype in plants which have been exposed to water".

In a preferred embodiment, the tolerance to drought stress may be calculated by determining the relative water content as disclosed in the experimental part of the present document.

"Cold stress" as used herein refers to a condition where a temperature lower than the plant's optimal growing temperature causes inhibition of plant growth and/or plant death. Cold tolerance can be determined by determining the ability of the plant to grow at a temperature lower than the optimally growing temperature, for example by growing the plant at 4° C.

The transgenic plant of the invention expresses a nucleic acid sequence shown in SEQ ID NO: 1, SEQ ID NO: 2, SEQ ID NO: 8, SEQ ID NO:11 or a functionally equivalent variant thereof.

"Expression" means the transcription and stable accumulation of RNA derived from the polynucleotides of the present invention. Expression may also refer to translation of mRNA into a polypeptide. A person skilled in the art knows routine procedures for measuring the level of expression in a plant of the polynucleotides or polypeptides described herein, such as but not limited to, northern blot, RT-PCR, ELISA, and enzymatic assays where applicable. If enhanced gene expression is desired, it can be attained by using known technical procedures, such as for example, by overproduction of the mRNA encoding the protein or by gene shuffling. One skilled in the art will also know methods available to achieve overproduction of mRNA, for example, by increasing the number of copies of the native gene in a plant, or by introducing into a target plant a construct having a heterologous promoter operably linked to the gene. In a preferred embodiment, expression of the nucleic acid sequence shown in SEQ ID NO: 1, SEQ ID NO: 2, SEQ ID NO: 8, SEQ ID NO:11 in the transgenic plant occurs at levels which are higher than the expression level observed in reference cultivars, such as TJ2049 or William 82. In one embodiment, expression of the SEQ ID NO: 1, SEQ ID NO: 2, SEQ ID NO: 8, SEQ ID NO:11 sequences occur at levels which are at least 2-fold. 4-fold. 6-fold, 8-fold, 10-fold, 20-fold. 30-fold, 40-fold. 50-fold, 60-fold, 80-fold, 90-fold, 100-fold, 500-fold. 1000-fold or more with respect to the expression in the TJ2049 or William 82 cultivars. Methods for determining expression levels of the SEQ ID NO: 1, SEQ ID NO: 2, SEQ ID NO: 8, SEQ ID NO:11 sequences in the transgenic plant and in the reference cultivars are well-known to the person skilled in the art.

SEQ ID NO: 1 as used herein, relates to the cDNA sequence of the gene encoding Glyma17g08030 from soybean cultivar N7001 which corresponds to GmeIFiso4G. The canonical eIF4G factor together with eIF4E and eIF4A factors are subunits of the eIF4F complex, which play an important role in the process of translation initiation. Plants have unique translational characteristics as they have additional isoforms of the eIF4E and eIF4G factors, named eIF(iso)4E and eIF(iso)4G, respectively. The number of these isoforms varies between plant species, soybean has four eIF(iso)4G and two eIF(iso)4E.

SEQ ID NO: 2 as used herein relates to the cDNA sequence of the gene encoding Glyma20g34670 from soybean cultivar N7001, cultivar TJ2079 or cultivar William 82, which corresponds to a member of the family of Sieve Element Occlusion (SEO) proteins. These accumulate predominantly in the phloem of dicotyledonous plants but were initially found in the sieve elements of leguminous plants, forming spindle shaped protein bodies also known as forisomes. These structures consist in protein complexes formed by different SEO proteins, which are capable of forming multimeric complexes that are able to undergo a reversible, calcium-induced conformational change. This can consequently plug and open the sieve elements after wounding and regeneration, thereby preventing the loss of photoassimilates Soybean has 26 genes encoding for SEO proteins, and 5 of them appear to be pseudogenes.

SEQ ID NO:8 as used herein, relates to the genomic DNA sequence of the gene encoding Glyma17g08030 from soybean cultivar N7001 which corresponds to GmeIFiso4G.

SEQ ID NO:11, as used herein, relates to the genomic DNA sequence of the gene encoding Glyma20g34670 from soybean cultivar N7001 which corresponds to a member of the family of Sieve Element Occlusion (SEO) proteins.

"Functionally equivalent variant" of SEQ ID NO: 1, SEQ ID NO: 2, SEQ ID NO: 8, or SEQ ID NO: 11, as used herein, relates to all those sequence by modification, insertion and/or deletion or one or more nucleic acids, whenever the function is substantially maintained. Particularly, any functional part or portion of the polynucleotide sequences, any polynucleotide able to hybridize with SEQ ID NO 1, 2, 8, or 11 or any polynucleotide that encodes an orthologue or paralogue of the proteins codified.

Functionally equivalent variants of SEQ ID NO: 1 also include nucleic acids sequences with a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% with the sequence SEQ ID NO: 1.

Functionally equivalent variants of SEQ ID NO: 2 also include nucleic acids sequences with a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% with the sequence SEQ ID NO:2.

Functionally equivalent variants of SEQ ID NO: 8 also include nucleic acids sequences with a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% with the sequence SEQ ID NO:8.

Functionally equivalent variants of SEQ ID NO: 11 also include nucleic acids sequences with a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% with the sequence SEQ ID NO:11.

As disclosed, a functionally equivalent variant should maintain the function of the SEQ ID NO: 1, SEQ ID NO: 2, SEQ ID NO, 8, or SEQ ID NO: 11. In order to determine if a sequence maintains substantially the function of SEQ ID NO: 1, SEQ ID NO: 2, SEQ ID NO, 8, or SEQ ID NO: 11, the ability of the amino acids sequences encoded by the particular functional equivalent variant of SEQ ID NO: 1, SEQ ID NO: 2, SEQ ID NO, 8, SEQ ID NO:11 in inducing abiotic stress tolerance, particularly water stress tolerance in a plant may be assayed. The tolerance to an abiotic stress may be determined by any method known in the art, for example those described in the experimental part.

In a preferred embodiment, the functionally equivalent variant of SEQ ID NO: 1 is the sequence shown in SEQ ID NO: 3 or the sequence shown in SEQ ID NO: 4.

SEQ ID NO: 3 as used herein, relates to the cDNA sequence of the gene encoding Glyma17g08030 from cultivar TJ2049.

SEQ ID NO: 4 as used herein, relates to the cDNA sequence of the gene encoding Glyma17g08030 from cultivar William 82.

In a preferred embodiment, the functionally equivalent variant of SEQ ID NO: 8 is the sequence shown in SEQ ID NO: 9 or 10.

SEQ ID NO:9 as used herein, relates to the genomic DNA sequence of the gene encoding Glyma17g08030 from soybean cultivar TJ2049 which corresponds to GmeIFiso4G gene.

SEQ ID NO:10 as used herein, relates to the genomic DNA sequence of the gene encoding Glyma17g08030 from soybean cultivar William 82 which corresponds to GmeIFiso4G gene.

In a preferred embodiment, the functionally equivalent variant of SEQ ID NO: 11 is the sequence shown in SEQ ID NO: 12 or 13.

SEQ ID NO:12, as used herein, relates to the genomic DNA sequence of the gene encoding Glyma20g34670 from soybean cultivar TJ2049 which corresponds to GmSEO gene.

SEQ ID NO:13, as used herein, relates to the genomic DNA sequence of the gene encoding Glyma20g34670 from soybean cultivar William 82, which corresponds to GmSEO gene.

In a particular embodiment, the functionally equivalent variant of SEQ ID NO: 1 or 8 encodes for the sequence shown in SEQ ID NO: 5 or 6 or a functionally equivalent variant thereof, and the functionally equivalent variant thereof of SEQ ID NO: 2 or 11 encodes for the sequence shown in SEQ ID NO: 7 or a functionally equivalent variant thereof.

Functionally equivalent variants of SEQ ID NO: 5 or 6 also include amino acids sequences with a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% with the sequence SEQ ID NO:5 or 6.

Functionally equivalent variants of SEQ ID NO: 7 also include amino acids sequences with a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% with the sequence SEQ ID NO:7.

Preferably, variants of SEQ ID NO: 5 or 6 or SEQ ID NO: 7 are (i) polypeptides in which one or more amino acid residues are substituted by a preserved or non-preserved amino acid residue (preferably a preserved amino acid residue) and such substituted amino acid may be coded or not by the genetic code, (ii) polypeptides in which there is one or more modified amino acid residues, for example, residues modified by substituent bonding, (iii) polypeptides resulting from alternative processing of a similar mRNA, (iv) polypeptide fragments and/or (v) polypeptides resulting from SEQ ID NO: 1 fusion or the polypeptide defined in (i) to (iii) with another polypeptide, such as a secretory leader sequence or a sequence being used for purification (for example, His tag) or for detection (for example, Sv5 epitope tag). The fragments include polypeptides generated through proteolytic cut (including multisite proteolysis) of an original sequence. The variants may be post-translationally or chemically modified. Such variants are supposed to be apparent to those skilled in the art.

One skilled in the art will recognize that the values of identity of nucleotide sequences can be appropriately adjusted in order to determine the corresponding sequence identity of two nucleotide sequences encoding the polypeptides of the present invention, by taking into account codon degeneracy, conservative amino acid substitutions, and reading frame positioning.

In the context of the present invention "conservative amino acid changes" and "conservative amino acid substitution" are used synonymously invention. "Conservative amino acid substitutions" refers to the interchangeability of residues having similar side chains, and mean substitutions of one or more amino acids in a native amino acid sequence with another amino acid(s) having similar side chains, resulting in a silent change that does not alter function of the protein. Conserved substitutes for an amino acid within a native amino acid sequence can be selected from other members of the group to which the naturally occurring amino acid belongs. For example, a group of amino acids having aliphatic side chains includes *Glycine*, alanine, valine, leucine, and isoleucine; a group of amino acids having aliphatic-hydroxyl side chains includes serine and threonine; a group of amino acids having amide-containing side chains includes asparagine and glutamine; a group of amino acids having aromatic side chains includes phenylalanine, tyrosine, and tryptophan; a group of amino acids having basic side chains includes lysine, arginine, and histidine; and a group of amino acids having sulfur-containing side chains includes cysteine and methionine. In some embodiments of the invention, preferred conservative amino acids substitutions are: valine-leucine, valine-isoleucine, phenylalanine-tyrosine, lysine-arginine, alanine-valine, aspartic acid-glutamic acid, and asparagine-glutamine. Thus, the invention refers to functionally equivalents variants of SEQ ID NO: 1 or 2 coding for a structurally homologous polypeptides that are also functional homologues of SEQ ID NO: 5 or 6 or 7; and that have an amino acid sequence differing in one or more amino acids with the sequence given by SEQ ID NO: 5 or 6 or 7 as the result of one or more conservative amino acid substitutions. It is well known in the art that one or more amino acids in a polypeptide sequence can be substituted with at least one other amino acid having a similar charge and polarity such that the substitution/s result in a silent change in the modified polypeptide that does not alter its function relative to the function of the non-modified sequence. The invention refers to any polypeptide sequence differing in one or more amino acids, either as a result of conserved or non-conserved substitutions, and/or either as a result of sequence insertions or deletions, relative to the sequence given by SEQ ID NO: 5, 6 or 7, as long as said further provided polypeptide sequence has the same or similar or equivalent function or effect in a plant as the function or effect herein demonstrated for SEQ ID NO: 5, 6 or 7 and that corresponds to increased tolerance to abiotic stresses such as one or more of drought stress, osmotic stress, salinity stress, heat stress, and/or cold stress, and/or that corresponds to increased plant yield.

By "codon degeneracy" it is meant divergence in the genetic code enabling variation of the nucleotide sequence without affecting the amino acid sequence of an encoded polypeptide. A person skilled in the art is well aware of the codon-bias exhibited by a specific host cell in using nucleotide codons to specify a given amino acid residue. Thus, for ectopic expression of a gene in a host cell, it is desirable to design or synthesize the gene in a way such that its frequency of codon usage approaches the frequency of codon usage of the host cell as described in a codon usage table.

The terms "identity", "identical" or "percent identity" in the context of two or more amino acid, or nucleotide sequences, refer to two or more sequences or subsequences that are the same or have a specified percentage of amino acid or nucleotide residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

The percentage of sequence identity may be determined by comparing two optimally aligned sequences over a comparison window. The aligned sequences may be polynucleotide sequences or polypeptide sequences. For optimal alignment of the two sequences, the portion of the polynucleotide or amino acid sequence in the comparison window may comprise insertions or deletions (i.e., gaps) as compared to the reference sequence (that does not comprise insertions or deletions). The percentage of sequence identity is calculated by determining the number of positions at which the identical nucleotide residues, or the identical amino acid residues, occurs in both compared sequences to yield the number of matched positions, then dividing the number of matched positions by the total number of positions in the window of comparison and multiplying the result by 100 to yield the percentage of sequence identity. Sequence identity between two polypeptide sequences or two polynucleotide sequences can be determined, for example, by using the Gap program in the WISCONSIN PACKAGE version 10.0-UNIX from Genetics Computer Group, Inc. based on the method of Needleman and Wunsch (J. Mol. Biol. 48:443-453, 1970) using the set of default parameters for pairwise comparison (for amino acid sequence comparison: Gap Creation Penalty=8, Gap Extension Penalty=2; for nucleotide sequence comparison: Gap Creation Penalty=50; Gap Extension Penalty=3), or using the TBLASTN program in the BLAST 2.2.1 software suite (Altschul et al., Nucleic Acids Res. 25:3389-3402), using BLOSUM62 matrix (Henikoff and Henikoff, Proc. Natl. Acad. Sci. U.S.A. 89:10915-10919, 1992) and the set of default parameters for pair-wise comparison (gap creation cost=11, gap extension cost=1).

The percentage of sequence identity between polypeptides and their corresponding functions may be determined, for example, using a variety of homology based search algorithms that are available to compare a query sequence, such as the polypeptides SEQ ID NO: 5 or 7, to a protein database, including for example, BLAST, FASTA, and Smith-Waterman. BLASTX and BLASTP algorithms may be used to provide protein function information. A number of values are examined in order to assess the confidence of the function assignment. Useful measurements include "E-value" (also shown as "hit_p"), "percent identity", "percent query coverage", and "percent hit coverage". In BLAST, the E-value, or the expectation value, represents the number of different alignments with scores equivalent to or better than the raw alignment score, S, that are expected to occur in a database search by chance. Hence, the lower the E value, the more significant the match. Since database size is an element in E-value calculations, the E-values obtained by doing a BLAST search against public databases, such as GenBank, have generally increased over time for any given query/entry match. Thus, in setting criteria for confidence of polypeptide function prediction, a "high" BLASTX match is considered as having an E-value for the top BLASTX hit of less than 1E-30; a medium BLASTX is considered as having an E-value of 1E-30 to 1E-8; and a low BLASTX is considered as having an E-value of greater than 1E-8. Percent identity refers to the percentage of identically matched amino acid residues that exist along the length of that portion of the sequences which is aligned by the BLAST algorithm. In setting criteria for confidence of polypeptide function prediction, a "high" BLAST match is considered as having percent identity for the top BLAST hit of at least 70%; a medium percent identity value is considered from 35% to 70%; and a low percent identity is considered of less than 35%. Of particular interest in protein function assignment is the use of combinations of E-values, percent identity, query coverage and hit coverage. Query coverage refers to the percent of the query sequence that is represented in the BLAST alignment, whereas hit coverage refers to the percent of the database entry that is represented in the BLAST alignment. For the purpose of defining the polypeptides functionally covered by the present invention, the function of a polypeptide is deduced from the function of a protein homolog, such as SEQ ID NO: 5 or 7, wherein a polypeptide of the invention is one that either (1) results in hit_p<1e-30 or % identity>35% AND query_coverage>50% AND hit_coverage>50%, or (2) results in hit_p<1e-8 AND query_coverage>70% AND hit_coverage>70%. The transgenic plant of the invention may be obtained by any method known by a skilled person in the art, and particularly by a method described in the present invention.

Part of a Plant

In another aspect, the invention relates to a part of a plant of the invention or a product derived from said plant or from a part thereof.

"Part of a plant", as used herein relates to a specific part of a plant such as leaves, pollen, embryos, cotyledons, hypocotyl, meristematic cells, roots, root tips, pistils, anthers, flowers, stems, endosperm, grain, fruit or bud.

"Product derived from the plant or the part thereof" refers to any product obtained from processing a plant or a part of the plant of the invention from physical modification and/or chemistry; for a non-limiting illustrative purposes flour, Semolina, oil, syrup, starch or fecula.

All the terms and embodiments previously described are equally applicable to this aspect of the invention.

Vector of the Invention

In a third aspect the invention relates to a vector comprising (i) a sequence selected from the group consisting of SEQ ID NO: 1, SEQ ID NO: 2, SEQ ID NO: 8, SEQ ID NO:11 and a functionally equivalent variant thereof; and (ii) a heterologous promoter sequence.

As used herein, the term "vector" refers to a nucleic acid molecule capable of transporting another nucleic acid to which it has been linked. One type of vector is a "plasmid," which refers to a circular double stranded DNA loop into which additional DNA segments can be ligated.

In preparing the constructs (vectors) of the present invention, the various components of the construct or fragments thereof will normally be inserted into a convenient cloning vector, e.g., a plasmid that is capable of replication in a bacterial host, e.g., E. coli. Numerous cloning vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A plasmid expression vector suitable for the introduction of a polynucleotide encoding a polypeptide of present invention using electroporation or particle-gun mediated transformation is composed of the following: a promoter that is constitutive, inducible, or tissue-specific; an intron that provides a splice site to facilitate expression of the gene, such as the maize Hsp70 intron (U.S. Pat. No. 5,593,874, herein incorporated by reference in its entirety); and a 3' polyadenylation sequence such as the nopaline synthase 3' sequence (nos 3; Fraley et al., Proc. Natl. Acad. Sci. USA 80: 4803-4807, 1983). This expression cassette may be assembled on high copy replicons suitable for the production of large quantities of DNA.

An example of a useful Ti plasmid cassette vector for plant transformation is pMON17227. This vector is described in U.S. Pat. No. 5,633,435, herein incorporated by reference in its entirety, and contains a gene encoding an EPSPS enzyme with glyphosate resistance (herein referred to as aroA:CP4), that is an excellent selection marker gene for many plants. The gene is fused to the Arabidopsis EPSPS chloroplast transit peptide (At. EPSPS:CTP2) and expressed from the Figwort mosaic virus (P-FMV) promoter as described therein.

The exogenous polynucleotides of the invention may be transferred into a plant cell by the use of a recombinant DNA construct or vector designed for such a purpose, and herein referred to as "construct". The present invention also provides a construct for producing transgenic plants such as transgenic crop plants, wherein the construct comprises a structural polynucleotide sequence encoding a polypeptide of the present invention. Methods that are well known to those skilled in the art, in addition to those presented in the Examples of this disclosure, may be used to prepare the constructs of the present invention. These methods include in vitro recombinant DNA techniques, synthetic techniques, and in vivo genetic recombination. Such techniques are described in Sambrook J, Fritschi E F and Maniatis T (1989) *Molecular cloning: a laboratory manual*, Cold Spring Harbor Laboratory Press, New York. Assembly of constructs is done by standard molecular biology techniques also as described in Sambrook et al.

In a preferred embodiment, the vector pENTR2B or pMDC7 is used in the present invention.

The vector of the invention comprises a heterologous promoter sequence.

Promoters that are known or are found to cause transcription of DNA in plant cells can be used in the present invention. Such promoters may be obtained from a variety of sources such as plants and plant viruses. A number of promoters, including constitutive promoters, inducible promoters and tissue-specific promoters, that are active in plant cells have been described in the literature. It is preferred that the particular promoter selected should be capable of causing sufficient expression to result in the production of an effective amount of a polypeptide to cause the desired phenotype. In addition to promoters that are known to cause transcription of DNA in plant cells, other promoters may be identified for use in the current invention by screening a plant cDNA library for genes that are selectively or preferably expressed in the target tissues and then determine the promoter regions.

In the context of the present invention the term "promoter sequence" means a sequence responsible for driving transcription (i.e., RNA synthesis) by binding to specialized nuclear proteins called transcription factors. The polynucleotides encoding the polypeptide of the present invention may be combined with other non-native, or "heterologous" sequences in diverse manners. By "heterologous" sequences it is meant any sequence that is not naturally found joined to the polynucleotide sequences encoding the polypeptides of the present invention, such as, for example, combinations of polynucleotide sequences from the same plant that are not naturally found joined together, or combinations of polynucleotide sequences that originate from two different species. For example, a polynucleotide encoding a polypeptide of the invention may be combined in an operably linked manner with a promoter not naturally driving the expression of the polynucleotide, such that said promoter artificially drives the expression of the polynucleotide. Thus, the term "heterologous promoter sequence" means a promoter sequence foreign to the cell.

The term "inducible promoter" means a regulatory sequence that causes conditional expression of a structural nucleotide sequence under the influence of changing environmental conditions, or developmental conditions. The term "tissue-specific promoter" means a regulatory sequence that causes transcriptions or enhanced transcriptions of DNA in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One skilled in the art will recognize that a tissue-specific promoter may drive expression of operably linked DNA molecules in tissues other than the target tissue. Thus, as used herein a tissue-specific promoter is one that drives expression preferentially in the target tissue, but may also lead to some expression in other tissues as well. The DNA construct of the present invention can, in one embodiment, contain a promoter which causes the over-expression of the polypeptide of the present invention, where "over-expression" means the expression of a polypeptide either not normally present in the host cell, or present in said host cell at a higher level than that normally expressed from the endogenous gene encoding said polypeptide. Promoters that can cause the over-expression of the polypeptide of the present invention are generally known in the art.

In a preferred embodiment the heterologous inducible promoter is β-estradiol inducible promoter. In a more preferred embodiment the heterologous inducible promoter is the β-estradiol inducible promoter as disclosed in SEQ ID NO: 16.

A variety of promoters specifically active in vegetative tissues, such as leaves, stems, roots and tubers, can be used to express the polynucleotides of the present invention. Examples of tuber-specific promoters include, but are not limited to the class I and II patatin promoters (Bevan et al., EMBO J. 8:1899-1906, 1986; Koster-Topfer et al., Mol Gen Genet. 219:390-396, 1989; Mignery et al., Gene. 62:27-44, 1988; Jefferson et al., Plant Mol. Biol. 14: 995-1006, 1990). Examples of leaf-specific promoters include but are not limited to the ribulose biphosphate carboxylase (RBCS or RuBISCO) promoters (see, e.g., Matsuoka et al., Plant J. 6:311-319, 1994); the light harvesting chlorophyll a/b binding protein gene promoter (see, e.g., Shiina et al., Plant Physiol. 115:477-483, 1997). Examples of root-specific promoters include, but are not limited to, the promoter for the acid chitinase gene (Samac et al., Plant Mol. Biol. 25:587-596, 1994); the root specific subdomains of the CaMV35S promoter that have been identified (Lam et al., Proc. Natl. Acad. Sci. (U.S.A.) 86:7890-7894, 1989).

The term "constitutive promoter" means a regulatory sequence that causes expression of a structural nucleotide sequence in most cells or tissues at most times.

Constitutive promoters are active under most environmental conditions and states of development or cell differentiation. A variety of constitutive promoters are well known in the art. Examples of constitutive promoters that are active in plant cells include but are not limited to the nopaline synthase (NOS) promoters; the cauliflower mosaic virus (P-CaMV) 19S and 35S (U.S. Pat. No. 5,858,642); the figwort mosaic virus promoter (P-FMV, U.S. Pat. No. 6,051,753); and actin promoters, such as the rice actin promoter (P-Os.Act1, U.S. Pat. No. 5,641,876). In a preferred embodiment, the heterologous promoter is *Arabidopsis* ubiquitin promoter. In a more preferred embodiment, the heterologous promoter is the *Arabidopsis* ubiquitin promoter as disclosed in SEQ ID NO: 17.

Promoters derived from genes encoding embryonic storage proteins, which includes the gene encoding the 2S storage protein from *Brassica napus* (Dasgupta et al., Gene 133:301-302, 1993); the gene encoding oleosin 20 kDa from *Brassica napus* (GenBank No. M63985); the genes encoding oleosin A (GenBank No. U09118) and oleosin B (GenBank No. U09119) from soybean; the gene encoding oleosin 18 kDa from maize (GenBank No. J05212, Lee, Plant Mol. Biol. 26:1981-1987, 1994); and the gene encoding low molecular weight sulphur rich protein from soybean (Choi et al., Mol. Gen. Genet. 246:266-268, 1995), can also be used. Promoters derived from zein encoding genes (including the 15 kDa, 16 kDa, 19 kDa, 22 kDa, 27 kDa, and gamma genes, Pedersen et al., Cell 29:1015-1026, 1982) can be also used. The zeins are a group of storage proteins found in maize endosperm.

In a preferred embodiment, the promoter is a constitutive promoter or a dehydration inducible promoter. Illustrative-non limitative dehydration inducible promoters that can be used according to the invention are ERD1 from *Arabidopsis*, the rice genome-derived SalT promoter, the OsNAC6 promoter.

Yet, the DNA construct of the present invention can, in another embodiment, contain a promoter which causes the ectopic expression of the polypeptide of the invention, where "ectopic expression" means the expression of a polypeptide in a cell type other than a cell type in which the polypeptide is normally expressed; at a time other than a time at which the polypeptide is normally expressed; or at an expression level other than the level at which the polypeptide is normally expressed. Promoters that can cause ectopic expression of the polypeptide of the present invention are generally known in the art. The expression level or pattern of the promoter of the DNA construct of the present invention may be modified to enhance its expression. Methods known to those of skill in the art can be used to insert enhancing elements (for example, subdomains of the CaMV 35S promoter, Benfey et. al, 1990 EMBO J. 9: 1677-1684) into the 5' sequence of genes. In one embodiment, enhancing elements may be added to create a promoter that encompasses the temporal and spatial expression of the native promoter of the polynucleotide of the present invention but have altered levels of expression as compared to the native levels of expression. Similarly, tissue specific expression of the promoter can be accomplished through modifications of the 5' region of the promoter with elements determined to specifically activate or repress gene expression (for example, pollen specific elements, Eyal et al., 1995 Plant Cell 7: 373-384).

It is preferred that the promoter allows expression of the sequences forming part of the vectors according to the invention to levels which are at least 2-fold, 4-fold, 6-fold, 8-fold, 10-fold, 20-fold. 30-fold, 40-fold. 50-fold, 60-fold, 80-fold, 90-fold, 100-fold, 500-fold. 1000-fold or more, higher with respect to the expression achieved under the promoter found in the native TJ2049 or William 82 cultivars.

In one embodiment of this aspect increasing the expression within the plant of a polynucleotide comprises increasing the activity of the endogenous promoter, and/or altering the activity of one or more endogenous regulatory nucleic acid or protein sequences, controlling the expression of the nucleic acid sequence of anyone of i)-vi). Different procedures well known in the art are useful to increase or decrease the activity of endogenous promoters and other regulatory sequences. Non-limiting examples of these procedures include random mutagenesis, and homologous recombination procedures to modify endogenous promoter or regulatory sequences. Hence, for instance, the endogenous expression of SEQ ID NO: 1, SEQ ID NO: 2. SEQ ID NO: 8, SEQ ID NO:9, SEQ ID NO:11 and/or SEQ ID NO:12 can be increased in soybean by increasing the activity of the endogenous promoter by homologous recombination. Alternatively, mutagenesis of the endogenous promoter can lead to increased activity.

The vector of the invention can also comprise additional sequences, such as translation leader sequence, 3' non-translated sequences, regulatory sequences or a marker sequence.

The "translation leader sequence" means a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and *petunia* heat shock protein leaders, plant virus coat protein leaders, and plant rubisco gene leaders among others (Turner and Foster, Molecular Biotechnology 3:225, 1995).

The "3' non-translated sequences" or "3' termination region" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (nos 3; Fraley et al., Proc. Natl. Acad. Sci. USA 80: 4803-4807, 1983). Ingelbrecht et al. exemplify the use of different 3' non-translated sequences (Plant Cell 1:671-680, 1989).

"Regulatory sequences" means polynucleotide molecules located upstream (5' non-coding sequences), within, or downstream (3' non-translated sequences) of a structural polynucleotide sequence, and that influence the transcription, RNA processing or stability, or translation of the associated structural polynucleotide sequence. Regulatory sequences may include promoters, translation leader sequences, introns, and polyadenylation recognition sequences.

The vector of the present invention will typically comprise a selectable marker that confers a selectable phenotype on plant cells. Selectable markers may also be used to select for plants or plant cells that contain the exogenous polynucleic acid molecules encoding polypeptides of the present invention. The marker may encode biocide resistance, antibiotic resistance (e.g., kanamycin, G418, bleomycin, hygromycin, etc.), or herbicide resistance (e.g., glyphosate, glufosinate, etc.). Examples of selectable markers include, but are not limited to, a neo gene that codes for kanamycin resistance and can be selected for using kanamycin, G418, etc.; a bar gene that codes for bialaphos resistance; a mutant EPSP synthase gene that encodes glyphosate resistance; a nitrilase gene that confers resistance to bromoxynil a mutant acetolactate synthase gene (ALS) that confers imidazolinone or sulphonylurea resistance, and a methotrexate resistant DHFR gene. In a preferred embodiment the selectable marker is hygromycin resistance.

In addition to using a selectable marker, it may be desirable to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. One preferred such assay entails the use of the gene encoding beta-glucuronidase (GUS) of the uidA locus of *E. coli* as described by Jefferson et al., (*Biochem. Soc. Trans*. 15, 17-19 (1987) to identify transformed cells, referred to herein as GUS:1.

All the terms and embodiments previously described are equally applicable to this aspect of the invention.

Host Cell

In another aspect the invention relates to a host cell comprising a vector as described previously.

The term "host cell" is used such that it refers not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic (e.g., *E. coli*) or eukaryotic cell (e.g., yeast or plant cells).

In a preferred embodiment, the host cell is a bacterial cell, such as *Agrobacterium tumefaciens*.

In another preferred embodiment, the host cell is an isolated plant cell.

Once adequate numbers of cells containing the exogenous polynucleotide encoding polypeptides from the present invention are obtained, the cells can be cultured, and then regenerated into whole plants. Such regeneration techniques rely on manipulation of certain phytohormones in a tissue culture growth medium, typically relying on a biocide and/or herbicide marker that has been introduced together with the desired nucleotide sequences. Regeneration techniques are described generally in Klee et al., Ann. Rev. Plant Phys. 38:467-486 (1987). The development or regeneration of transgenic crop plants containing the exogenous polynucleotide that encodes a polypeptide of interest is well known in the art. Preferably, the regenerated plants are self-pollinated to provide homozygous transgenic crop plants. Otherwise, pollen obtained from the regenerated plants is crossed to seed-grown plants of agronomically important lines. Conversely, pollen from plants of these important lines is used to pollinate regenerated plants. Following DNA transfer and regeneration, putatively transformed plants may also be evaluated, for instance using Southern analysis, for the presence of the gene of interest, copy number and/or genomic organization. Additionally or alternatively, the expression levels of the newly introduced DNA may be monitored using Northern and/or Western analysis, both techniques being well known to persons having ordinary skill in the art.

All the terms and embodiments previously described are equally applicable to this aspect of the invention.

Method for Producing a Transgenic Plant Having Increased Abiotic Stress Tolerance In another aspect, the invention refers to a method for producing a transgenic plant having increased abiotic stress tolerance, said method comprising introducing into said plant a sequence selected from the group consisting of SEQ ID NO: 1, SEQ ID NO: 2 or a functionally equivalent variant thereof. Alternatively, the invention refers to a method for producing a transgenic plant having increased abiotic stress tolerance, said method comprising introducing into said plant a sequence selected from the group consisting of SEQ ID NO: 8, SEQ ID NO:11 or a functionally equivalent variant thereof. In a preferred embodiment, wherein if said transgenic plant is a soybean plant, then at least one copy of said nucleic acid sequence is found in a location in the genome different from the location where it naturally occurs or is under the control of a promoter which is not the naturally occurring promoter.

In a particular embodiment, the abiotic stress is selected from the group consisting of osmotic, salinity, drought or cold stress.

The methods for producing a plant having increased abiotic stress tolerance, may be applicable to the whole plant or organism or a part of a plant, for example in an organ, tissue, a cell or a part of a plant cell, for example in an organelle, which comprises introducing into, and expressing in, the plant or plant cell a nucleic acid sequence selected from the group consisting of SEQ ID NO: 1, SEQ ID NO: 2, SEQ ID NO: 8, SEQ ID NO:11 or a functionally equivalent variant thereof The polynucleotides of the present invention introduced into plant cells can be either chromosomally integrated or organelle-localized.

The term "introduction" or "transformation" as referred to herein encompasses the transfer of an exogenous polynucleotide into a host cell, irrespective of the method used for transfer.

A variety of methods (Keown et al., *Methods in Enzymology* 185, 527(1990)) are available for the introduction of a desired construct into a plant or organism, which is referred to as transformation (or transduction or transfection). Thus, the DNA or RNA can be introduced for example, directly by means of microinjection or by bombardment with DNA-coated microparticles. Also, it is possible to chemically permeabilize the cell, for example using polyethylene glycol, so that the DNA can reach the cell by diffusion. The DNA can also be introduced into the cell by means of protoplast fusion with other DNA-comprising units such as minicells, cells, lysosomes or liposomes. A further suitable method of introducing DNA is electroporation, where the cells are reversibly permeabilized by means of an electrical pulse.

In plants, the above-described methods for the transformation and regeneration of plants from plant tissue or plant cells are exploited for the purposes of transient or stable transformation. Suitable methods are mainly protoplast transformation by means of polyethylene-glycol-induced DNA uptake, the biolistic method with the gene gun, known as the particle bombardment method, electroporation, the incubation of dry embryos in DNA-comprising solution, and microinjection.

Transformation may also be effected by bacterial infection by means of *Agrobacterium tumefaciens* or *Agrobacterium rhizogenes*. The methods are described for example in Horsch et al. Science 225, 1229 (1985).

If agrobacteria are used for transformation, the expression cassette may be integrated into specific plasmids, which may either be a shuttle or intermediate vector or a binary vector. If a Ti or Ri plasmid is used for the transformation, at least the right border, but in most cases both the right and the left border, of the Ti or Ri plasmid T-DNA as flanking region is linked with the expression cassette to be introduced.

Binary vectors are capable of replicating in a variety of organisms including but not limited to *E. coli* and in *agrobacterium*. As a rule, they comprise a selection marker gene and a linker or polylinker flanked by the right and left T-DNA border sequence. They can be transformed directly into *agrobacterium* (Holsters et al., *Mol. Gen. Genet*. 163, 181 (1978)). The selection marker gene, for example the nptII gene, which mediates resistance to kanamycin, permits transformed agrobacteria to be selected. The *agrobacterium* which, in the present case, acts as the host organism should already comprise a helper Ti plasmid with the vir region, which is required for transferring the T-DNA to the plant cell. An *agrobacterium* thus transformed can be used for transforming plant cells. The use of T-DNA for the transformation of plant cells has been studied and described in great detail (EP 120 516; Hoekema, in "The Binary Plant Vector System", *Offsetdrukkerij Kanters B. V.*, Alblasserdam, Chapter V; An et al. EMBO J. 4, 277 (1985)). Various binary vectors are known and in some cases commercially available, such as, for example, pBI101.2 or pBIN19 (Clontech Laboratories, Inc. USA). In a preferred embodiment, *Agrobacterium*-mediated floral dip transformation method is used.

In the event that DNA or RNA is injected or electroporated into plant cells, the plasmid used need not meet particular requirements. Simple plasmids such as those from the pUC series may be used. If intact plants are to be regenerated from the transformed cells, it is necessary for an additional selection marker gene to be located on the plasmid.

Stably transformed cells, i.e. those which comprise the introduced DNA integrated into the DNA of the host cell, can be distinguished from untransformed cells when a selection marker is constituent of the introduced DNA (McCormick et al, *Plant Cell Reports* 5, 81 (1986)). For example, any gene which is capable of mediating a resistance to antibiotics or herbicides (such as kanamycin, G 418, bleomycin, hygromycin or phosphinothricin) may act as a marker. Transformed cells which express such a marker gene are capable of surviving in the presence of concentrations of a suitable antibiotic or herbicide which destroy an untransformed wildtype. Examples include the bar gene, which mediates resistance to the herbicide phosphinothricin (Rathore et al., *Plant Mol. Biol.* 21 (5), 871 (1993)), the nptII gene, which mediates resistance to kanamycin, the hpt gene, which mediates resistance to hygromycin, or the EPSP gene, which mediates resistance to the herbicide glyphosate. The resulting plants can be bred and hybridized in the customary manner. Two or more generations should be cultivated in order to ensure that the genomic integration is stable and hereditary.

Additional methods may be described in Jones et al. ("Techniques for Gene Transfer", in "*Transgenic Plants*", Vol. 1, *Engineering and Utilization*, edited by Kung S. D. and Wu R., Academic Press, p. 128-143 (1993), and in Potrykus, *Annu. Rev. Plant Physiol. Plant Molec. Biol.* 42, 205 (1991)). It is preferred to clone the construct to be expressed into a vector which is suitable for transforming *Agrobacterium tumefaciens*, for example into pBin 19 (Bevan et al., *Nucl. Acids Res.* 12, 8711 (1984)).

When a transformed plant cell has been generated, an intact plant can be obtained using methods known to one skilled in the art. An example of a starting material used here are callus cultures. The formation of shoot and root from this as yet undifferentiated cell biomass can be induced in a known manner. The plantlets obtained can be planted out and bred.

A person skilled in the art also knows methods for regenerating plant parts and intact plants from plant cells. For example, methods described by Fennell et al., *Plant Cell Rep*, 11, 567 (1992); Stoeger et al., *Plant Cell Rep.* 14, 273 (1995); Jahne et al., *Theon. Appl. Genet.* 89, 525 (1994), are used for this purpose.

A transgenic plant formed using *Agrobacterium* transformation, electroporation or other methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous chimer molecule-encoding gene segregates independently during mitosis and meiosis.

After transgenic plants are obtained by one of the methods described above, it will be necessary to screen individual transgenic plants for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the polypeptide encoded by the gene being expressed. Alternatively, one could establish assays that specifically determine the increase in abiotic stress tolerance. A preferred method will be one that allows large numbers of samples to be processed rapidly, since it may be expected that a large number of transformants will be negative for the desired phenotype.

All the terms and embodiments previously described are equally applicable to this aspect of the invention.

A Method for Increasing Yield and/or Growth of a Plant Under Abiotic Stress Conditions In another aspect the invention refers to a method for increasing yield and/or growth of a plant under abiotic stress conditions said method comprising increasing the expression of a sequence selected from the group consisting of SEQ ID NO: 1, SEQ ID NO: 2, SEQ ID NO: 8, SEQ ID NO:11 or a functionally equivalent variant thereof in said plant, wherein if said plant is a soybean plant, then at least one copy of said nucleic acid sequence is found in a location in the genome different from the location where it naturally occurs or is under the control of a promoter which is not the naturally occurring promoter.

In a particular embodiment, the increasing of the expression of a sequence selected from the group consisting of SEQ ID NO: 1, SEQ ID NO: 2, SEQ ID NO: 8, SEQ ID NO:11 or a functionally equivalent variant thereof is obtained by introducing into said plant a sequence selected from the group consisting of SEQ ID NO: 1, SEQ ID NO: 2, SEQ ID NO: 8, SEQ ID NO:11 or a functionally equivalent variant thereof. The introduction of said sequences may be performed as previously described.

The terms "increase", "improve" or "enhance" are interchangeable. Yield or growth for example is increased by at least a 3%, 4%, 5%, 6%, 7%, 8%, 9% or 10%, preferably at least 15% or 20%, more preferably 25%, 30%, 35%, 40% or 50% or more in comparison to a control plant. The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" of a plant may relate to vegetative biomass (root and/or shoot biomass), to reproductive organs, and/or to propagules (such as seeds) of that plant. Thus, according to the invention, yield comprises one or more of and can be measured by assessing one or more of: increased seed yield per plant, increased seed filling rate, increased number of filled seeds, increased harvest index, increased number of seed capsules/pods, increased seed size, increased growth or increased branching, for example inflorescences with more branches. Preferably, yield comprises an increased number of seed capsules/pods and/or increased branching. Yield is increased relative to control plants. In a preferred embodiment, yield is increased in a plant species encoding SEQ ID NO: 1, SEQ ID NO: 2, SEQ ID NO: 8, SEQ ID NO:11 or a functionally equivalent variant thereof, wherein if said transgenic plant is a soybean plant, then at least one copy of said nucleic acid sequence is found in a location in the genome different from the location where it naturally occurs or is under the control of a promoter which is not the naturally occurring promoter, relative to a control plant of the same species. As disclosed herein, "control plants" are plants that do not express SEQ ID NO: 1, SEQ ID NO: 2, SEQ ID NO: 8, SEQ ID NO:11 or a functionally equivalent variant thereof as previously indicated.

Growth of a plant refers to an increasing in the length, thickness or weight of any part of a plant, including a germination period, a vegetative growing period, a reproductive growing period and a harvesting period.

All the terms and embodiments previously described are equally applicable to this aspect of the invention.

A Method for Increasing Abiotic Stress Tolerance of a Plant

In another aspect the invention refers to a method for increasing abiotic stress tolerance of a plant, which comprises increasing the expression of a sequence selected from the group consisting of SEQ ID NO: 1, SEQ ID NO: 2, SEQ ID NO: 8, SEQ ID NO:11 or a functionally equivalent variant thereof in said plant, wherein if said plant is a soybean plant, then at least one copy of said nucleic acid sequence is found in a location in the genome different from the location where it naturally occurs or is under the control of a promoter which is not the naturally occurring promoter.

In a particular embodiment, the increasing of the expression of a sequence selected from the group consisting of SEQ ID NO: 1, SEQ ID NO: 2, SEQ ID NO: 8, SEQ ID NO:11 or a functionally equivalent variant thereof is obtained by introducing into said plant a sequence selected from the group consisting of SEQ ID NO: 1, SEQ ID NO: 2, SEQ ID NO: 8, SEQ ID NO:11 or a functionally equivalent variant thereof. The introduction of said sequences may be performed as previously described.

In a particular embodiment the abiotic stress is selected from the group consisting of osmotic, salinity, drought or cold stress.

All the terms and embodiments previously described are equally applicable to this aspect of the invention.

Uses of Sequences and Vector

The invention also relates to the use of a sequence selected from the group consisting of SEQ ID NO: 1, SEQ ID NO: 2, SEQ ID NO: 8, SEQ ID NO:11 and a functionally equivalent variant thereof or a vector according as described previously for improving plant abiotic stress tolerance wherein if said plant is a soybean plant, then at least one copy of said nucleic acid sequence is found in a location in the genome different from the location where it naturally occurs or is under the control of a promoter which is not the naturally occurring promoter.

"Improving" as used herein, refers to any measurable increased plant abiotic stress tolerance.

In a particular embodiment the abiotic stress is selected from the group consisting of osmotic, salinity, drought or cold stress.

All the terms and embodiments previously described are equally applicable to this aspect of the invention.

Method of Producing a Plant Having Increased Abiotic Stress Tolerance or Yield

It is demonstrated in the present disclosure that expression of the GmeIFiso4G-1 and the GmSEO N7001 alleles are associated with increased tolerance to drought of this cultivar relative to the sensitive cultivar TJ2049 where the two corresponding sequences are not expressed. In addition, it is shown that the heterologous expression of the SEQ ID NO: 1 and SEQ ID NO: 2 corresponding to the cDNA of the gene encoding GmeIFiso4G-1 and the cDNA of the gene encoding GmSEO N7001, respectively, in *A. thaliana*, soybean or tobacco considerably increases the drought tolerance of the transgenic plants. Moreover, it considerably increases tolerance to osmotic stress, cold and salinity stress. Hence, although the increased drought stress tolerance of the N7001 cultivar may be caused by multiple genes, the heterologous expression experiments demonstrate that single genes or alleles, such as GmeIFiso4G-1 or the GmSEO N7001 alleles, are useful to produce plants with considerable increased tolerance to drought stress, and other abiotic stress such osmotic stress, cold or salinity stress.

Thus, as an alternative to the production of transgenic plants with increased tolerance to drought stress by transforming and heterologously expressing SEQ ID NO: 1, SEQ ID NO: 2, SEQ ID NO: 8, SEQ ID NO:11 or a functionally equivalent variant thereof in other plant, the present invention also relates to a breeding method where any of the two or the two alleles are transferred by breeding. As a way of illustrative non-limitative example in this breeding method, the two N7001 alleles may be donated to the progeny by a crossing comprising at least one parental plant bearing at least one of the two N7001 alleles, wherein said parental plant may be a plant of the N7001 cultivar, a plant derived from the N7001 cultivar that bear any of the two N7001 alleles, or a transgenic plant that bears any of the two N7001 allele.

Thus, in another aspect, the invention relates to a method of producing a plant having increased abiotic stress tolerance or yield or growth relative to a corresponding control plant, the method comprising crossing a plant according to the invention, a plant obtained according to the invention or a plant identified by a method according to the invention and selecting a progeny plant having increased abiotic stress tolerance or yield or a progeny plant showing SEQ ID NO: 1, SEQ ID NO: 2, SEQ ID NO: 8, SEQ ID NO:11 or a functionally equivalent variant thereof, wherein if said plant is a soybean plant, then at least one copy of said nucleic acid sequence is found in a location in the genome different from the location where it naturally occurs or is under the control of a promoter which is not the naturally occurring promoter.

In another aspect, the invention relates to a method of selecting a plant having increased abiotic stress tolerance or yield or growth relative to a corresponding control plant, the method comprising detecting the presence of SEQ ID NO: 1, SEQ ID NO: 2, SEQ ID NO: 8, SEQ ID NO:11 or the functionally equivalent variant thereof according to the method of the invention in the progeny obtained. In particular, the transgenic plants of the invention are also meant to comprise progeny (descendant, offspring, etc.) of any generation of such a transgenic plant. A seed of any generation of all such transgenic plants wherein said seed comprises a polynucleotide sequence encoding the polypeptide of the present invention, SEQ ID NO: 5 or 7 or a functionally equivalent variant thereof, is also an important provision of the invention. In one embodiment the method of this aspect further comprises crossing the plant produced with itself, or with a different plant, for any number of subsequent generations, such that a plant with increased abiotic stress tolerance or yield is produced.

All the terms and embodiments previously described are equally applicable to this aspect of the invention.

Method of Identifying a Plant Having Increased Abiotic Stress Tolerance

In some aspect, plants of the N7001 cultivar or plants derived from the N7001 cultivar that bear any of the two N7001 alleles, will also bear the N7001 cis-regulatory region of the GmeIFiso4G-1 or the GmSEO alleles, therefore, polymorphisms not only within the genes but also within their 5' upstream and 3' downstream regions are useful for the development of molecular markers for the selection and breeding of plants bearing the GmeIFiso4G-1 and/or the GmSEO alleles, and thereby having increased tolerance to abiotic stress such as drought stress, osmotic stress and salinity stress. '5 regions include for example, regions that regulate gene expression such as the endogenous promoters of the respective GmeIFiso4G-1 or the GmSEO N7001 alleles and other respective 5' cis-regions such as enhancers.

Therefore, another aspect the invention refers to a method of identifying a plant having increased abiotic stress tolerance, the method comprising: (i) detecting a marker genetically linked to a gDNA sequence coding for SEQ ID NO: 5, SEQ ID NO: 7 or a functionally equivalent variant thereof and (ii) selecting a plant having said marker wherein if said plant is a soy bean plant, then at least one copy of said nucleic acid sequence is found in a location in the genome different from the location where it naturally occurs or is under the control of a promoter which is not the naturally occurring promoter.

The present invention discloses identification of nucleic acids sequences that can become a "molecular marker". The identification of the molecular markers permits the identification of plants with improved stress tolerance.

More than one loci contribute to different extents to complex desirable traits such as abiotic stress tolerance. Some of the involved loci may contribute to the desirable trait by functionally interacting between themselves, whereas some other involved loci may contribute to the expression of a desirable trait in a functionally independent manner not depending on the activity of other loci that also contribute to the trait. Thus, it is possible to improve complex traits in plants by introducing loci that independently contribute to the expression of a desirable trait. In some situations a single locus may be sufficient to introduce a desirable trait in a plant. The loci may be introduced in plants by transformation or breeding procedures, thereby introducing or improving a desirable trait in a plant. In order to minimize the cost and effort of fabricating a plant with a desirable trait, preferably, a single locus which causes sufficient improvement of a desirable trait will be introduced in a plant, and less preferably two loci which cause a similar sufficient improvement of the desirable trait will be introduced.

As used herein, "genomic DNA" or "gDNA" refers to chromosomal DNA present in the cell or cells of interest.

Therefore, in other aspects of the invention methods are provided to identify, select, and produce plants with increased tolerance to abiotic stress, by using molecular markers linked to a gDNA sequence coding for SEQ ID NO: 5, SEQ ID NO: 7 or a functionally equivalent variant thereof. These markers may originate from within SEQ ID NO: 1 or 2 itself or from functionally equivalent variants thereof, or from their corresponding genomic regions where they map. Given the availability of genomic sequences from numerous plants, it is possible to use bioinformatic procedures well known in the art in order to identify candidate molecular markers linked to a gDNA sequence coding for SEQ ID NO: 5, SEQ ID NO: 7 or a functionally equivalent variant thereof. Likewise, a representative genomic region SEQ ID NO: 8-13 may be sequenced and compared in order to identify polymorphisms useful to develop molecular markers for the selection of the N7001 (SEQ ID NO: 1 or 2) alleles together with the corresponding promoters and cis-regulatory elements, and for the selection of their orthologous sequences in other plant species, as well as for breeding for increased tolerance to abiotic stress. In this way, developed molecular markers can be used in breeding programs and/or in the selection of plants having the N7001 cultivar genomic region comprising the N7001 (SEQ ID NO: 8 or 11) alleles, or for the selection of orthologous genomic regions comprising orthologous gene sequences, which contribute to increased abiotic stress tolerance. Using the currently available genomic (sequence and map) resources, sequencing tools, and molecular techniques for the development of molecular markers, it would be a matter of routine for a person skilled in the art to develop markers for breeding increased tolerance to abiotic stress based on the N7001 SEQ ID NO: 1 or 2 and on their corresponding genomic regions, all what is disclosed herein. Once a gene or genomic sequence or region is found associated or contributing to a given function, a person skilled in the art would readily be able to develop corresponding molecular markers for breeding.

Depending on the extent of the N7001 5' upstream and 3' downstream regions corresponding to the GmeIFiso4G-1 or the GmSEO N7001 alleles, that is present in any soybean cultivar derived from the N7001 cultivar, different extents of local N7001-derived molecular markers are developed. If the plant donating the 5' or 3'allele is a plant of the N7001 cultivar, any desirable extent of physical linkage of the molecular markers to the genes may be used in the breeding method herein exemplified. For example, but without limiting the scope of the invention, in a particular embodiment, a desirable linkage may be given by a molecular marker located or physically mapping at 200 Kb, or at 400 Kb, or at 600 Kb, or at 800 Kb, or at 1 Mb, or at 1.2 Mb, or at 2 Mb, or at 3 Mb of sequence 5' upstream to the GmeIFiso4G-1 and/or the GmSEO N7001 alleles. Similarly, without limiting the scope of the invention, examples of a desirable linkage with the GmeIFiso4G-1 or the GmSEO N7001 alleles may be given by a molecular marker located or physically mapping at 200 Kb, or at 400 Kb, or at 600 Kb, or at 800 Kb, or at 1 Mb, or at 1.2 Mb of sequence 3' downstream to the GmeIFiso4G-1 and/or the GmSEO N7001 alleles. In order to practice the breeding methods exemplified herein, a person skilled in the art can choose any extent of 5' or 3' linkage or genetic distance from the molecular marker to the GmeIFiso4G-1 and/or the GmSEO N7001 alleles, including a 5' or 3' genetic distance of 0.5 Centimorgan (cM), or of 0.8 cM, or of 1 cM, or of 2 cM, or of 3 cM. Depending on the magnitude of the 5' or 3' physical or genetic linkage of the molecular marker to the GmeIFiso4G-1 and/or the GmSEO N7001 alleles, depends the number of progeny plants to which the GmeIFiso4G-1 and/or the GmSEO N7001 alleles and cis-regulatory regions is donated. One or more 5' and/or 3' molecular markers are used in the breeding method herein exemplified. In general, the tighter the linkage of the one or more molecular markers to the GmeIFiso4G-1 and/or the GmSEO N7001 alleles, the larger the number of progeny plants that are selected using said molecular markers to which the GmeIFiso4G-1 and/or the GmSEO N7001 alleles and cis-regulatory regions are transferred and with it increased tolerance to abiotic stress. The tighter the linkage the less likely the occurrence of recombination between the molecular marker and the GmeIFiso4G-1 and/or the GmSEO N7001 alleles and cis-regulatory regions.

"Genetically linked" as used herein relates to the tendency of a DNA that are close together on a chromosome to be inherited together during the meiosis phase of sexual reproduction. Two genetic markers that are physically near to each other are unlikely to be separated onto different chromatids during chromosomal crossover, and are therefore said to be more linked than markers that are far apart.

In a preferred embodiment, the genetic marker is located 5' upstream the nucleic acid sequence coding for SEQ ID NO: 5, 7 or a functionally equivalent variant thereof.

Analysis of promoter regions (2000 bp. upstream of translation initiation codon), of GmSEOs genomic sequences from Williams 82, TJ2049 and N7001 cultivars, allowed the identification of one dinucleotide microsatellite in TJ2049 or Williams 82 $(AT)_{13}$ and $(AT)_9$ in N7001. This microsatellite was found to be located 26 bp upstream from a drought responsive element MBS, for binding of MYB transcription factors using PlantCARE database (a database of plant cis-acting regulatory elements and a portal to tools for in silico analysis of promoter sequences. Lescot, M., Déhais, P., Moreau, Y., De Moor, B., Rouzé, P., and Rombauts, S. Nucleic Acids Res., Database issue (2002), 30:325-327). This site is homologous to a site present in the promoter region of RD29B drought regulated gene from *Arabidopsis thaliana*.

Therefore, in a particular embodiment, the marker genetically linked to a gDNA sequence coding for SEQ ID NO: 5, SEQ ID NO: 7 is a dinucleotide microsatellite located 26 bp upstream from the drought responsive element MBS (MS2 binding site).

"Microsatellite", as used herein, relates to a tract of repetitive DNA in which certain DNA motifs (ranging in length from 2-13) are repeated, typically 5-50 times.

In a more particularly embodiment, the molecular marker is the sequence shown in SEQ ID NO: 14 or the sequence shown in SEQ ID NO: 15.

In a preferred embodiment, the molecular marker is s SNP. As used herein, the term "single nucleotide polymorphism (SNP)" refers to a DNA sequence variation occurring when a single nucleotide—A, T, C, or G—in the genome (or other shared sequence) differs between members of a species (or between paired chromosomes in an individual).

In a particular embodiment the abiotic stress is selected from the group consisting of osmotic, salinity, drought or cold stress.

In the breeding method herein exemplified molecular markers are also developed from the genic regions of the GmeIFiso4G-1 or the GmSEO N7001 alleles. One or more markers developed from the gene exons or introns may be used. Markers developed within the genes may be used along with markers developed from the 5' or 3' regions linked to the GmeIFiso4G-1 or the GmSEO N7001 alleles.

Many plant species have shown different extents of local microsynteny at given orthologous genomic regions or loci. Therefore, the invention also comprises detecting a marker genetically linked to a functionally equivalent variant of a sequence coding for SEQ ID NO: 5 or 7.

The terms "ortholog" and "orthologous" refer to a nucleic acid sequence or gene which functions similarly to a nucleic acid sequence or gene from another species. For example, where one gene from one plant species has a high nucleic acid sequence similarity and codes for a protein with a similar function to another gene from another plant species, such genes would be "orthologs". Orthologs are also defined as genes that have diverged after a speciation event, thus implying that products of orthologous genes should tend to keep their original functions.

Furthermore, microsynteny including genes, intergenic regions, and (associated) molecular markers, makes it possible the positional cloning or map-based cloning of genes, using interspecies comparative genomics for the development of inter-species molecular markers and isolation of desirable genes. Inter-species molecular markers are those that are conserved across species and therefore are useful for the selection of plants of different species based on their status for the interspecies-molecular marker. Inter-species molecular markers need not be identical in sequence, but they are developed directly or indirectly from the GmeIFiso4G-1 or the GmSEO N7001 alleles and/or from their respective 5'upstream or 3'downstream regions.

Inter-species molecular markers are used for the selection of plants of different species that have increased tolerance to abiotic stress. The selected plants may thereafter be used in breeding programs aiming at the development of other plants or cultivars of that species with increased tolerance to abiotic stress.

Once a genomic region or locus is associated with a given trait, it is a matter of routine in the art to use the large number of technological developments and procedures currently available, to identify polymorphisms between allelic and/or orthologous genomic regions and to develop from the polymorphisms, molecular markers useful for selecting desirable allelic or orthologous regions transferred by breeding from a donor parent to the progeny.

In the method herein exemplified, molecular markers linked to the GmeIFiso4G-1 or the GmSEO N7001 alleles themselves and/or linked to their respective 5'upstream or 3'downstream regions, are developed by for example, comparing the N7001 genomic region comprising the corresponding alleles and/or their respective 5'upstream or 3'downstream regions, with the corresponding genomic regions of the parental plant or cultivar to which progeny increased tolerance to abiotic stress is to be transferred by crossing with a plant bearing the N7001 alleles. From the molecular differences observed molecular markers will be developed in order to trace in the progeny the transfer of the alleles. Non-limiting examples of useful polymorphisms or marker genetically linked to the sequences of interest are single nucleotide polymorphisms (SNP: Single Nucleotide Polymorphisms), multiple nucleotide polymorphisms, restriction site-polymorphisms, sequence deletions polymorphisms, sequence insertion polymorphisms, and repeated sequence polymorphisms. Non-limiting examples of useful molecular markers are those developed using single nucleotide polymorphisms (SNP: Single Nucleotide Polymorphisms), multiple nucleotide polymorphisms, restriction site-polymorphisms, sequence deletions polymorphisms, sequence insertion polymorphisms, and repeated sequence polymorphisms. A person skilled in the art would readily apply available technologies and procedures to develop the molecular markers used in the methods taught in this example.

Once one or more molecular markers are developed they will be used to detect and select for inheritance of the GmeIFiso4G-1 or the GmSEO N7001 alleles and/or of their respective N7001 5' upstream and 3' downstream genomic regions, in progeny plants obtained by crossing a parental plant bearing the GmeIFiso4G-1 or the GmSEO N7001 alleles and/or their respective N7001 5' upstream and 3' downstream genomic regions, with another parental plant or cultivar to which progeny the GmeIFiso4G-1 or the GmSEO N7001 alleles and/or of their respective N7001 5' upstream and 3' downstream genomic regions is to be transferred in order breed progeny plants with increased tolerance to abiotic stress. Likewise, orthologous molecular markers developed in other species are used to select progeny plants inheriting the genomic region that is orthologous to the N7001 GmeIFiso4G-1 or the GmSEO alleles and/or to the respective N7001 5' upstream and 3' downstream genomic regions.

Using the SoyKB web resourse resource available information was collected. The non-limiting examples of different types of polymorphisms within the soybean GmeIFiso4G-1 gene and within approximately 1 Mb of the corresponding 5' upstream and 3'downstream genomic regions, which may be useful as molecular markers for breeding, are characterized.

In Glyma17g08030 sequence, which comprises the 5' UTR, gene exons and introns, and the 3' UTR, 19 SNP were identified by GWAS located in positions 5935726, 5936025, 5936026, 5936042, 5936247, 5936849, 5936900, 5936902, 5936909, 5936910, 5937128, 5938323, 5938662, 5938684, 5938699, 5938701, 5938800, 5939123, 5941000. Moreover, 6 SNPs named GSSNP1892412 GSSNP1892413, GSSNP1892414, GSSNP1892415, GSSNP1892416, GSSNP1892417 located in positions 5936247, 5936849, 5938036, 5938684, 5938800, 5938800, respectively are described in SoyKB Web resource based on Liam et al. 2010 (Nature Genet. 42: 1053-1059) and Kim et al. 2010 (Proc. Natl. Acad. Sci USA. 107: 22032-22037). This resource uses the Gene Model V 9.0 Assembly V1.1.

Therefore, in a preferred embodiment, the marker genetically linked to a gDNA sequence coding for SEQ ID NO: 5 or a functionally equivalent variant thereof is a SNP located in any of the following positions: 5935726, 5936025, 5936026, 5936042, 5936247, 5936849, 5936900, 5936902, 5936909, 5936910, 5937128, 5938323, 5938662, 5938684, 5938699, 5938701, 5938800, 5939123, 5941000, 5938036 and 5938684.

In another preferred embodiment, the marker genetically linked to a gDNA sequence coding for SEQ ID NO: 5 or a functionally equivalent variant thereof is a SNP in the 5' upstream region of the Glyma17g08030 gene. Non-limiting examples of SNPs are in the nucleotide position in chromosome 11: 4935173, 5142386, 5361658, 5608884, 5834948, with a distance in number of nucleotides to the gene start of: 999849, 793536, 574264, 327038, 100974 respectively were identified by Lam et al 2010. (Nature Genet. 42:1053-1059) using genome-wide association study (GWAS), and which may also be used to develop molecular markers linked to the N7001 GmeIFiso4G-1 allele, sequence coding for SEQ ID NO: 5, for breeding plants with increased tolerance to abiotic stress. The GmeIFiso4G-1 gene physical location in soybean chromosome 11 comprises position 5934982 to position 5941515.

Other non-limiting exemplary SNPs map at the gene 3' downstream region. The SNPs chosen to be presented as described are positioned at thousands to at up to hundreds of thousands nucleotides distance from each other and/or from the beginning and end of the gene, respectively as applicable. Any other SNP already described in these regions, or resulting from new routine polymorphisms screens in the region, may be used as well to readily develop molecular markers for breeding plants with increased tolerance to abiotic stress.

In another preferred embodiment, the marker genetically linked to a gDNA sequence coding for SEQ ID NO: 5, SEQ ID NO: 7 or a functionally equivalent variant thereof is a SNP selected from the group consisting of: 4935173, 5142386, 5361658, 5608884 and 5834948.

In another preferred embodiment, the marker genetically linked to a gDNA sequence coding for SEQ ID NO: 5 or a functionally equivalent variant thereof is a SNP selected from the group consisting of: 5941775, 6152301, 6422738, 6696343 and 6941469 with a distance in number of nucleotides to the gene end of: 260, 210786, 481223, 754828, 999954 respectively.

In addition, the breeding methods provided in this example may be carried out using molecular markers developed from polymorphisms corresponding to sequence deletions or insertions in the 5' upstream or 3' downstream region of the GmeIFiso4G-1 gene. A large number of sequence deletion-based or sequence insertion-based polymorphisms have been described in these 5' upstream or 3' downstream regions, any of which may be used to develop molecular markers for breeding plants with increased tolerance to abiotic stress. Table 1 presents a non-limiting summary of the total number of deletion polymorphisms, insertion polymorphisms, and SNPs polymorphisms located in the 5' upstream or 3' downstream region of the GmeIFiso4G-1 gene. The total number of SNPs shown in Table 1 comprises SNPs described by Lam et al. by comparing wild soybeans and soybean cultivars, or described by Wu et al. 2010. *BMC Genomics.* 2010, 11: 469 by comparing the Williams and Forrest soybean cultivars.

In another preferred embodiment, the marker genetically linked to a gDNA sequence coding for SEQ ID NO: 5 or a functionally equivalent variant thereof is a SNP selected from Table 1.

TABLE 1

Type of polymorphism and their corresponding total number in the 5' upstream or 3' downstream region of the GmeIFiso4G-1 gene.

| Type of polymorphism | Total number within 1 Mbp of gene upstream region | Total number within 1 Mbp of gene downstream region |
|---|---|---|
| Insertions | 220 | 157 |
| Deletions | 179 | 83 |
| SNPs described by Lam et al. | 7293 | 7501 |
| SNPs described by Wu et al. | 43 | 26 |

Additionally, using the SoyKB internet resource available information was also collected in order to present herein non-limiting examples of different types of polymorphisms within the soybean GmSEO gene and within approximately 1 Mb of the corresponding 5' upstream and 3'downstream genomic regions, which may be useful as molecular markers for breeding. In Glyma20g34670 sequence, which comprises the 5' UTR, gene exons and introns, and the 3' UTR, amongst the 25 SNPs described using GWAS the following SNPs are included: 43025464, 43025642, 43025653, 43025713, 43025726, 43025753, 43025838, 43025896, 43025908, 43025938, 43026099, 43026364, 43026778, 43026779, 43026780, 43027046, 43027188, 43028099, 43029037, 43029038, 43029040, 43029041, 43029049, 43029050, 43029051.

Therefore, in another preferred embodiment, the marker genetically linked to a gDNA sequence coding for SEQ ID NO: 7 or a functionally equivalent variant thereof is a SNP located in any of the positions: 43025464, 43025642, 43025653, 43025713, 43025726, 43025753, 43025838, 43025896, 43025908, 43025938, 43026099, 43026364, 43026778, 43026779, 43026780, 43027046, 43027188, 43028099, 43029037, 43029038, 43029040, 43029041, 43029049, 43029050, 43029051.

Moreover, a soy bean SNP named GSSNP2496413 in position 43026364 was identified. These SNPs are described in SoyKB Web resource based on Lim et al. 2010 and Kim et al. 2010. This resource use the Gene Model V 9.0 Assembly V1.1. Moreover, in Table 2 and Table 3, non-limiting examples of SNPs in the 5' upstream and 3' downstream regions of the GmSEO gene are presented, which were identified by Lam et al. 2010 (*Nature Genet.* 42:1053-1059) and/or by Kim et al., 2010 (*Proc. Natl. Acad. Sci USA.* 107: 22032-22037) and which may also be used to develop molecular markers linked to the N7001 GmSEO allele for breeding plants with increased tolerance to abiotic stress. For the sake of brevity, Table 2 shows only 8 non-limiting exemplary SNPs mapping at the gene 5' upstream region two of which were described both by Lam et al. 2010 and by Kim et al. 2010, whereas Table 3 shows only ten non-limiting exemplary SNPs mapping at the gene 3' downstream region five of which were described by Lam et al. 2010 and 5 of which were described by Kim et al. 2010. The SNPs chosen to be presented as examples in tables 2 and 3, are positioned at thousands to at up to hundreds of thousands nucleotides distance from each other and/or from the beginning and end of the gene, respectively as applicable. Any other SNP already described in these regions, or resulting from new routine polymorphisms screens in the region, may be used as well to readily develop molecular markers for breeding plants with increased tolerance to abiotic stress. In another preferred embodiment, the marker genetically linked to a gDNA sequence coding for SEQ ID NO: 7 or a functionally equivalent variant thereof is a SNP selected from Table 2.

TABLE 2

SNPs described by Lam et al. and/or by Kim et al. in the upstream region of the GmSEO gene. The nucleotide position of the corresponding SNP in chromosome 20 is presented, as well as the relative distance in number of nucleotides to the start of the gene. The GmSEO gene physical location in soybean chromosome 20 comprises position 43024564 to position 43029592. Two SNPs that were described both by Lam et al. and by Kim et al. are indicated in bolds.

| SNPs described by Lam et al. | | SNPs described by Kim et al. | | |
| --- | --- | --- | --- | --- |
| Distance in number of nucleotides to the gene start | Nucleotide position in chromosome 20 | Distance in number of nucleotides to the gene start | Nucleotide position in chromosome 20 | SNP ID |
| 999929 | 42024650 | 999929 | 42024650 | GSSNP2493857 |
| 749963 | 42274616 | 749909 | 42274670 | GSSNP2494512 |
| 500725 | 42523854 | 500725 | 42523854 | GSSNP2495123 |
| 249873 | 42774706 | 249947 | 42774632 | GSSNP2495806 |
| 1206 | 43023373 | 1572 | 43023007 | GSSNP2496412 |

In another preferred embodiment, the marker genetically linked to a gDNA sequence coding for SEQ ID NO: 7 or a functionally equivalent variant thereof is a SNP selected from Table 3.

TABLE 3

SNPs described by Lam et al. (2010) and/or by Kim et al. (2010), in the downstream region of the GmSEO gene. The nucleotide position of the corresponding SNP in chromosome 20 is presented, as well as the relative distance in number of nucleotides to the end of the gene. The GmSEO gene physical location in soybean chromosome 20 comprises position 43024564 to position 43029592. In this table none of the SNPs presented were described both by Lam et al. (2010) and by Kim et al (2010).

| SNPs described by Lam et al. | | SNPs described by Kim et al. | | |
| --- | --- | --- | --- | --- |
| Distance in number of nucleotides to the gene end | Nucleotide position in chromosome 20 | Distance in number of nucleotides to the gene end | Nucleotide position in chromosome 20 | SNP ID |
| 5056 | 43029635 | 5648 | 43030227 | GSSNP2496414 |
| 213811 | 43238390 | 327976 | 43352555 | GSSNP2497087 |
| 477389 | 43501968 | 586066 | 43610645 | GSSNP2497762 |
| 690522 | 43715101 | 798603 | 43823182 | GSSNP2498438 |
| 1004940 | 44029519 | 1004930 | 44029509 | GSSNP2499111 |

Molecular markers developed from polymorphisms corresponding to sequence deletions or insertions in the 5' upstream or 3' downstream region of the GmSEO gene, may be used in the breeding methods provided in this example. A large number of sequence deletion-based or sequence insertion-based polymorphisms have been described in these 5' upstream or 3' downstream regions, any of which may be used to develop molecular markers for breeding plants with increased tolerance to abiotic stress. Table 4 presents a non-limiting summary of the total number of deletion polymorphisms, insertion polymorphisms, and SNPs polymorphisms located in the 5' upstream or 3' downstream region of the GmSEO gene. The total number of SNPs shown in Table 4 comprises SNPs described by Lam et al. (2010) by comparing wild soybeans and soybean cultivars, or described by Wu et al. (2010) by comparing the Williams and Forrest soybean cultivars. In another preferred embodiment, the marker genetically linked to a gDNA sequence coding for SEQ ID NO: 7 or a functionally equivalent variant thereof is a SNP selected from Table 4.

TABLE 4

Type of polymorphism and their corresponding total number in the 5' upstream or 3' downstream region of the GmSEO gene.

| Type of polymorphism | Total number within 1 Mbp of gene upstream region | Total number within 1 Mbp of gene downstream region |
| --- | --- | --- |
| Insertions | 146 | 353 |
| Deletions | 144 | 269 |
| SNPs described by Lam et al. | 10100 | 9183 |
| SNPs described by Wu et al. | 2697 | 2556 |

In this way, already described SNPs, insertion polymorphisms, and deletion polymorphisms, as well as other sequence-based polymorphisms not described in this disclosure but that would be routinely identified by a person skilled in the art, located either within in the GmeIFiso4G-1 gene or within the GmSEO gene, and/or located in their respective 5' upstream and/or 3' downstream flanking genomic regions, may be assessed for association with the corresponding N7001 gene allele and their corresponding flanking regions, for the development of molecular markers useful in the breeding methods provided in this example aiming at producing plants with increased tolerance to abiotic stress. Available routine procedures in the art may be used in order to screen and identify allele-specific polymorphisms for use in the development of molecular markers for plant breeding.

In the methods of breeding provided in this example, plants with increased tolerance to abiotic stress are produced by introducing by crossing the N7001 cultivar-derived cis-regulatory region, such as the promoter, along with the corresponding controlled allele of the GmeIFiso4G-1 gene and/or of the GmSEO gene. Molecular markers developed which are linked to the genomic region comprising the N7001 alleles of the GmeIFiso4G-1 gene and/or of the GmSEO gene, are used to screen and select progeny plants with increased tolerance to abiotic stress. In one embodiment of the methods provided in this example, plants with increased tolerance to abiotic stress are produced by introducing by crossing the N7001 cultivar-derived cis-regulatory region comprising at least the promoter along with the corresponding controlled allele of the GmeIFiso4G-1 gene. In another embodiment of the methods provided in this example, plants with increased tolerance to abiotic stress are produced by introducing by crossing the N7001 cultivar-derived cis-regulatory region comprising at least the promoter along with the corresponding controlled allele of the GmSEO gene. In yet another embodiment of methods provided in this example, plants with increased tolerance to abiotic stress are produced by both introducing by crossing the N7001 cultivar-derived cis-regulatory region comprising at least the promoter along with the corresponding controlled alleles of the GmeIFiso4G-1 gene and also introducing by crossing the N7001 cultivar-derived cis-regulatory region comprising at least the promoter along with the corresponding controlled alleles of the GmSEO gene.

All the terms and embodiments previously described are equally applicable to this aspect of the invention.

The invention will be described by way of the following examples which are to be considered as merely illustrative and not limitative of the scope of the invention.

EXAMPLES

Example 1: Identification and Isolation of Soybean Genes Functionally Associated with Increased Tolerance to Drought Stress 1.1 Soybean Genotypes The soybean genotypes used in this example were the N7001 genotype that is characterized by increased tolerance to drought stress, and the TJ2049 genotype that is characterized by susceptibility to drought stress.

1.2 Soybean Plant Growth Conditions and Drought Stress Regime

Soybean plants were grown in a growth chamber with a 16/8 hour (light/night) photoperiod, temperatures of 30° C. and 20° C. for day and night respectively, and an irradiancy regime of 800 µmol m$^{-2}$ s$^{-1}$ using metallic halogen lamps (150 W) and sodium incandescent lamp (75 W). The growth chamber was also supplemented with an input of natural sunlight to cover the high lighting demand of soybean.

Plant growth recipients or pots consisted of PVC cylinders of 11 cm diameter and 30 cm high, having the bottom covered with a metal mesh. Tubes were filled with a mix sand/vermiculite (ratio 1/1) as substrate. Initially, three soybean plants were grown per pot, but once plantlets were established only one plant was chosen and left in each pot to continue growing. Plants were watered daily to field capacity, with Rigaud and Puppo (1975) (Physiologia Plantarum 35 (1975) 181-185) medium supplemented with 10 mM of KNO3 through a holed tube. In order to attain maximum water retention capacity of the substrate, pots were watered up until excess of water drained from the bottom of the pots through the metal mesh. The pots were kept in this condition for 24 hours, time when no water excess drainage was observed. In this way the maximum volume of water held by the substrate was quantified and the resulting value was used as reference to express the percentage of water retained by the soil substrate during drought stress. Up until the drought stress treatment was carried out, plants were watered at maximum soil water retention capacity.

Soybean plants were grown during 35 days, the time when they reached the V4 developmental stage. During this period plants were grown in soil irrigated at maximum soil water retention capacity. Experimental replicas of six pots per genotype and per treatment were used, and the replicas were randomly distributed in the growth chamber in order to rule out possible variations due to small differences in environmental conditions that may have occurred in different locations within the growth chamber.

Plants were subjected to drought stress after 35 days of growth when they reached the V4 stage. At that moment plant drought stress was conducted by terminating irrigation at maximum soil water retention capacity and by thereafter continuing irrigation at about 50% of the maximum soil water retention capacity. Non-stressed control plants at the V4 stage continued to be daily irrigated at maximum soil water retention capacity as they were before reaching the V4 stage.

1.3 Generation and Characterization of a Subtracted cDNA Library Enriched in Drought-Induced Genes.

A library was constructed that is enriched in drought-induced sequences of the drought-tolerant cultivar N7001. The library was screened using forward and subtractive probes generated from cDNA from the drought-tolerant N7001 cultivar and from the drought-sensitive TJ2049 cultivar. For this, plants were grown under non-drought stress conditions or under drought stress conditions. The expression of the genes represented in the cDNA library was compared between these two genotypes. In this way SEQ ID NO: 1 and 2 were isolated, which are not expressed under non-drought stress conditions but are expressed or upregulated under drought stress conditions in the soybean N7001 cultivar. Furthermore, the N7001 and the TJ2049 soybean cultivars, which differ in their tolerance or sensitivity to drought, show differential expression of SEQ ID NO: 1 and 2 upon drought stress. The soybean N7001 cultivar (described in Hufstetler E V, Boerma R H, Carter T E y Earl H J (2007). Crop Sci. 47, 25-35.), is considered drought tolerant due to its slow wilting phenotype (see Sloane, R., Patterson, R., Carter, T. (1990). *Field drought tolerance of a soybean plant introduction.* Crop Science. 30, 118-123. Crop Sci. 30, 118-123; Hudak C M and Patterson R P (1995) Crop Sci. 35, 464-471). Moreover, it was found that soybean N7001 cultivar exhibits significantly higher levels of gene induction in response to drought stress when compared with the drought sensitive soybean TJ2049 cultivar. In addition, it is disclosed herein that the heterologous expression of soybean SEQ ID NO: 1 or the heterologous expression of SEQ ID NO: 2 in *Arabidopsis* transgenic plants, results in a considerable increased tolerance to drought stress, salt stress, osmotic stress. Surprisingly, the protein encoded by SEQ ID NO: 2 that belongs to the SEO family, has not been found present in forisomes of soybean, and it is the only member of soybean SEO family whose expression is not restricted to the phloem (Rüping B. et al. (2010) *Molecular and phylogenetic characterization of the sieve element occlusion gene family in Fabaceae and non-Fabaceae plants*. BMC Plant Biol. 10: 21910.1186/1471-2229-10-219).

Specifically, the suppression subtractive hybridization procedure was employed to construct a library enriched in drought-induced genes from the soybean genotype N7001. For this, total RNA was extracted from leaf samples of drought stressed plants and of non-stressed control plants, at time points corresponding to 3 and 7 days after the onset of drought stress. Fifty µg of total RNA extracted from plants sampled at each time point were pooled together, thereby generating a single total RNA sample corresponding to drought-stressed plants, and single total RNA sample corresponding to non-stressed control plants. mRNA was then purified form the total RNA samples, and 2 µg of mRNA were used to synthesize cDNA for the suppression subtractive hybridization procedure. The Clontech PCR Select-cDNA Subtraction Kit (BD Biosciences Clontech) was employed for the suppressive subtractive hybridization procedure, using the samples derived from drought-stressed plants as tester and the samples derived from non-stressed control plants as driver. The resulting secondary PCR products were purified, then inserted into the pCR II vector, and then transformed into *Escherichia coli* TOP 10 competent cells, using the TA cloning kit Dual Promoter from Life Technologies. After this, approximately 800 clones were selected to sequence their vector inserts of soybean origin.

1.4 Reverse Northern Blots

Reverse Northern blot analysis of differentially expressed sequences present in the subtracted cDNA library were carried out using the PCR-Select™ Differential Screening Kit (BD Biosciences Clontech). Insert-derived PCR-amplified fragments of the library clones were dot-blotted onto Nylon membranes and probed with $32^P$-labeled subtracted probes. The probes used derived from RNA samples obtained at time points corresponding to 3 and 7 days after the onset of drought stress; and derived from RNA samples obtained from the drought-tolerant N7001 soybean variety, from the drought-susceptible TJ2049 soybean variety, and from non-stressed controls. DNA samples corresponding to individual bacterial clones, were arrayed in groups of 96, and blotted 8 times for hybridization to each subtracted probe. After hybridization, clones were selected for further studies when they showed differential hybridization with the probe derived from RNA samples obtained from the drought-tolerant N7001 soybean variety, with the probe derived from the drought-susceptible TJ2049 soybean variety, and with the probe derived from non-stressed controls.

1.5 Northern Blots

Vector soybean cDNA-inserts of clones selected after reverse northern were used as probes to confirm the differential expression of the corresponding soybean genes by Northern blot (FIGS. 1A and 1B). For this, total RNA was isolated from drought-stressed plants (DH) and from non-stressed control plants (Ctrl) of the soybean N7001 and TJ2049 cultivars. Plants were exposed to water deficit and sampling was performed when soil water potential ψ approximately −0.75 MPa was reached. Ten µg of total RNA, isolated using standard procedures based on phenol/chloroform extraction followed by LiCl precipitation, were separated in denaturing formaldehyde agarose gels. Ethidium bromide staining of the gels demonstrated that equal amounts of RNA were loaded in the gels. The electrophoresed RNA was transferred to nylon membranes (Hybond XL, Amersham Pharmacia Biotech). Membranes were prehybridized at 65° C. in 5×SSPE, 5×Denhardt's solution, 0.2% SDS and 0.5 mg mL-1 denatured salmon sperm DNA. Hybridizations were performed at 65° C. overnight. Hybridization was carried out using probes prepared from full-length cDNAs of GmeIFiso4G (SEQ ID NO: 1) and GmSEO (SEQ ID NO: 2), respectively. Probes were labeled with $[\alpha^{32P}]$-dCTP using the Rediprime II random priming labeling system (Amersham Pharmacia Biotech). After hybridization filters were washed twice for 30 min at 65° C. with 5×SSC-0.5% SDS, and twice using the same conditions with 1×SSC-0.5% SDS, and exposed in autoradiography films.

Figure 2:
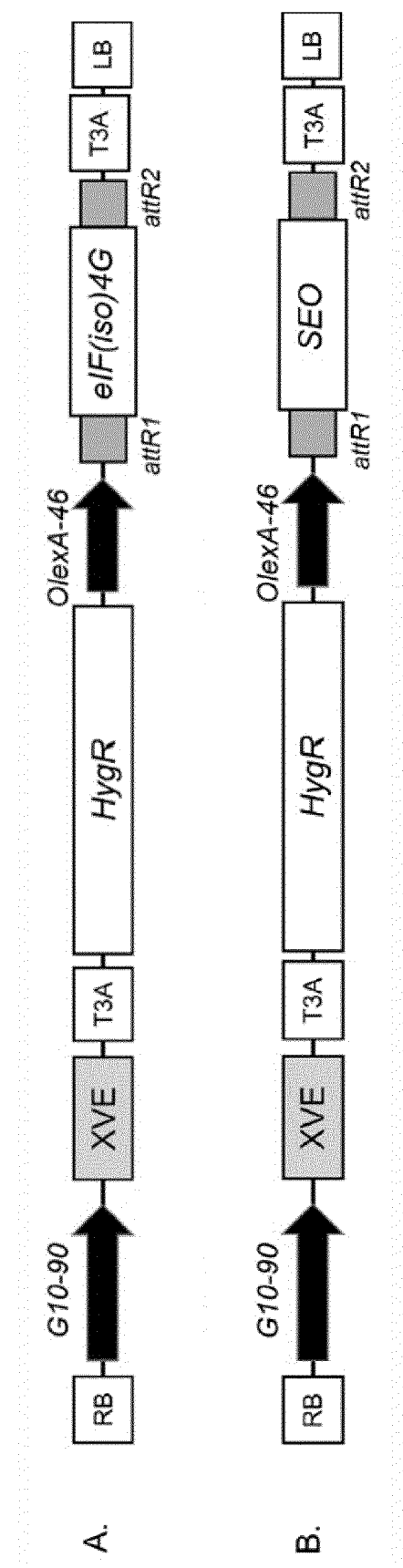
FIG. 2. Schematic representation of the constructs used for Arabidopsis transformation. RB: T-DNA right border; G10-90: synthetic promoter (Ishige F, Takaishi M, Foster R, Chua N H y Oeda K (1999) *A G-box motif (GC-CACGTGCC) tetramer confers high levels of constitutive expression in dicot and monocot.* Plant J 18: 443-448) controlling XVE; DNA sequences encoding a chimeric transcription factor containing the DNA-binding domain of LexA (residues 1-87), the transcription activation domain of VP16 (residues 403-479) and the regulatory region of the human estrogen receptor (residues 282-595); T3A: rbcS E9 poly(A) addition sequence; HygR: hygromycin resistance cassette; OlexA-46: eight copies of the LexA operator sequence and the −46 35S minimal promoter (SEQ ID NO:18); attR1 and attR2 (LR clonase recombination sites) LB: left border of the T-DNA. (A) eIFiso4G: coding cDNA region of translation initiation factor iso 4G; (B) SEO: coding region of GmSEO.

1.6 Preparation of Constructs for Controlled Heterologous Expression of SEQ ID NO: 1 or 2 in Transgenic Plants Full length cDNA of SEQ ID NO: 1 (GmeIFiso4G) or SEQ ID NO: 2 (GmSEO), were PCR-amplified from total RNA samples extracted from drought-stressed soybean N7001 plants. The resulting amplified full-length cDNAs were individually cloned into the pENTR2B entry vector (Gateway, Invitrogen), and the two resulting recombinant entry vectors were thereafter used for LR-mediated recombinational insertion of the respective cDNAs into pMDC7 destination binary vector (Curtis, M., Grossniklaus, U. (2003). *Plant Physiol.* 133(2):462-9). Using this vector, transgene expression is regulated by a chimeric β-o-estradiol inducible promoter. The two resulting pMDC7-based vectors, one comprising the full length cDNA SEQ ID NO: 1, and the other one comprising the full length cDNA SEQ ID NO: 2, were individually introduced in *Agrobacterium tumefaciens* strain C58C1 by electroporation. FIG. 2 shows an illustration of the pMDC7 vector cassette comprising the N7001 soybean variety full length cDNA sequences of GmeIFiso4G or GmSEO.

Figure 3:
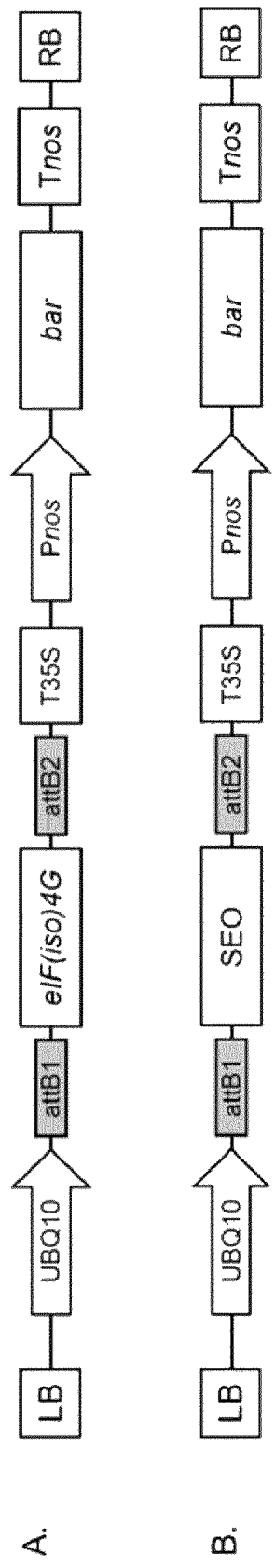
FIG. 3. Schematic representation of the constructs used for tobacco transformation. LB: T-DNA left border; UBQ10: 634 base pairs of the promoter ($P_{UBQ10}$) immediately upstream of the ubiquitin-10 gene from Arabidopsis (At4g05320); T35S: 35S terminator; bar: phosphinothricin-N-acetyltransferase that confers resistance to the herbicide Basta embedded in 5'- and 3'-regulatory elements of the nopaline synthase; RB: right border of the T-DNA. (A) GmeIFiso4G: coding cDNA region of translation initiation factor iso 4G; (B) GmSEO: coding region of GmSEO.

FIG. 3 shows a schematic representation of the constructs used for tobacco transformation.

1.7 Production of Transgenic Plants Heterologously Expressing Soybean SEQ ID NO: 1 or 2

1.7.1 Production of *Arabidopsis* Transgenic Plants Heterologously Expressing Soybean SEQ ID NO: 1 or 2

The pMDC7-based constructs were introduced into *Arabidopsis thaliana* (glauca) by using an *Agrobacterium*-mediated floral dip transformation method described in Clough SJ1, Bent A F. (1998). Plant J. 16(6):735-43). T1 seeds of infiltrated plants were collected and selected by germination on agar-solidified half strength MS medium containing 25 mg L-1 hygromicin. Subsequently, 25 hygromicin resistant seedlings were transferred into soil to produce seeds. Thereafter, crossing and selection of transgenic plants was continued until homozygous transgenic lines were produced from kanamycin resistant T3 seedlings that were used for further analysis. Ten individual kanamycin resistant lines harboring each corresponding construct were selected for detailed molecular analysis. The expression of the transgenes was tested in the 10 independent lines selected by RT-PCR and Northern blot analysis, in the presence and absence of 5 µM β-estradiol.

1.7.2 Production of Tobacco Transgenic Plants Heterologously Expressing Soybean SEQ ID NO: 1 or 2

The construct for constitutive overexpression of GmeIF (iso)4G-1 or GmSEO in tobacco plants, were made by inserting the cDNA coding region of each of these genes into pUbi-dest vector, via GATEWAY cloning system (Grefen C, et al. 2010. *Plant Journal:* 64, 355-365). The resulting constructs were introduced into *Agrobacterium tumefaciens*, strain C58C1 (Deblaere et al., 1985, *Nucleic Acids Res.*, 13:4777-4788).

*Nicotiana tabacum* L, cultivar Samsung were used for Agrobacterium mediated transformation according to Gallois and Marinho (1995, *Methods Mol Biol.* 49:39-48). Homozygous transgenic lines were produced from phosphinotricin resistant T2 seedlings and used for further analysis.

1.7.3 Production of Soybean Transgenic Plants Over-Expressing Soybean SEQ ID NO: 2.

Figure 14:
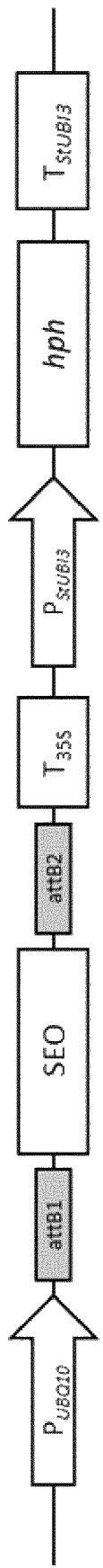
FIG. 14. Vector for soybean transformation. Schematic representation of the construct used for soybean transformation. UBQ10: 634 base pairs of the promoter ($P_{UBQ10}$) immediately upstream of the ubiquitin-10 gene from *Arabidopsis* (At4g05320); SEO: coding cDNA region of GmSEO from N7001 cultivar); T35S: 35S terminator; 930 base pairs of the promoter of UBI3 gene from *Solanum tuberosum* ($P_{StUBI3}$); hph: Hygromycin-B 4-O-kinase that confers resistance to hygromycin, and 402 base pairs of the 3' regulatory region of the UBI3 gene from *Solanum tuberosum* ($T_{StUBI3}$).

The construct for constitutive overexpression of GmSEO in soybean plants, was made by inserting the cDNA coding region of the gene into pUbi-dest vector, via GATEWAY cloning system (Grefen C, et al. 2010. *Plant Journal:* 64, 355-365). The resulting expression cassette was PCR amplified and cloned into pUHN-4 vector (Joshi et al. 2005. *In Vitro Cell. Dev. Biol. Plant* 41, 437-445). This vector contains the hygromycin resistance gene (hph) driven by the potato ubiquitin (UBI3) promoter (Garbarino and Belknap, 1994. *Plant Mol. Biol.* 24:119-127) and the termination sequence of the same gene. *Glycine max* (soybean), cultivar Jack (Nickell, C. D. et al. 1990. Crop Sci. 30:1365) was used for transformation using particle bombardment. Biolistic transformation of somatic embryos was performed as described by Hancock et al 2011. Plant Physiol. 157:552-562). Transgenic plants were selected by PCR amplification of the inserted construct and expression of the transgene, and phenotyped in the T3 generation (FIG. 14).

1.8 Assessment of Abiotic Stress Tolerance of Transgenic Plants

*Arabidopsis* T3 transgenic plants that were homozygote for the transformed full-length cDNAs of the GmeIFiso4G gene SEQ ID NO: 1 or for the transformed full-length cDNA of the GmSEO gene SEQ ID NO: 2, were used to assess whether the heterologous expression of the respective soybean genes transformed was able to confer or increase abiotic stress tolerance relative to control plants. For abiotic stress tolerance assessment, plants were subjected to osmotic stress, salt stress, drought stress.

Figure 4:
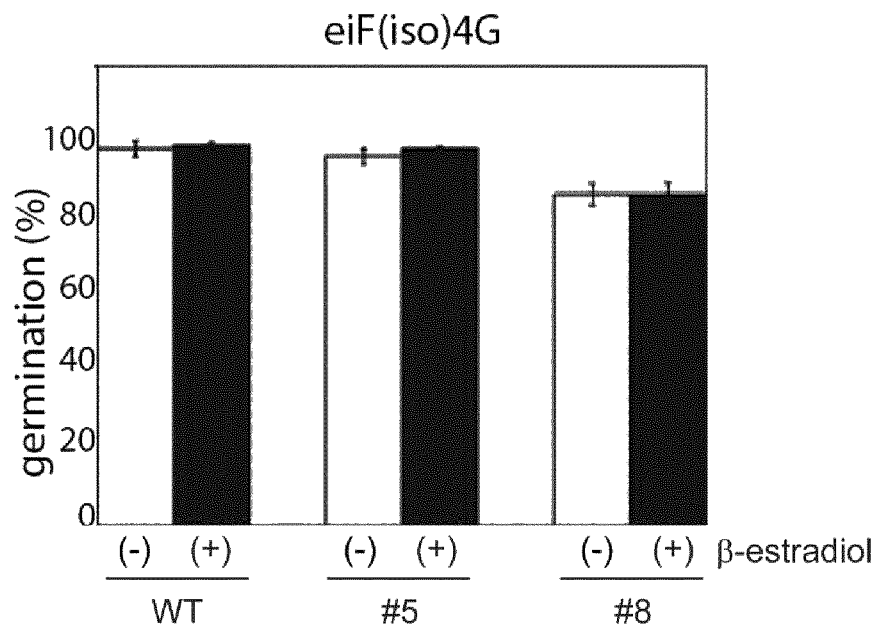
FIG. 4. The effect of transgene overexpression over normal growth and germination assessed by comparing dry weight of seedlings and germination rates from transgenic and wild type Arabidposis, in the presence or absence of 2 μM β-o estradiol.
Figure 4:
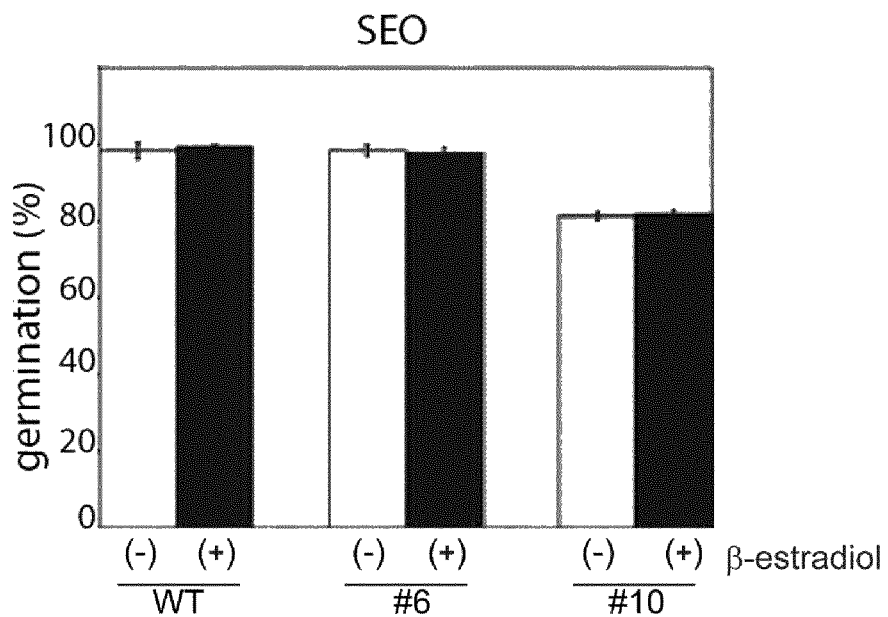

The effect of transgene overexpression over normal growth and germination was assessed by comparing dry weight of seedlings and germination rates from transgenic and wild type plants, in the presence or absence of 2 µM β-o estradiol. The results showed that transgene expression did not alter growth or germination rates, as shown in FIG. 4.

1.8.1 Assessment of Transgenic Plants Tolerance to Osmotic Stress, Salt Stress, Drought Stress and Cold Stress Evaluation of tolerance to osmotic stress, salinity stress, and drought stress was carried out in plates containing jellified agar-MS media. Seeds from *Arabidopsis thaliana glauca* and transgenic lines were surface sterilized for 15 min in 7% of bleach with 0.05% Tween-20. Washes with sterilized water were performed 5 times and seeds were thereafter incubated at 4° C. for 3 days and plated in petri dishes with half strength MS medium (2.4 g L-1 Murashige & Skoog, 0.5 g L-1 Monohydrate 2-ethanesulfonic acid and 10% agar). Plants were grown at 22° C. with a photoperiod of 16 hours light and a photon flux of 120 µmol m$^{-2}$ sec$^{-1}$. For phenotypic analysis, 5 days old seedlings were transferred to half MS medium supplemented with NaCl (150 mM), mannitol (300 mM) or PEG-infused agar plates (PEG 8000, 40%). Previous to exposure to stress inducing conditions, the transgene was induced by spraying transgenic plants with 2 µM β-estradiol and incubation for additional 16 hrs in the same plates. Plant growth was monitored by taking images after 7 to 9 days of stress. Rosette and root growth were determined by measuring the dry weight (DW) of each plant. In salt stress experiments the total chlorophyll content, was also determined.

Experimental controls comprising non-transgenic plants for osmotic stress and salt stress tolerance evaluation included: wild type *Arabidopsis glauca* (WT) plants grown under non-stress conditions (Ctrl), WT plants grown under abiotic stress conditions, WT plants treated with β-estradiol (est) and grown under non-stress conditions, and WT plants treated with β-estradiol (est) and grown under abiotic stress conditions.

Experimental controls comprising transgenic plants for osmotic stress and salinity stress tolerance evaluation included: transgenic plants grown under non-stress conditions, transgenic plants treated with β-estradiol (est) and grown under non-stress conditions, and transgenic plants grown under abiotic stress conditions. The experimental set up for the actual assessment of transgenic plants tolerance to osmotic stress and salinity stress included: transgenic plants treated with β-estradiol (est) and grown under abiotic stress conditions.

The following paragraphs describe the results obtained in the experiments carried out to evaluate the transgenic plants tolerance to osmotic stress and salinity stress.

1.8.1.1 Tolerance to Osmotic Stress

Figure 5A:
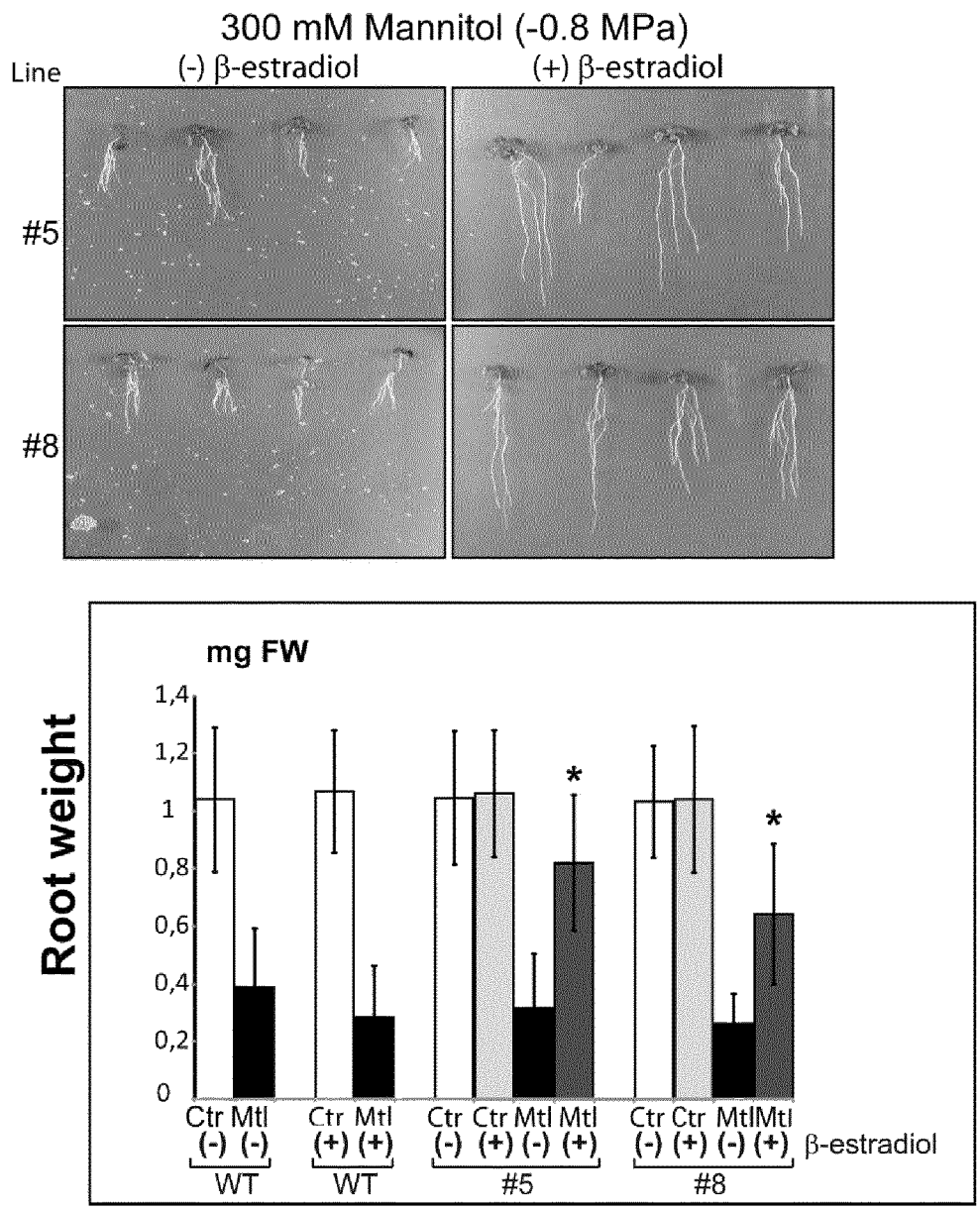
FIG. 5. Effect of the heterologous expression of eIFiso4G in Arabidopsis in exposure to osmotic stress. 5 days old seedlings were sprayed with 2 μM β-estradiol [(+) β-estradiol] for 16 hours or with dH$_2$O [(−) β-estradiol], and thereafter transferred to mannitol containing plates, (A), or PEG containing plates (B). Pictures were taken after 9 days of stress. Dry weight measurements of roots were performed and average and standard deviation is shown (n=12).
Figure 5B:
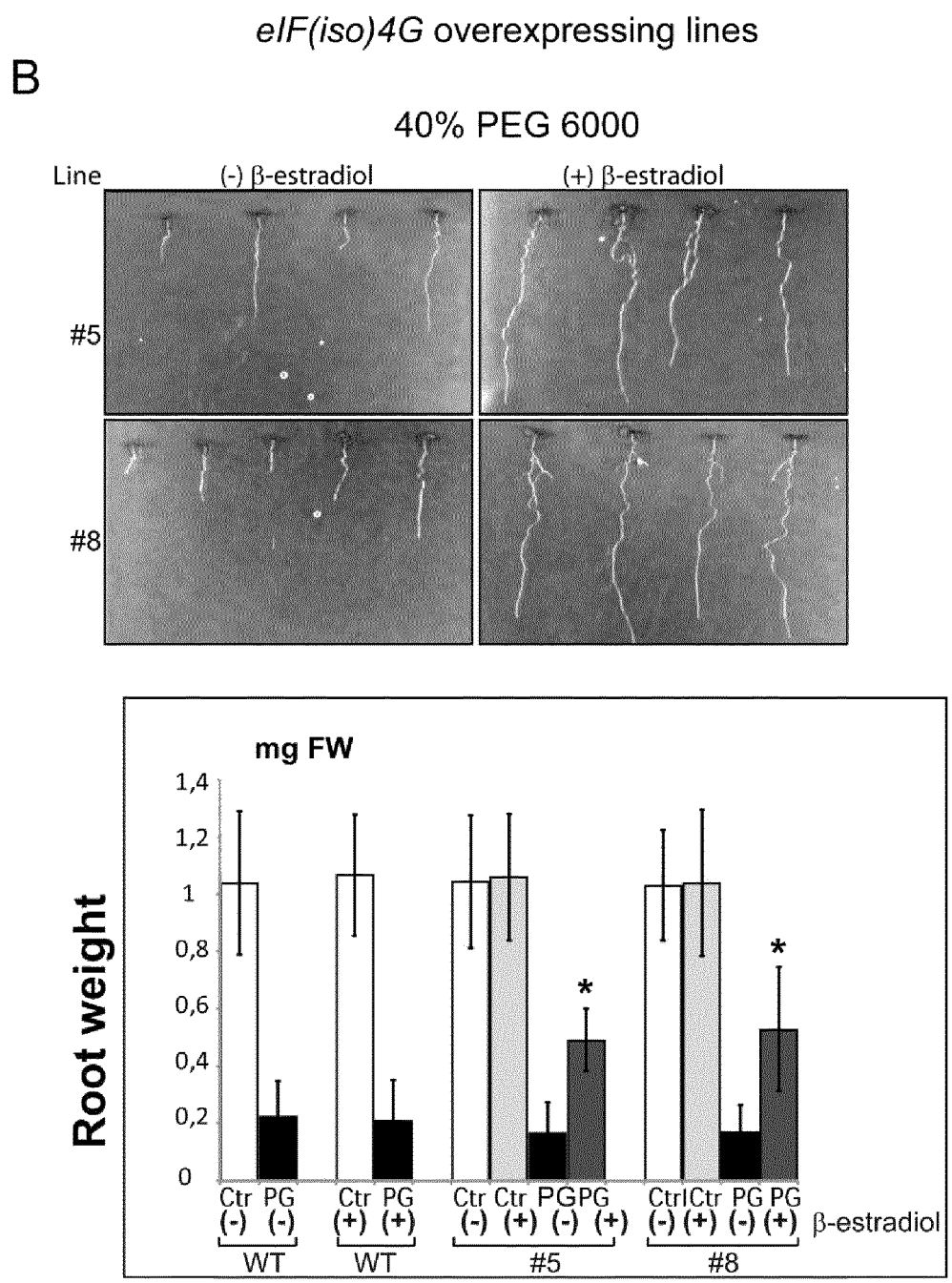

FIG. 5 demonstrates that *Arabidopsis* transgenic plants expressing the full-length cDNA of the GmeIFiso4G gene (SEQ ID NO: 1) have considerably increased tolerance to the osmotic stress caused by their incubation in mannitol-supplemented plates (A) or in PEG-supplemented plates (B), in contrast with plants not expressing the transgene and incubated in the same stress conditions. FIGS. 5A and 5B clearly show a high increase in tolerance to osmotic stress of plants where the transgene was induced by β-estradiol. This is reflected by the considerable increase in root development and general plant health of plants expressing the transgene under stress conditions, in contrast with transgenic plants under the same stress conditions but where the transgene was not induced by treatment with β-estradiol. In addition, the bars plots in FIGS. 5A and 5B show that when the transgene is not induced, the dry weight of roots of transgenic plants subjected to mannitol-induced stress or to PEG-induced stress, is comparable to that of wild type plants subjected to the same stress; whereas when the transgene is induced and plants are subjected to mannitol-induced stress or to PEG-induced stress, the dry weight of roots increases considerably. Furthermore, in some individual transgenic plants treated with β-estradiol and subjected to mannitol-induced stress or to PEG-induced stress, it was observed that the dry weight of roots was equal to that of non-stressed plants. Considering all these results, it can be concluded that expression of the N7001 GmeIFiso4G gene is useful to produce plants with increased tolerance to osmotic stress.

Figure 6:
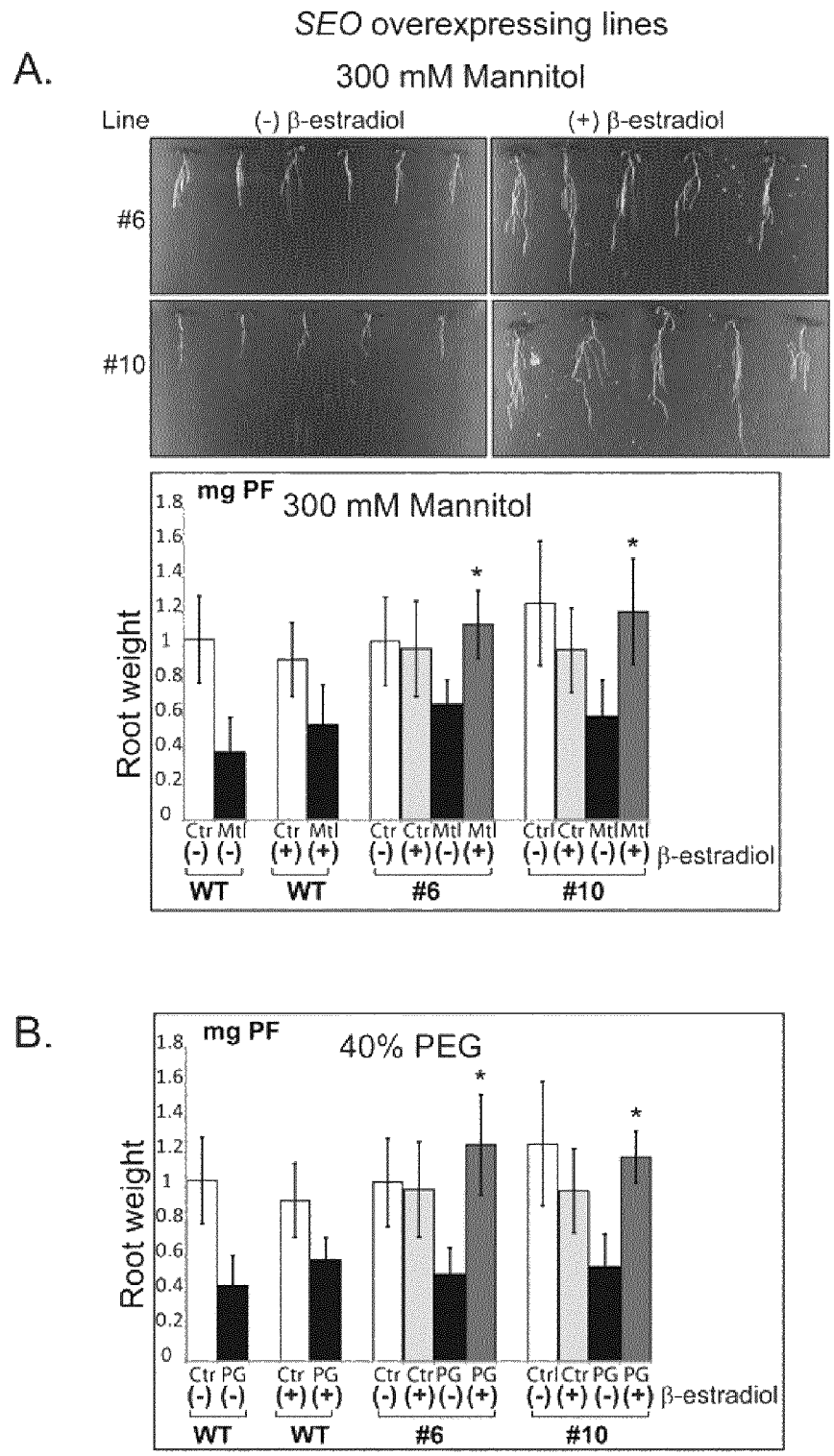
FIG. 6. Effect of the heterologous expression of GmSEO in Arabidopsis in exposure to osmotic stress. 5 days old seedlings were sprayed with 2 μM β-estradiol for 16 hours and thereafter transferred to mannitol containing plates (A), or PEG containing plates (B). Pictures were taken after 9 days of stress Dry weight measurements of roots were performed and average and standard deviation is shown (n=12).

FIG. 6 demonstrates that *Arabidopsis* transgenic plants expressing the full-length cDNA of the GmSEO gene (SEQ ID NO: 2) have considerably increased tolerance to the osmotic stress caused by their incubation in mannitol-supplemented plates or in PEG-supplemented plates (B), in contrast with plants not expressing the transgene and incubated in the same stress conditions. FIGS. 6A and 6B evidence a high increase in tolerance to osmotic stress of plants where the transgene was induced by β-estradiol. This is reflected by the considerable increase in root development and general plant health of plants expressing the transgene grown under stress conditions, in contrast with transgenic plants under the same stress conditions but where the transgene was not induced by treatment with β-estradiol. In addition, the bars plots in FIGS. 6A and 6B show that when the transgene is not induced, the dry weight of roots of transgenic plants subjected to mannitol-induced stress or to PEG-induced stress, is comparable to that of wild type plants subjected to the same stress; whereas when the transgene is induced and plants are subjected to mannitol-induced stress or to PEG-induced stress, the dry weight of roots increases considerably and is even higher than that of non-stresses transgenic and non-transgenic plants. Therefore, it can be concluded that expression of the N7001 GmSEO gene is useful to produce plants with increased tolerance to osmotic stress. In addition, it can also be concluded that expression of the N7001 GmSEO gene is useful to produce plants with increased root growth under osmotic stress conditions, in addition to its usefulness to produce plants with increased tolerance to osmotic stress.

Figure 7:
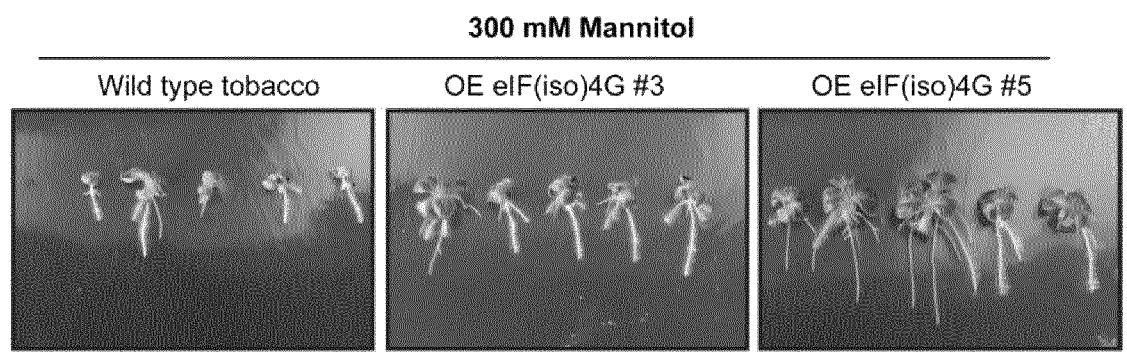
FIG. 7. Effect of the heterologous expression of eIFiso4G in tobacco in exposure to osmotic stress. A) Seeds from wild type and transgenic overexpressing (OE) tobacco lines were germinated in MS 0.5% sucrose, supplemented with Mannitol to a final concentration of 300 mM. Pictures were taken 6 days after germination. B) Northern blot showing expression levels of GmeIF(iso)4G in transgenic tobacco lines.
Figure 7:

FIG. 7 demonstrates that tobacco transgenic plants expressing the full-length cDNA of the GmeIFiso4G-1 gene (SEQ ID NO: 1) have considerably increased tolerance to the osmotic stress caused by their incubation in mannitol-supplemented plates, in contrast with plants not expressing the transgene and incubated in the same stress conditions.

Figure 8:
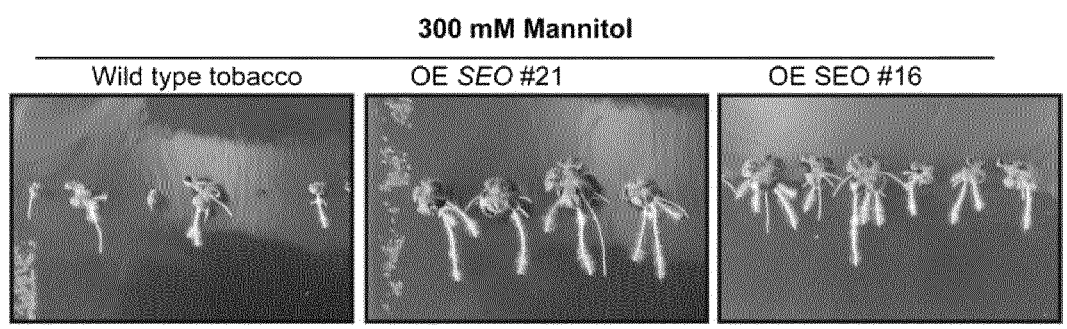
FIG. 8. Effect of the heterologous expression of GmSEO in tobacco in exposure to osmotic stress. A) Seeds from wild type and transgenic overexpressing (OE) tobacco lines were germinated in MS 0.5% sucrose, supplemented with Mannitol to a final concentration of 300 mM. Pictures were taken 6 days after germination. B) Northern blot showing expression levels of GmSEOs in transgenic tobacco lines.
Figure 8:
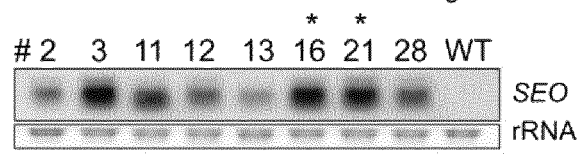

FIG. 8 demonstrates that tobacco transgenic plants expressing the full-length cDNA of the GmSEO gene (SEQ ID NO: 2) have considerably increased tolerance to the osmotic stress caused by their incubation in mannitol-supplemented plates, in contrast with plants not expressing the transgene and incubated in the same stress conditions.

1.8.1.2 Tolerance to Salt Stress

Figure 9:
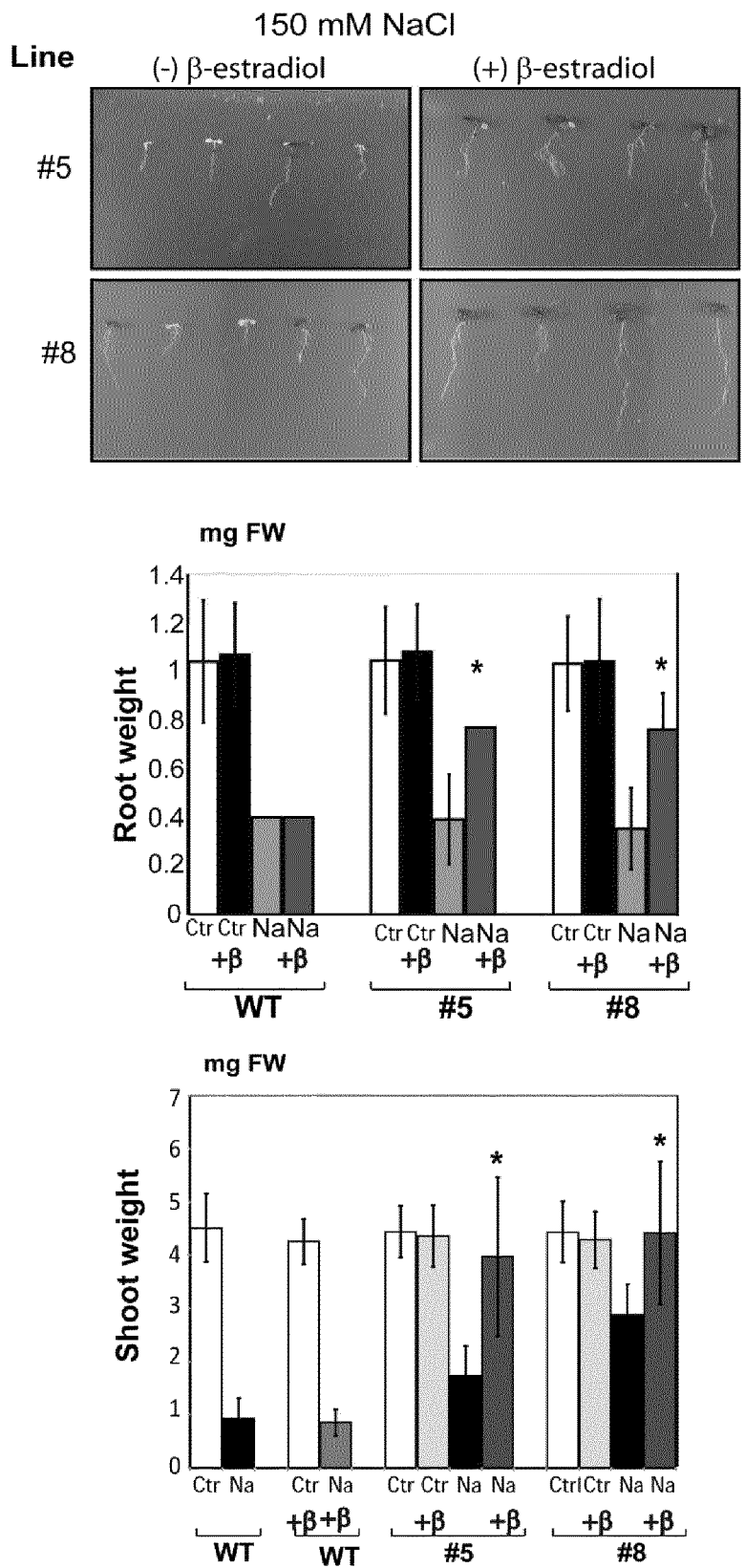
FIG. 9. Effect of the heterologous expression of eIFiso4G in Arabidopsis in exposure to salt stress. 6 days old seedlings were sprayed with 2 μM β-estradiol for 16 hours and thereafter transferred to NaCl containing plates. Pictures were taken after 7 days of stress. Dry weight measurements of shoots or roots were performed and average and standard deviation is shown (n=12).

FIG. 9 demonstrates that *Arabidopsis* transgenic plants expressing the full-length cDNA of the GmeIFiso4G-1 gene (SEQ ID NO: 1) have considerably increased tolerance to salinity caused by their incubation in NaCl-supplemented plates, in contrast with plants not expressing the transgene and incubated in the same stress conditions. There is a clear high increase in tolerance to salinity in plants where the transgene was induced by β-estradiol. This is also reflected by the considerable increase in shoot and root development and in overall health of plants expressing the transgene under stress conditions, in contrast with transgenic plants under the same stress conditions but where the transgene was not induced by treatment with β-estradiol. In addition, the bars plots in FIG. 9 shows that when the transgene was not induced, the dry weight of roots and shoots of transgenic plants subjected to salt stress, is comparable to that of wild type plants subjected to the same stress (except for shoots of transgenic plants of line #8); whereas when the transgene was induced and plants were subjected to salt stress, the dry weight of shoots and roots increased considerably. Furthermore, in some individual transgenic plants treated with β-estradiol and subjected to salinity, it was observed that the dry weight of roots and shoots was equal to, or even higher than, that of non-stressed transgenic and non-transgenic plants. Therefore, it can be concluded that expression of the N7001 GmeIFiso4G-1 gene is useful to produce plants with increased tolerance to salt stress. In addition, it can also be concluded that expression of the N7001 GmeIFiso4G-1 gene is useful to produce plants with increased shoot and root growth under salt stress conditions, in addition to its usefulness to produce plants with increased tolerance to salinity.

Figure 10:
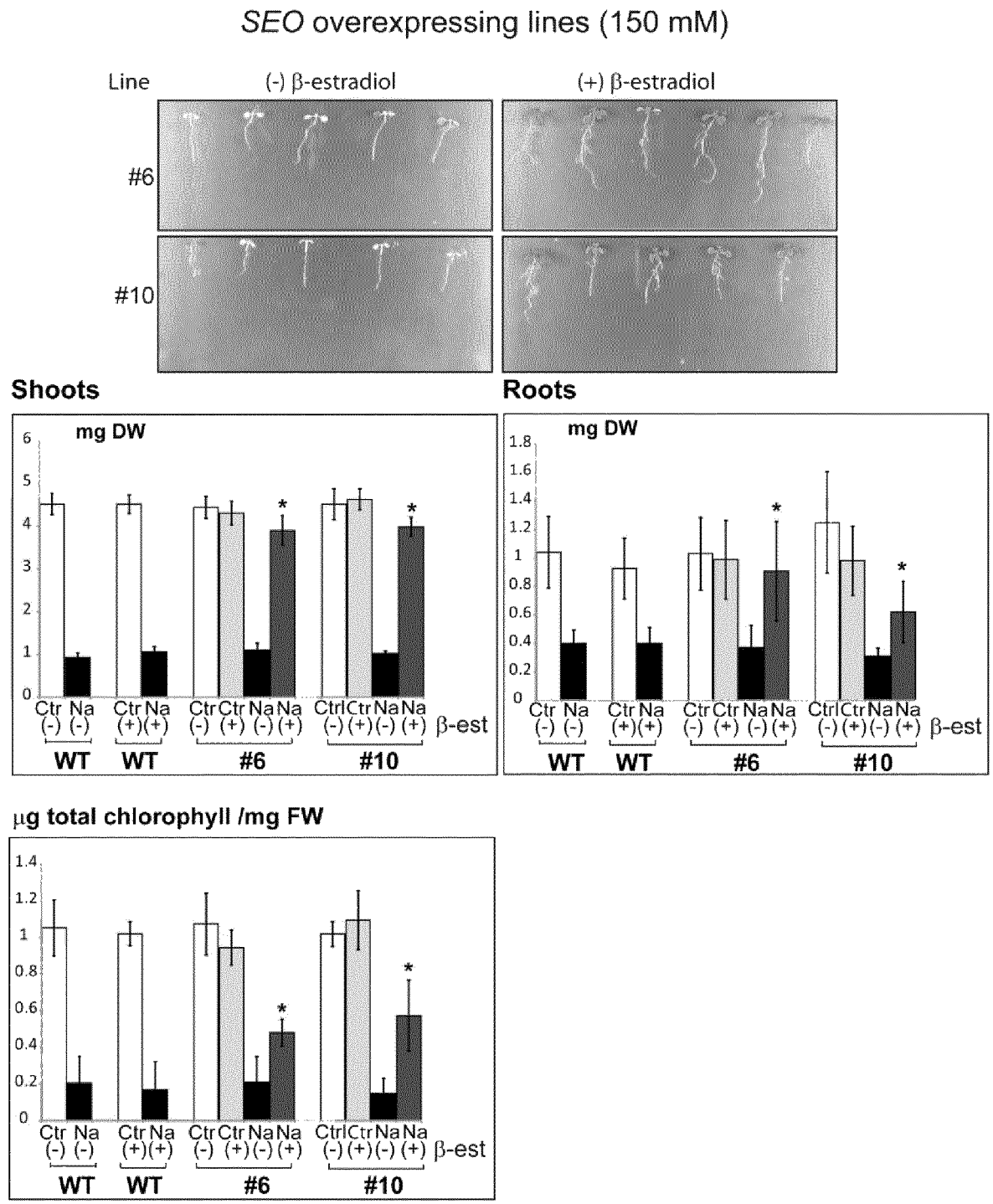
FIG. 10. Effect of the heterologous expression of GmSEO in Arabidopsis in exposure to salt stress. 6 days old seedlings were sprayed with 2 μM β-estradiol for 16 hours and thereafter transferred to NaCl containing plates. Pictures were taken after 7 days of stress. Dry weight measurements of roots or shoots were performed and average and standard deviation is shown (n=12). Total chlorophyll (μg/mg fresh weight) was extracted and quantified from each individual plant, and the figure shows the average and standard deviation of 12 plants.

FIG. 10 demonstrates that *Arabidopsis* transgenic plants expressing the full-length cDNA of the GmSEO gene (SEQ ID NO: 2) have considerably increased tolerance to the salinity stress caused by their incubation in NaCl-supplemented plates, in contrast with plants not expressing the transgene and incubated in the same stress conditions. There is a remarkable increase in tolerance to salinity stress in plants where the transgene was induced by β-estradiol. This is also evidenced by the considerable increase in shoot and root development and in overall health of plants expressing the transgene under stress conditions, in contrast with transgenic plants under the same stress conditions but where the transgene was not induced by treatment with β-estradiol, or in contrast with non-transgenic plants grown under the same stress conditions. In addition, the bars plots in FIG. 10 show that when the transgene is not induced, the dry weight of roots and shoots of transgenic plants subjected to salinity stress, is comparable to that of wild type plants subjected to the same stress; whereas when the transgene is induced and plants are subjected to salinity stress, the dry weight of shoots and roots increases considerably. Therefore, it can be concluded that expression of the N7001 GmSEO gene is useful to produce plants with increased tolerance to salinity stress. FIG. 10 also shows that chlorophyll content considerable increases upon induction of the transgene. Thus, the expression of the N7001 GmSEO gene is useful to produce plants with increased chlorophyll content under salinity stress growth conditions.

1.8.2 Assessment of Transgenic Plants Tolerance to Drought Stress

For assessment of transgenic plants tolerance to drought stress, two weeks old plants grown in pots with soil were subjected to drought by withholding water irrigation during 5 days. For transgene induction plants were treated with 200 µl of 5 µM β-estradiol. Experimental controls included transgenic plants treated with 200 µl of water. At the end of the 5 days drought stress period, pictures were taken and dry weight was measured.

Figure 11:
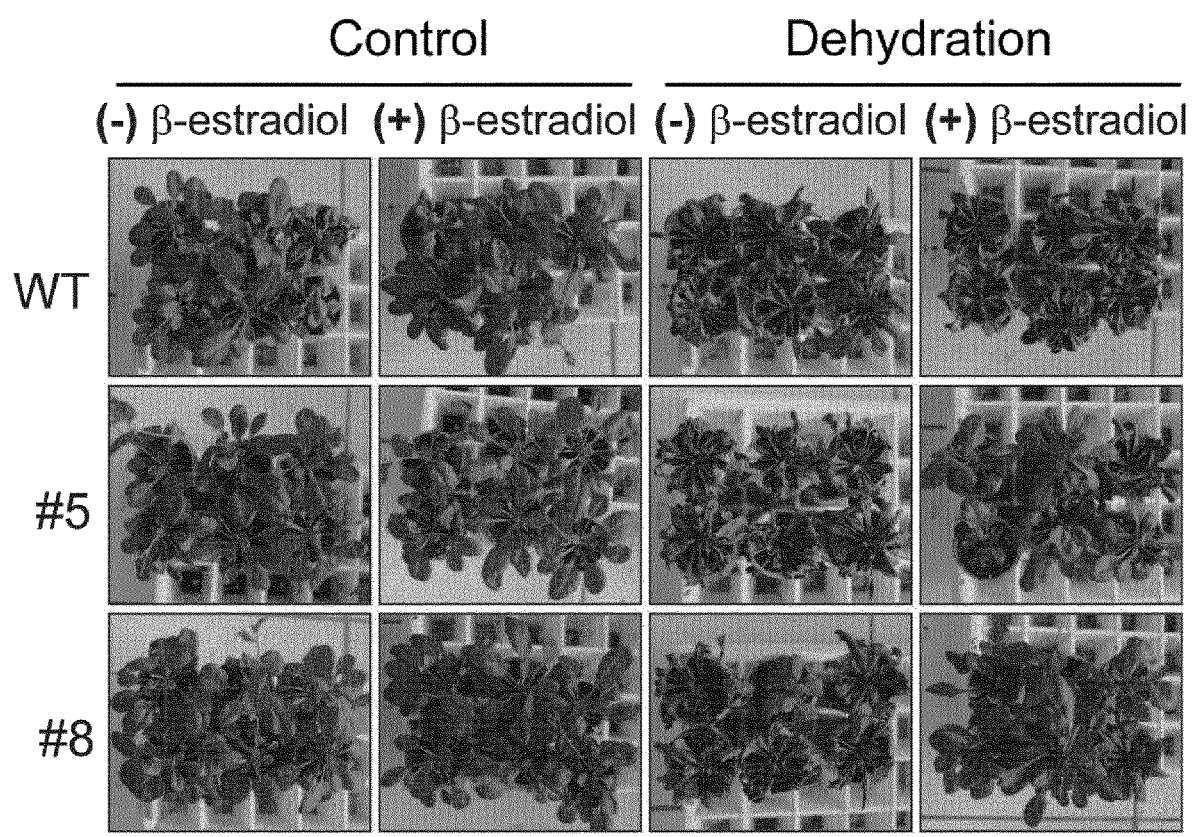
FIG. 11. Effect of the heterologous expression of eIFiso4G in Arabidopsis in exposure to drought stress. Two weeks old plants were subjected to drought treatment by water withholding. One half of the plants were treated with 200 μl of 5 μM β-estradiol, and controls were treated with the same volume of water. Pictures were taken after 5 days of water withholding.

FIG. 11 demonstrates that *Arabidopsis* transgenic plants expressing the full-length cDNA of the GmeIFiso4G gene SEQ ID NO: 1 have considerably increased tolerance to drought stress, in contrast with transgenic plants not expressing the transgene and incubated in the same conditions. Therefore, it can be concluded that the expression of the N7001 GmeIFiso4G-1 gene is useful to produce plants with increased tolerance to drought stress.

Figure 12:
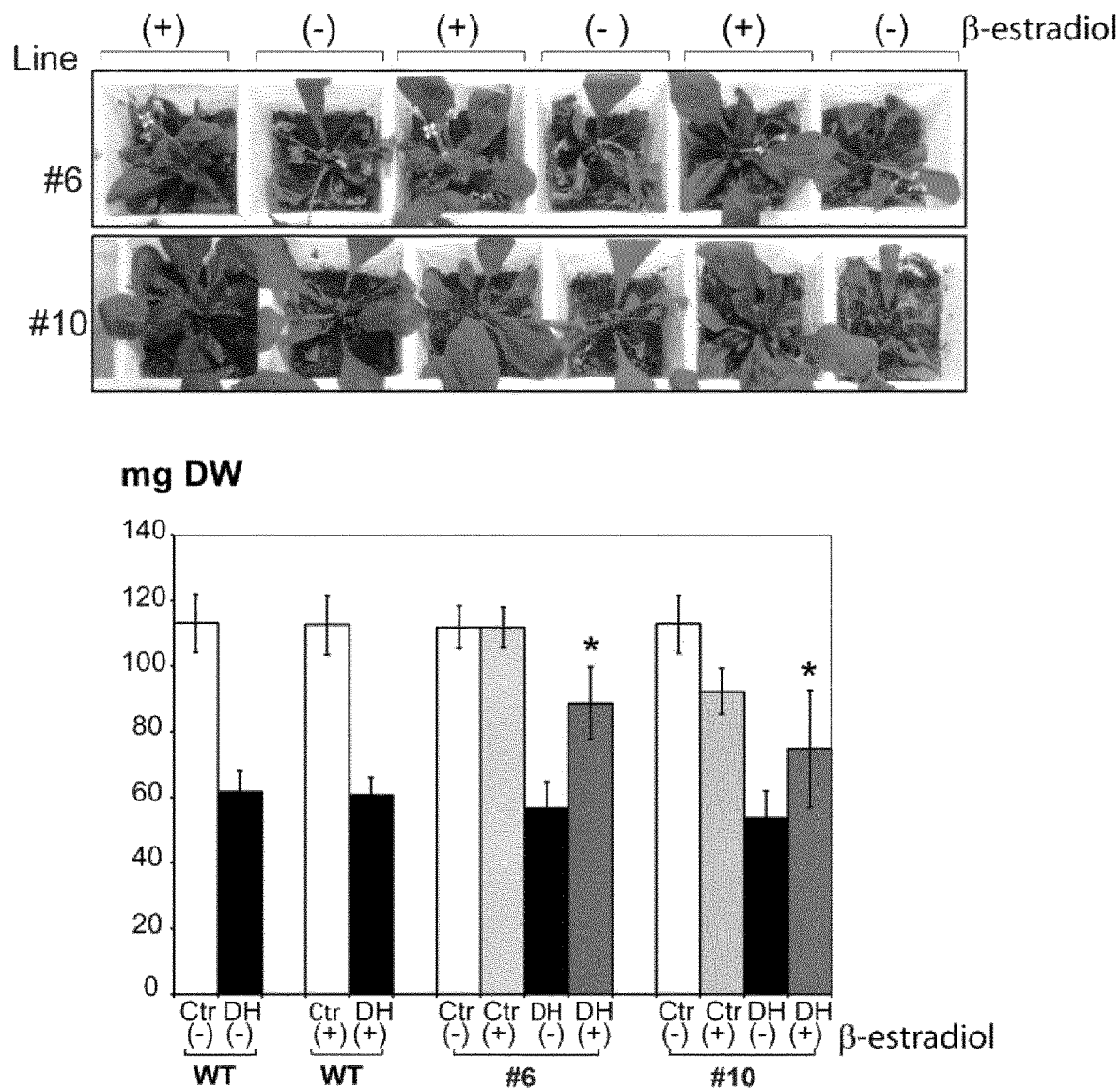
FIG. 12. Effect of the heterologous expression of GmSEO in Arabidopsis in exposure to drought stress. Two weeks old plants were subjected to drought treatment by water withholding. One half of the plants were treated with 200 μl of 5 μM β-estradiol, and controls were treated with the same volume of water. Pictures were taken after 5 days of water withholding, and dry weight (DW) of each plant was determined. Results are shown as an average or 12 plants. Error bars represent the standard deviation.

FIG. 12 demonstrates that *Arabidopsis* transgenic plants expressing the full-length cDNA of the GmSEO gene SEQ ID NO: 2 have considerably increased tolerance to drought stress, in contrast with transgenic plants not expressing the transgene and incubated in the same stress conditions. Therefore, it can be concluded that expression of the N7001 GmSEO gene is useful to produce plants with increased tolerance to drought stress.

1.8.3 Assessment of Transgenic Plants Tolerance to Cold Stress

Cold treatment was performed to 10-day-old wild type and transgenic lines, grown together on pots with a diameter of 15 cm and then exposing the plants to 4° C. Plants were exposed to low temperature for a period of two weeks, with a 16-h-light/8-h-dark light regime and 120 µmol photons m-2 s-1. Three biological replicates were done, each of them containing 10 plants per treatment.

For anthocyanin determination, 4 plants per sample were powdered using liquid N2 and stored at −80° C. until processing. Anthocyanin was extracted was determined according to Neff and Chory (1998, Plant Physiol., 118:27-35) from supernatants of centrifuged samples, using 400 µL of methanol:H20:HCl (60:40:1). The relative amount of anthocyanin was determined using the formula: (A530-A657).1000. mg FW-1.

Figure 13:
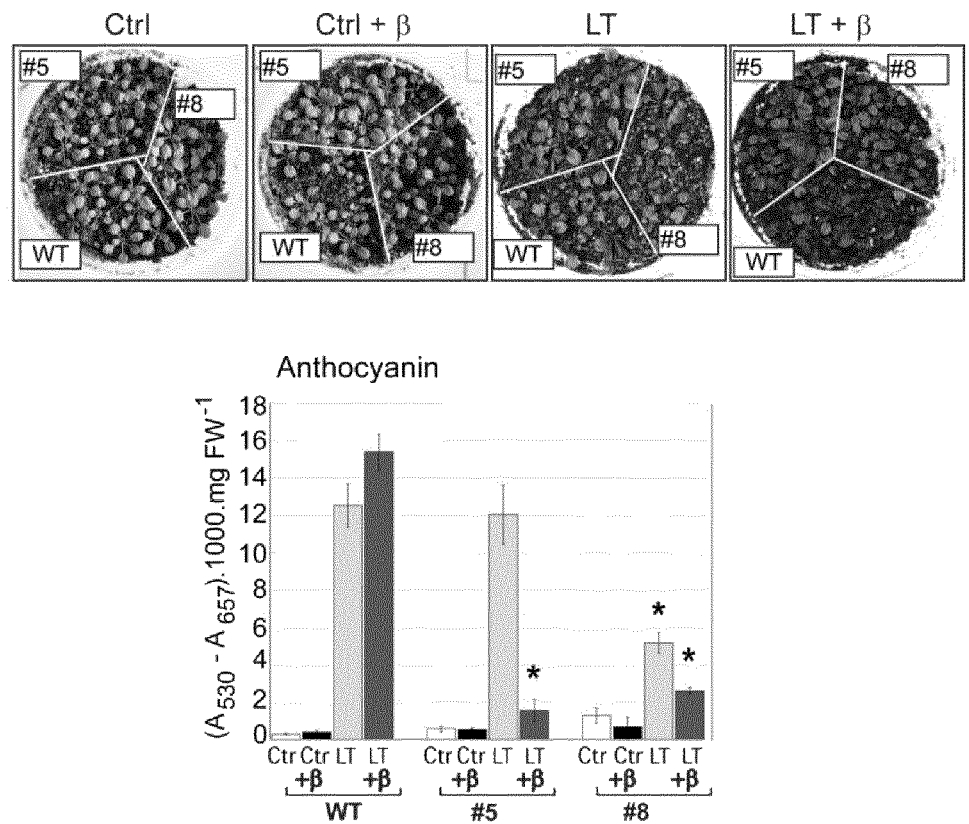
FIG. 13. Effect of the heterologous expression of GmeIFiso4G in *Arabidopsis* in exposure to cold stress Ten days old *Arabidopsis* plants were exposed to low temperature (4° C.) for two weeks and photographed. Controls (plants grown at 22° C.) and cold stressed plants (LT), treated with of 5 µM β-estradiol (+β), or untreated, were photographed two weeks after the onset of stress. Anthocyanin content was determined in plants growing at 22° C. (Ctrl) or exposed for 2 weeks to 4° C. (LT), in the presence (+β) or absence of β-estradiol. Asterisk (*) indicates significant differences between the wild type and the transgenic lines at p<0.05 confidence level.

Prolonged exposure of *Arabidopsis* transgenic plants with conditional overexpression of GmeIFiso4G-1, to low temperature (4° C.) resulted in reduced plant growth and high accumulation of anthocyanin in all plant genotypes. However, β-estradiol treatment reduced stress symptoms and anthocyanin accumulation in transgenic lines but not in the wild type (FIG. 13). Taking together, the results indicate that ectopic overexpression of GmeIFiso4G-1a increases plant tolerance to various abiotic stresses.

1.8.4. Phenotypic Analysis of Transgenic Soybean Plants

Soybean genotypes (wild type Jack cv and transgenic lines) were grown until they reached V2 developmental stage. During this period, plants were grown in soil irrigated at maximum soil water retention capacity. Experimental replicas of six pots per genotype and per treatment were used, and the replicas were randomly distributed in the growth chamber to rule out possible variations due to small differences in environmental conditions that may have occurred in different locations within the growth chamber. Plants were subjected to drought stress at V2 stage during 10 days by terminating irrigation. Non-stressed control plants continued to be daily irrigated at maximum soil water retention capacity as they were before reaching the V2 stage. Well-irrigated plants and stressed plants were analyzed for root development and oxidative stress and cell damage in leaves.

Figure 15:
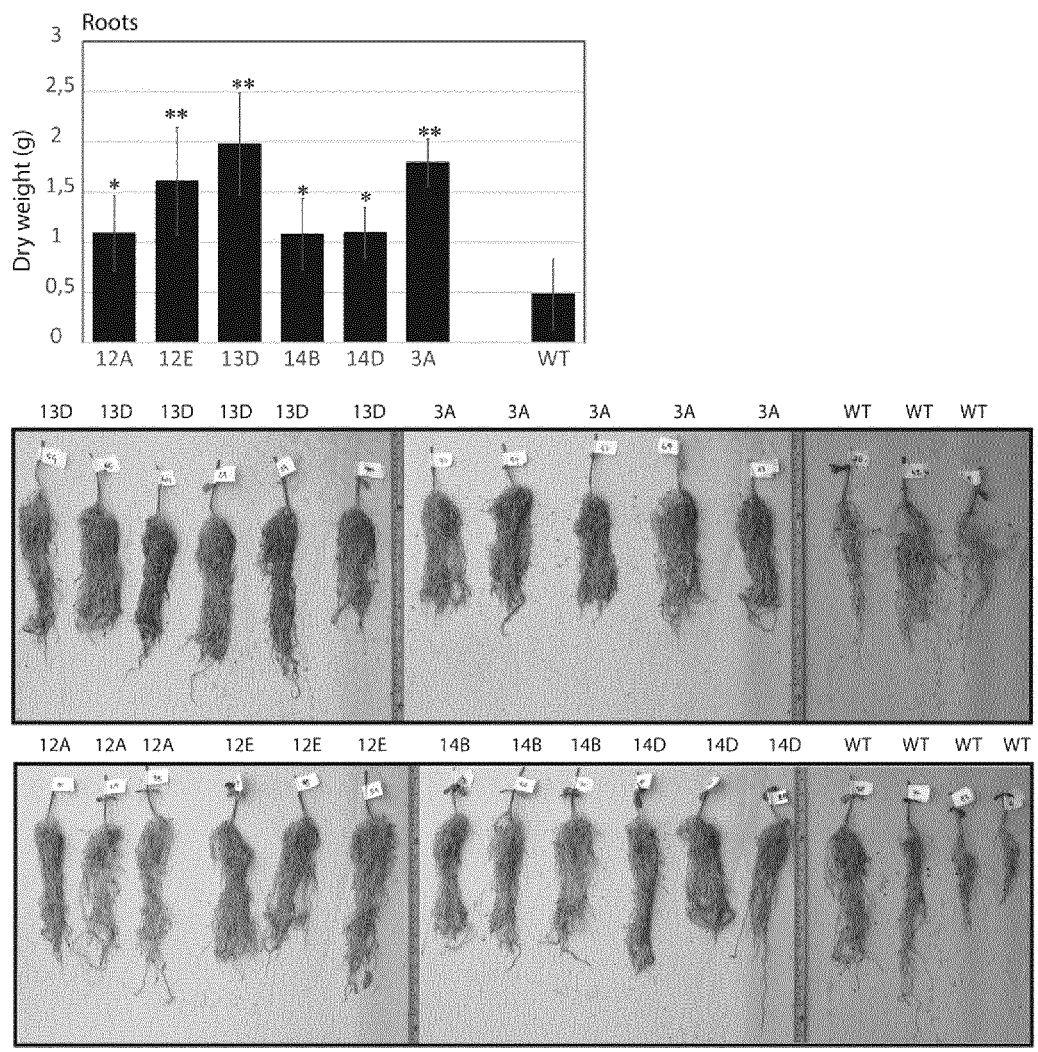
FIG. 15. OE_SEO roots. Effect of the heterologous expression of GmSEO in root development of soybean plants. Root from transgenic overexpressing lines (3A, 12A, 12E, 13D, 14B and 14D) and the wild type Jack cv: WT (J) were photographed at V3-4 stage and used for dry weight (in grams) determination. The values shown are means from one representative technical replicate. Error bars indicate SD (n=6). Significant differences of at least 0.05 confidence level between transgenic lines and wild type are marked by asterisks.

Roots from well irrigated plants were separated from the substrate, dried during 7 days at 80° C. and dry weight was determined (FIG. 15).

Figure 16:
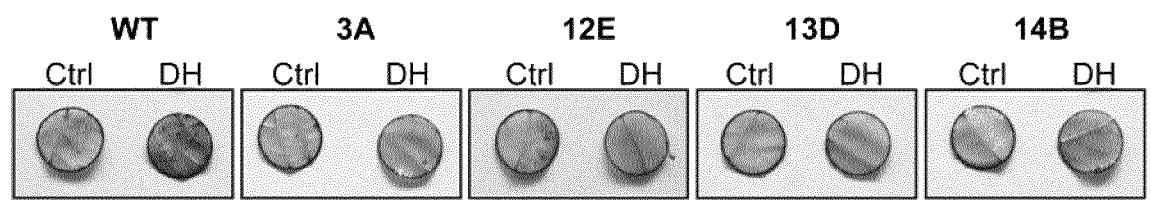
FIG. 16. NBT and SCHIFF. Effect of the overexpression of GmSEO in soybean in oxidative stress and cell damage of drought stressed plants. Leaf discs were sampled from well irrigated controls (Ctrl) and drought stressed (DH) soybean plants. GmSEO overexpressing lines (3A, 12A, 12E, 13D, 14B, 14D), and wild type Jack cv (WT) were used. In situ determination of $O2^-$ was performed by staining leaf disks with NBT. Lipid peroxidation was visualized by staining leaf discs with Schiff's reagent. Images are the most representative of a pool of five leaf disks per plant/per treatment.
Figure 16:
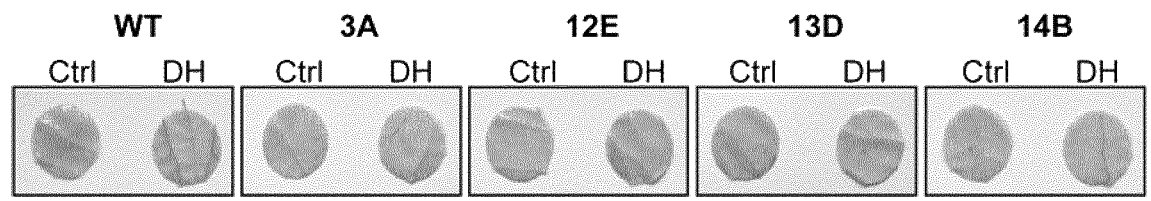

Leaf disc samples were taken from leaf material from the second trifoliate from 6 plants from each genotype (control or stressed), and used for NBT staining (in situ determination of O2), or Schiff's reagent staining (for detection of aldehydes derived from lipid peroxidation) (FIG. 16). These assays were used as biomarkers of stress-induced reactive oxygen species and cell damage. In situ detection of superoxide was performed according to Jabs et al., (*Science*, 273:1853-1856). Soybean leaf discs were vacuum infiltrated with 10 mM potassium phosphate buffer pH 7.8, 10 nM NaN3, 0.05% (v/v) Tween 20, containing 1 mg/ml nitro blue tetrazolium (NBT) for superoxide detection, the infiltrated leaves were kept for 30 min under daylight conditions prior to ethanol bleaching. Histochemical detection of lipid peroxidation was done with Schiff's reagent, which detects aldehydes that can be generated from lipid peroxides according to Signorelli et al., (Plant Science, 2013; 201-202:137-146). Leaf discs were incubated in Schiff's reagent for 60 min and then were bleached by immersing in boiling ethanol during 60 min.

The invention claimed is:

1. A transgenic plant with an increased abiotic stress tolerance, wherein the abiotic stress comprises osmotic, salinity, drought stress or cold stress, wherein said plant: (i) expresses a nucleic acid sequence shown in SEQ ID NO: 2 wherein if said transgenic plant is a soybean plant, then at least one copy of said nucleic acid sequence is found in a location in the genome different from the location where it naturally occurs or is under the control of a promoter which is not the naturally occurring promoter, or (ii) expresses a nucleic acid sequence shown in SEQ ID NO: 11, wherein if said transgenic plant is a soybean plant, then at least one copy of said nucleic acid sequence is found in a location in the genome different from the location where it naturally occurs or is under the control of a promoter which is not the naturally occurring promoter.

2. The plant according to claim 1 wherein said plant is soybean.

3. A part of the plant according to claim 1 or a product derived from said plant or from a part thereof.

4. A vector comprising (i) a sequence selected from the group consisting of SEQ ID NO: 2 and SEQ ID NO: 11 and (ii) a heterologous promoter sequence.

5. The vector according to claim 4 wherein the heterologous promoter sequence is a heterologous inducible promoter.

6. A host cell comprising a vector according to claim 4.

7. A method for producing a transgenic plant having increased abiotic stress tolerance, wherein the abiotic stress comprises osmotic, salinity, drought stress or cold stress, said method comprising introducing into said plant a sequence selected from the group consisting of SEQ ID NO: 2, and SEQ ID NO: 11, or alternatively introducing a vector comprising (i) a sequence selected from the group consisting of SEQ ID NO: 2, SEQ ID NO: 11; and (ii) a heterologous promoter sequence; wherein said transgenic plant is a soybean plant, and at least one copy of said nucleic acid sequence is found in a location in the genome different from the location where it naturally occurs or is under the control of a promoter which is not the naturally occurring promoter.

8. A method for increasing yield and/or growth of a plant under abiotic stress conditions, wherein the abiotic stress comprises osmotic, salinity, drought stress or cold stress, said method comprising increasing the expression of a sequence selected from the group consisting of SEQ ID NO: 2, and SEQ ID NO: 11 in said plant; or alternatively introducing a vector comprising (i) a sequence selected from the group consisting of SEQ ID NO: 2 and SEQ ID NO: 11; and (ii) a heterologous promoter sequence; wherein said transgenic plant is a soybean plant, and at least one copy of said nucleic acid sequence is found in a location in the genome different from the location where it naturally occurs or is under the control of a promoter which is not the naturally occurring promoter.

9. A method for increasing abiotic stress tolerance, such as for increasing osmotic, salinity, drought stress or cold stress tolerance, of a plant, which comprises increasing the expression of a sequence selected from the group consisting of SEQ ID NO: 2, and SEQ ID NO: 11 in said plant; or alternatively introducing a vector comprising (i) a sequence selected from the group consisting of SEQ ID NO: 2 and SEQ ID NO: 11; and (ii) a heterologous promoter sequence; wherein said transgenic plant is a soybean plant, and at least one copy of said nucleic acid sequence is found in a location in the genome different from the location where it naturally occurs or is under the control of a promoter which is not the naturally occurring promoter.

10. The method according to claim 8 wherein the increasing of the expression of a sequence selected from the group consisting of SEQ ID NO: 2, and SEQ ID NO: 11 is obtained by introducing into said plant a sequence selected from the group consisting of SEQ ID NO: 2, SEQ ID NO: 11.

* * * * *